(12) United States Patent
Lickrish et al.

US010292937B2

(10) Patent No.: US 10,292,937 B2
(45) Date of Patent: *May 21, 2019

(54) METHODS OF TREATMENT OF ATTENTION DEFICIT HYPERACTIVITY DISORDER

(71) Applicant: Ironshore Pharmaceuticals & Development, Inc., Camana Bay (KY)

(72) Inventors: David Lickrish, Grand Cayman (KY); Feng Zhang, Pflugerville, TX (US)

(73) Assignee: IRONSHORE PHARMACEUTICALS & DEVELOPMENT, INC., Camana Bay (KY)

(*) Notice: Subject to any disclaimer, the term of this patent is extended or adjusted under 35 U.S.C. 154(b) by 0 days.

This patent is subject to a terminal disclaimer.

(21) Appl. No.: 15/470,697

(22) Filed: Mar. 27, 2017

(65) Prior Publication Data

US 2017/0296477 A1 Oct. 19, 2017
US 2019/0060244 A9 Feb. 28, 2019

Related U.S. Application Data

(63) Continuation of application No. 14/716,777, filed on May 19, 2015, now Pat. No. 9,603,809, which is a continuation-in-part of application No. 14/577,963, filed on Dec. 19, 2014, now Pat. No. 9,034,902, which is a continuation of application No. 14/230,067, filed on Mar. 31, 2014, now Pat. No. 8,916,588, which is a continuation-in-part of application No. 13/429,292, filed on Mar. 23, 2012, now Pat. No. 9,028,868.

(60) Provisional application No. 61/466,684, filed on Mar. 23, 2011, provisional application No. 61/561,763, filed on Nov. 18, 2011, provisional application No. 61/591,129, filed on Jan. 26, 2012.

(51) Int. Cl.
*A61K 9/50* (2006.01)
*A61K 31/4458* (2006.01)

(52) U.S. Cl.
CPC .......... *A61K 9/5073* (2013.01); *A61K 9/5026* (2013.01); *A61K 9/5047* (2013.01); *A61K 31/4458* (2013.01)

(58) Field of Classification Search
None
See application file for complete search history.

(56) References Cited

U.S. PATENT DOCUMENTS

| 4,309,405 A | 1/1982 | Guley et al. |
| 4,687,660 A | 8/1987 | Baker et al. |
| 4,904,476 A | 2/1990 | Mehta et al. |
| 4,963,365 A * | 10/1990 | Samejima ............ A61K 9/5078 424/461 |
| 5,137,733 A | 8/1992 | Noda et al. |
| 5,260,068 A | 11/1993 | Chen |
| 5,266,331 A | 11/1993 | Oshlack et al. |
| 5,496,561 A | 3/1996 | Okada et al. |
| 5,498,581 A | 4/1996 | Chen |
| 5,508,042 A | 4/1996 | Oshlack et al. |
| 5,549,912 A | 8/1996 | Oshlack et al. |
| 5,656,295 A | 8/1997 | Oshlack et al. |
| 5,658,590 A | 8/1997 | Heiligenstein et al. |
| 5,837,284 A | 11/1998 | Mehta et al. |
| 5,874,090 A | 2/1999 | Baker et al. |
| 5,908,850 A | 6/1999 | Zeitlin et al. |
| 5,958,446 A | 9/1999 | Miranda et al. |
| 6,210,705 B1 | 4/2001 | Mantelle et al. |
| 6,228,398 B1 | 5/2001 | Devane et al. |
| 6,254,887 B1 | 7/2001 | Miller et al. |
| 6,287,599 B1 | 9/2001 | Burnside et al. |
| 6,322,819 B1 | 11/2001 | Burnside et al. |
| 6,344,215 B1 | 2/2002 | Bettman et al. |
| 6,348,211 B1 | 2/2002 | Mantelle et al. |
| 6,355,656 B1 | 3/2002 | Zeitlin et al. |
| 6,384,020 B1 | 5/2002 | Flanner et al. |
| 6,500,459 B1 | 12/2002 | Chhabra et al. |
| 6,524,620 B2 | 2/2003 | Chen et al. |
| 6,528,530 B2 | 3/2003 | Zeitlin et al. |
| 6,569,456 B2 | 5/2003 | Faour et al. |
| 6,605,300 B1 | 8/2003 | Burnside et al. |
| 6,627,223 B2 | 9/2003 | Percel et al. |

(Continued)

FOREIGN PATENT DOCUMENTS

| CA | 2 718 639 | 10/2009 |
| EP | 1143937 | 6/2004 |

(Continued)

OTHER PUBLICATIONS

Extended European Search Report dated Aug. 26, 2014.
International Search Report dated Jul. 3, 2012.
Aoyama, T., et al., "Nonlinear kinetics of threo-methylphenidate enantiomers in a patient with narcolepsy and in healthy volunteers," Eur. J. Clin. Pharmacol (1993) 44: 79-84.
Aoyama, Takao, et al., "Kinetic Analysis of Enantiomers of threo-Methylphenidate and Its Metabolite in Two Healthy Subjects after Oral Administration as Determined by a Gas Chromatographic-Mass Spectrometric Method," J. of Pharmaceutical Sciences, vol. 79, No. 6, Jun. 1990.
Aoyama, Takao, et al., "Pharmacodynamic Modeling for Change of Locomotor Activity by Methylphenidate in Rats," Pharmaceutical Research, vol. 14, No. 11, 1997.

(Continued)

*Primary Examiner* — Michael P Cohen
(74) *Attorney, Agent, or Firm* — Baker Botts L.L.P.

(57) ABSTRACT

Therapeutic compositions and methods for treatment of attention deficit disorder (ADD) or attention deficit hyperactivity disorder (ADHD) include dosage forms that deliver a therapeutic amount of active drug in a delayed and controlled release formulation. The dosage form can be administered at night and drug release is delayed for from 5 to 7 hours or longer, followed by an ascending release rate. When administered at night the composition provides early morning improvement in symptoms of ADHD and sustained improvement over a period of at least 12 hours.

10 Claims, 32 Drawing Sheets

(56) References Cited

U.S. PATENT DOCUMENTS

| | | | |
|---|---|---|---|
| 6,635,284 B2 | 10/2003 | Mehta et al. | |
| 6,730,325 B2 | 5/2004 | Devane et al. | |
| 6,733,789 B1 | 5/2004 | Stark et al. | |
| 6,743,182 B2 | 6/2004 | Miller et al. | |
| 6,811,794 B2 | 11/2004 | Burnside et al. | |
| 6,898,455 B2 | 5/2005 | Anderson et al. | |
| 6,913,768 B2 | 7/2005 | Couch et al. | |
| 6,919,373 B1 | 7/2005 | Lam et al. | |
| 6,930,129 B2 | 8/2005 | Lam et al. | |
| 7,037,260 B2 | 5/2006 | Keirsbilck et al. | |
| 7,074,420 B2 | 7/2006 | Miller et al. | |
| 7,105,486 B2 | 9/2006 | Mickle et al. | |
| 7,108,866 B1 | 9/2006 | Albert et al. | |
| 7,195,778 B2 | 3/2007 | Fleshner-Barak et al. | |
| 7,223,735 B2 | 5/2007 | Mickle et al. | |
| 7,244,769 B2 | 7/2007 | Epstein et al. | |
| 7,348,028 B2 | 3/2008 | Albert et al. | |
| 7,431,944 B2 | 10/2008 | Mehta et al. | |
| 7,655,630 B2 | 2/2010 | Mickle | |
| 7,659,253 B2 | 2/2010 | Mickle et al. | |
| 7,659,264 B2 | 2/2010 | Mickle et al. | |
| 7,662,787 B2 | 2/2010 | Mickle et al. | |
| 7,671,030 B2 | 3/2010 | Mickle et al. | |
| 7,671,031 B2 | 3/2010 | Mickle et al. | |
| 7,674,774 B2 | 3/2010 | Mickle et al. | |
| 7,678,770 B2 | 3/2010 | Mickle et al. | |
| 7,678,771 B2 | 3/2010 | Mickle et al. | |
| 7,687,466 B2 | 3/2010 | Mickle et al. | |
| 7,687,647 B2 | 3/2010 | Mickle et al. | |
| 7,691,881 B2 | 4/2010 | Kato et al. | |
| 7,700,561 B2 | 4/2010 | Mickle et al. | |
| 7,718,619 B2 | 5/2010 | Mickle et al. | |
| 7,723,305 B2 | 5/2010 | Mickle et al. | |
| 7,776,314 B2 | 8/2010 | Bartholomaus et al. | |
| 7,910,128 B2 | 3/2011 | Chang et al. | |
| 7,988,993 B2 | 8/2011 | Dixit et al. | |
| 8,916,588 B2 * | 12/2014 | Lickrish | A61K 9/5026 424/400 |
| 8,927,010 B2 * | 1/2015 | Lickrish | A61K 9/5026 424/458 |
| 9,023,389 B1 * | 5/2015 | Lickrish | A61K 9/5026 424/461 |
| 9,028,868 B2 * | 5/2015 | Lickrish | A61K 9/5026 424/464 |
| 9,034,902 B2 * | 5/2015 | Lickrish | A61K 9/5026 424/452 |
| 9,119,809 B2 * | 9/2015 | Lickrish | A61K 9/5026 |
| 9,283,214 B2 * | 3/2016 | Lickrish | A61K 9/4866 |
| 9,289,394 B2 * | 3/2016 | Lickrish | A61K 9/5026 |
| 9,498,447 B2 * | 11/2016 | Lickrish | A61K 9/0053 |
| 9,511,032 B2 * | 12/2016 | Lickrish | A61K 9/5026 |
| 9,603,808 B2 * | 3/2017 | Lickrish | A61K 9/5026 |
| 9,603,809 B2 * | 3/2017 | Lickrish | A61K 9/5026 |
| 2003/0161874 A1 | 8/2003 | Li et al. | |
| 2003/0170181 A1 | 9/2003 | Midha | |
| 2004/0059002 A1 | 3/2004 | Couch et al. | |
| 2004/0137062 A1 | 7/2004 | Chopra | |
| 2004/0156896 A1 | 8/2004 | Dixit et al. | |
| 2004/0213847 A1 | 10/2004 | Matharu et al. | |
| 2004/0220277 A1 | 11/2004 | Couch et al. | |
| 2005/0112201 A1 * | 5/2005 | Baichwal | A61K 9/286 424/470 |
| 2005/0158384 A1 * | 7/2005 | Couch | A61K 9/5015 424/468 |
| 2007/0036843 A1 | 2/2007 | Hirsh et al. | |
| 2007/0042955 A1 | 2/2007 | Mickle et al. | 514/12 |
| 2007/0048378 A1 | 3/2007 | Swanson et al. | 424/469 |
| 2007/0264323 A1 | 11/2007 | Shojaei et al. | |
| 2009/0041840 A1 | 2/2009 | Ayala | |
| 2009/0110728 A1 | 4/2009 | Rastogi et al. | |
| 2009/0123554 A1 | 5/2009 | Krishnamurthy et al. | |
| 2009/0202634 A1 | 8/2009 | Jans et al. | |
| 2009/0220611 A1 | 9/2009 | Dargelas et al. | |
| 2009/0324716 A1 | 12/2009 | Shen et al. | |
| 2010/0047341 A1 | 2/2010 | Kim et al. | |
| 2010/0074951 A1 | 3/2010 | Kim et al. | |
| 2010/0093796 A1 | 4/2010 | Gupta et al. | |
| 2010/0166889 A1 | 7/2010 | Sanfilippo | |
| 2010/0261712 A1 | 10/2010 | Sackler | |
| 2011/0077238 A1 | 3/2011 | Leech et al. | |
| 2011/0201645 A1 | 8/2011 | Zeitlin et al. | |
| 2011/0268799 A1 | 11/2011 | Dixit et al. | |

FOREIGN PATENT DOCUMENTS

| | | |
|---|---|---|
| EP | 1 782 798 | 5/2007 |
| GB | 2 230 442 | 10/1990 |
| WO | WO 1996/41617 | 12/1996 |
| WO | WO 1997/27176 | 7/1997 |
| WO | WO 1997/28124 | 8/1997 |
| WO | WO 1997/32851 | 9/1997 |
| WO | WO 1997/35836 | 10/1997 |
| WO | WO 1998/14168 | 4/1998 |
| WO | WO 1998/23263 | 6/1998 |
| WO | WO 1998/25902 | 6/1998 |
| WO | WO 1998/31668 | 7/1998 |
| WO | 00/23055 A1 | 4/2000 |
| WO | 2001010420 A1 | 2/2001 |
| WO | 2008079404 A2 | 7/2008 |
| WO | WO 2008/122967 | 10/2008 |
| WO | WO 2009/117819 | 10/2009 |

OTHER PUBLICATIONS

Aoyama, Takao, et al., "Pharmacokinetics and pharmacodynamics o methylphenidate enantiomers in rats," Psychopharmacology (1996) 127:117-122.

Axten, Jeffrey M., et al., "A Stereoselective Synthesis of dl-threo-Methylphenidate: Preparation and Biological Evaluation of Novel Analogues," J. Org. Chem. 1998, 63, 9628-9629.

Barkley, Russell A., et al., "The Adolescent Outcome of Hyperactive Children Diagnosed by Research Criteria: I. An 8-Year Prospective Follow-up Study," J. Am. Acad. Child Adolec. Psychiatry, 29:4, Jul. 1990.

Bruera, Eduardo, et al., "Methylphenidate Associated With Narcotics for the Treatment of Cancer Pain[1]," Cancer Treatment Reports, vol. 71, No. 1, Jan. 1987.

Bruera, Eduardo, et al., "Narcotics Plus Methylphenidate (Ritalin) for Advanced Cancer Pain," Am. J. of Nursing, Nov. 1988.

Bruera, Eduardo, et al., "Neuropsychological effects of methylphenidate in patients receiving a continuous infusion of narcotics for cancer pain," Pain, 48 (1992).

Bruera, Eduardo, et al., "Overwhelming Fatigue in Advanced Cancer," Am. J. of Nursing, Jan. 1988.

Bruera, Eduardo, et al., "The use of methylphenidate in patients with incident cancer pain receiving regular opiates. A preliminary report." Pain, 50 (1992) 75-77.

Bruera, Eduardo, et al., "The Uses of Psychotropics in Symptom Management in Advanced Cancer," Psycho-Oncology 7: 346-358 (1998).

Bussemer, T., et al., "A pulsatile drug delivery system based on rupturable coated hard gelatin capsules," J. of Controlled Release 93 (2003) 331-339.

Bussemer, T., et al., "Time-Dependent Mechanical Properties of Polymeric Coatings Used in Rupturable Pulsatile Release Dosage Forms," Drug Development and Industrial Pharmcy, vol. 29, No. 6, pp. 623-630, 2003.

Chemical Abstracts~Key to the World's Chemical Literature, vol. 104, No. 21, May 26, 1986.

Chromobio, "Gas chromatographic-mass spectrometric analysis of threo-methylphanidate enantiomers in plasma," J. of Chromatography, 494 (1989) 420-423.

Deutsch, Howard M., et al., "Synthesis and Pharmacology of Potential Cocaine Antagonists," J. Med. Chem, vol. 39, No. 6, 1201-1209, 1996.

Ding, Y.S., et al., "Chiral drugs: comparison of the pharmacokinetics of [$^{11}$C]d-threo and l-threo-methylphenidate in the human and baboon brain," Psychopharmacology (1997) 131:71-78.

(56) References Cited

OTHER PUBLICATIONS

Drimmer, Eric, J., et al., "Desipramine and Methylphenidate Combination Treatment for Depression: Case Report." Am. J. Psychiatry 140:2, Feb. 1983.

Eckerman, David A., et al., "Enantioselective Behavioral Effects of threo-Methylphenidate in Rats," Pharmacology Biochemistry & Behavior, vol. 40, pp. 875-880, 1991.

Ermer, James C., "Bioavailability of triple-bead mixed amphetamine salts compared with a dose-augmentation strategy of mixed amphetamine salts extended release plus mixed amphetamine salts immediate release," Current Medical Research and Opinion, vol. 23, No. 5, 2007, 1067-1075.

Farone, Stephen V., et al., "Pathophysiology of Attention-Deficit/Hyperactivity Disorder," Neuropsychopharmacology: The Fifth Generation of Progress, 2002.

Fernandez, Francisco, et al., "Methylphenidate for depressive disorders in cancer patients," Psychosomatics, Sep. 1987, vol. 28, No. 9.

Fernandez, Francisco, et al., "Methylphenidate Treatment of Patients With Head and Neck Cancer," Head & Neck Surgery, Mar./Apr. 1986.

Ferris, R.M., et al., A comparison of the capacities of isomers of amphetamine, deoxypipradrol and methylphenidate to inhibit the uptake of tritiated catecholamines into rat.

Ferris, R.M., et al., "Comparison of the Effects of the Isomers of Amphetamine, Methylphenidate and Deoxypipradrol on the Uptake of 1-[$^3$H]Norepinephrine and [$^3$H]Dopamine by Synaptic Vesicles from Rate Whole Brain, Striatum and Hypothalamus," The J. of Pharmacology and Experimental Therapeutis, vol. 21, 1979.

Folstein, Marshal F., et al., "A Practical Method for Grading the Cognitive State of Patients for the Clinician," J. Psychiat. Res., 1975, vol. 12, pp. 189-198.

Garland, E. Jane, "Pharmacotherapy of adolescent attention deficit hyperactivity disorder: challenges, choices and caveats," J. of Psychopharmacology 12(4) (1998) 385-395.

Golden, Gerald S., "Role of Attention Deficit Hyperactivity Disorder in Learning Disabilities," Seminars in Neurology—vol. 11, No. 1 Mar. 1991.

Goldman, Larry S., et al., "Diagnosis and Treatment of Attention-Deficit/Hyperactivity Disorder in Children end Adolescents," JAMA, vol. 279, No. 14, Apr. 8, 1998.

Grace, Anthony A., "Psychostimulant Actions on Dopamine and Limbic System Function: Relevance to the Pathophysiology and Treatment of ADHD," Stimulant Drugs and ADHD Basic and Clinical Neuroscience (2001).

Greenblatt, David J., et al., "Pharmacokinetic, Pharmacodynamics, and Drug Disposition," Neuropsychopharmacology: The Fifth Generation of Progress, 2002.

Grob, Charles S., et al., "Suspected Adverse Methylphenidate-Imipramine Interactions in Children," Development and Behavior Pediatics, vol. 7, No. 4, Aug. 1986.

Gulati, Dushyant, et al., Methylphenidate Hydrochloride, Environmental Health Perspective, vol. 105, Supplement 1, Feb. 1997.

Hales, Robert E., et al., "Psychopharmacologic Issues in the Diagnosis and Treatment of Organic Mental Disorders," Psychiatric Clinics of No. Am. vol. 7, No. 4, Dec. 1984.

Hubbard, John W., et al., "Enantioselective Aspects of the Disposition of dl-threo-Methylphenidate after the Administration of a Sustained-Release Formulation to Children with Attention Deficit-Hyperactivity Disorder," J. of Pharmaceutical Sciences, vol. 78, No. 11, Nov. 1989.

Ishino, Ryuzo, et al., "Design and Preparation of Pulsatile Release Tablet as a New Oral Drug Delivery System," Chem. Pharm. Bull. 40(11) 3036-3041 (1992).

Jain, Sanjay K., et al., "Design and Development of Hydrogel Beads for Targeted Drug Delivery to the Colon," AAPS PharmSciTech 2007; 8 (3) Article 56.

Jonkman, Lisa M., et al., "Differences in plasma concentrations of the D- and L-threo methylphenidate enantiomers in responding and non-responding children with attention-deficit hyperactivity disorder," Psychiatry Research 78 (1998) 115-118.

Kadouch, Rachel, et al., "The Mood Response and Plasma Cyclic-AMP Response to Intravenous Methylphenidate," Neuropsychobiology 3: 250-255 (1977).

Kahlig, Kristopher M., et al., "Amphetamine induces dopamine efflux through a dopamine transporter channel," PNAS vol. 102, No. 9, Mar. 1, 2005.

Lin, Jiunn H., et al., "Role of Pharmacokinetics and Metabolism in Drug Discovery and Development," Pharmacological Reviews, vol. 49, No. 4 (1997).

Llana, Maria E., et al., "Methylphenidate: Increased Abuse or Appropriate Use?" J. of Am. Pharmaceutical Assoc., vol. 39, No. 4, Jul./Aug. 1999.

Lopez, Frank A., et al., "Physician perception of clinical improvement in children with attention-deficit/hyperactivliy disorder: a post hoc comparison of lisdexamtetamine dimesylate and mixed amphetamine salts extended release in a crossover analog classroom study," Neuropsychiatric Disease and Treatment 2011:7 267-273.

Macleod, A.D., et al., "Methylphenidate in Terminal Depression," J. of Pain and Symptom Management, vol. 16, No. 3, Sep. 1998.

Markowitz, John S., et al., "Advances in the Pharmacotherapy of Attention-Deficit-Hyperactivity Disorder: Focus on Methylphenidate Formulations," Pharmcotherapy 23(a0): 1281-1299, 2003.

Markowitz, John S., et al., "Pharmacokinetic and Pharmacodynamic Drug Interactions in the Treatment of Attention-Deficit Hyperactivity Disorder," Clin Pharmacokinet 2001: 40 (10).

Matsuo, Mitsuyuki, et al., "Evaluation of Hydroxyethylcellulose as a Hydrophilic Swellable Material for Delayed-Release Tablets," Chem. Pharm. Bull. 43(20) 311-314 (1995).

Melega, William P., et al., "Pharmacokinetic and Pharmacodynamic Analysis of the Actions of $_o$-Amphetamine and $_o$-Methamphetamine on the Dopamine Terminal[1]," The J. of Pharmacology and Experimental Therapeutics, vol. 274, No. 1, 1995.

Meyers, Christina A., et al., "Methylphenidate Therapy Improves Cognition, Mood, and Function of Brain Tumor Patients," J. of Clinical Oncology, vol. 16, No. 7 Jul. 1998.

Nangia, Avinash, "BIOROD™: Bioadhesive-Based Oral System for Targeted Delivery," Drug Delivery Technology, Oct. 2008, vol. 8, No. 8.

Narisawa, Shinji, et al., "An Organic Acid-Induced Sigmoidal Release System for Oral Controlled-Release Preparations. 2. Permeability Enhancement of Eudragit RS Coating Led by Physicochemical Interactions with Organic Acid," J. of Pharm. Sciences, vol. 85, No. 2, Feb. 1996.

Olin, Jonathan, et al., "Psychostimulants for Depression in Hospitalized Cancer Patients," Psychosomatics, vol. 37, No. 1, Jan.-Feb. 1996.

Pastor, Patricia N., et al., "Diagnosed Attention Deficit Hyperactivity Disorder and Learning Disability: United States, 2004-2006," Vital and Health Statistics, Series 10, No. 237, Jul. 2008.

Patrick, Kennerly S., et al., "Distribution of Methylphenidate and p-Hydroxymethylphenidate in Rats[1]," The J. of Pharmacology and Experimental Therapeutics, vol. 231, No. 1, 1984.

Patrick, Kennerly S., et al., "New methylphenidate formulations for the treatment of attention-deficit/hyperactivity disorder," Expert Opin. Drug Deliv. (2005) 2(1).

Patrick, Kennerly S., et al., "Pharmacology of Methylphenidate, Amphetamine Enantiomers and Pemoline in Attention-Deficit Hyperactivity Disorder," Human Psychopharmacology, vol. 12, 527-546 (1997).

Patrick, Kennerly S., et al., "The Absorption of Sustained-Release Methylphenidate Formulations Compared to an Immediate-Release Formulation," Biopharmaceutics & Drug Disposition, vol. 10, 165-171 (1989).

Patrick, Kennerly, et al., "Synthesis of Deuterium-Labelled Methylphenidate, p-Hydroxymethylphenidate, Ritalinic Acid and p-Hydroxyritalinic Acid," J. of Labelled Compounds and Radiopharmaceuticals, vol. IX, No. 4, Apr. 1982.

Pelham, William E, Jr., et al., "Sustained Release and Standard Methylphenidate Effects on Cognitive and Social Behavior in Children With Attention Deficit Disorder," Pediatrics vol. 80, No. 4, p. 491-501. Oct. 1987.

(56) References Cited

OTHER PUBLICATIONS

Quinn, Declan M.P., "Methylphenidate: The Role of the d-Isomer," Ritalin: Theory and Practice, 2000.
Quinn, Declan, et al., "Single-Dose Pharmacokinetics of Muitilayer-Release Methylphenidate and Immediate-Release Methylphenidate in Children With Attention-Deficit/Hyperactivity Disorder," J. Clin. Pharmacol. 2007; 47:760-766.
Rapport, Mark D., et al., "Methylphenidate and Desipramine in Hospitalized Children: I. Separate and Combined Effects on Cognitive Function" J. Am. Acad. Child Adolesc. Psychiatry, 32:2, Mar. 1993.
Roehrs, Timothy, et al., "Sleepiness and the Reinforcing and Subjective Effects of Methylphenidate," Experimental and Clinical Psychopharmacology, 1999, vol. 7, No. 2, 145-150.
Spencer, Thomas, et al.; "Pharmacotherapy of Attention-Deficit Hyperactivity Disorder across the Life Cycle," J. Am. Acad. Child Adolesc. Psychiatry, 35:4, Apr. 1996.
Srinivas, N.R., et al., "In Vitro Hydrolysis of RR,SS-threo-Methylphenidate by Blood Esterases—Differential and Enantioselective Interspecies Variability," Chirality 3:99-103 (1991).
Srinivas, Nuggehally R., et al., "Enantioselective pharmacokinetics and pharmacodynamics of dl-threo-methylphenidate in children with attention deficit hyperactivity disorder," Clin Pharmacol Ther, vol. 52, No. 5, Nov. 1992.
Stein, Mark A., et al., "Methylphenidate Dosing: Twice Daily Versus Three Times Daily," Pediatrics vol. 98, No. 4 Oct. 1996.
Stiebel, Victor, et. al., "Long-term Methylphenidate Use in the Medically Ill Patient With Organic Mood Syndrome," Psychosomatics, vol. 31, No. 4, Fall 1990.
Sun, Zejin, et al., "Methylphenidate Is Stereoselectively Hydrolyzed by Human Carboxylesterase CES1A1," J. of Pharmacology and Experimental therapeutics, vol. 310, No. 2, p. 469-476, 2004.
Swanson, James M., et al., "A Comparison of Once-Daily Extended-Release Methylphenidate Formulations in Children With Attention-Deficit/Hyperactivity Disorder in the Laboratory School (The Comacs Study)," Pediatrics, 2004; 113; e206.
Swanson, James M., et al., "Analog Classroom Assessment of Adderall in Children With ADHD," J. Am. Acad. Child Adolesc. Psychiatry, 37:5, May 1998.
Swanson, James M., et al., "Efficacy of a New Pattern of Delivery of Methylphenidate for the Treatment of ADHD: Effects on Activity Level in the Classroom and on the Playground," J. Am. Acad. Adolesc. Psychiatry, 41:11. Nov. 2002.
Swanson, James, "Development of a New Once-a-Day Formulation of Methylphenidate for the Treatment of Attention-deficit/Hyperactivity Disorder," Arch Gen Psychiatry, vol. 60. Feb. 2003.
Volkow, N.D., et al., "Temporal relationships between the pharmacokinetics of methylphenidate in the human brain and its behavioral and cardiovascular effects," Psychopharmacology (1996) 123: 26-33.
Weitzner, Michael, et al., "Methylphenidate in the Treatment of Neurobehavioral Slowing Associated With Cancer and Cancer Treatment," J. of Neuropsychiatry and Clinical Neurosciences 1995; 7:347-350.
Extended European Search Report for European Patent Application No. 17187023.1, dated Oct. 26, 2017; 8 pages, dated Oct. 26, 2017.
Sinha, V. R., and Rachna Kumria. "Binders for colon specific drug delivery: an in vitro evaluation." *International journal of pharmaceutics* 249.1-2 (2002): 23-31; 9 pages, 2002.
Davis, Caroline, et al. "Dopamine transporter gene (DAT1) associated with appetite suppression to methylphenidate in a case—control study of binge eating disorder." *Neuropsychopharmacology* 32.10 (2007): 2199; 8 pages, 2007.
Chan, Ying-Pui Mick, et al. "Methylphenidate hydrochloride given with or before breakfast: II. Effects on plasma concentration of methylphenidate and ritalinic acid." *Pediatrics* 72.1 (1983): 56-59; 4 pages, 1983.
Weiss, Gabrielle, et al. "Effect of long-term treatment of hyperactive children with methylphenidate." *Canadian Medical Association Journal* 112.2 (1975): 159; 7 pages, Jan. 25, 1975.
Patrick, Kennerly S., and John S. Markowitz. "Pharmacology of methylphenidate, amphetamine enantiomers and pemoline in attention-deficit hyperactivity disorder." *Human Psychopharmacology: Clinical and Experimental* 12.6 (1997): 527-546; 13 pages, 1997.
Frankenberger, William, et al. "The use of stimulant medication for treatment of Attention-Deficit/Hyperactivity Disorder: A survey of school psychologists' knowledge, attitudes, and experience." *Developmental Disabilities Bulletin* 29.2 (2001): 132-151, 2001.
Volkow, Nora D., et al. "Effects of methylphenidate on regional brain glucose metabolism in humans: relationship to dopamine D2 receptors." *The American journal of psychiatry* 154.1 (1997): 50, 1997.
Ward, Mark F. "The Wender Utah Rating Scale: An aid in the retrospective diagnosis of childhood attention deficit hyperactivity disorder." *American journal of Psychiatry* 150 (1993): 885-890, 1993.

* cited by examiner

METHODS OF TREATMENT OF ATTENTION DEFICIT HYPERACTIVITY DISORDER

CROSS-REFERENCE TO RELATED APPLICATIONS

This application is a continuation of U.S. application Ser. No. 14/716,777, filed May 19, 2015, which is a continuation-in-part of U.S. application Ser. No. 14/577,963, filed Dec. 19, 2014, now U.S. Pat. No. 9,034,902, which is a continuation of U.S. application Ser. No. 14/230,067, filed Mar. 31, 2014 now U.S. Pat. No. 8,916,588, which is a continuation-in-part of U.S. application Ser. No. 13/429,292, filed Mar. 23, 2012, now U.S. Pat. No. 9,028,868, which claims benefit of priority to US Provisional Application No. 61/466,684, filed Mar. 23, 2011, 61/561,763, filed Nov. 18, 2011 and 61/591,129, filed Jan. 26, 2012. All of the priority documents listed above are incorporated herein by reference in their entirety.

BACKGROUND

Attention deficit hyperactivity disorder (ADHD) is a developmental disorder characterized by symptoms such as impulsiveness, hyperactivity and/or inattentiveness. Hyperactivity is common among children with ADHD but tends to disappear during adulthood. However, over half of children with ADHD continue to have some symptoms of inattention throughout their lives.

Stimulant medications are widely used as a pharmacological treatment for ADHD. Stimulants, in the short term, have been found to be safe in the appropriately selected patient and appear well tolerated over five years of treatment. Active pharmaceutical agents now approved in the USA for use in treatment of ADHD are primarily effectors of the dopamine or norepinephrine neural pathways. Approved agents include salts and isomers of amphetamine and methylphenidate, the dextroamphetamine prodrug, lisdexamfetamine dimesylate, and atomoxetine.

One of the challenges of treating ADHD and other CNS stimulant responsive conditions is delivering and maintaining an effective concentration in patients throughout the day and in particular, in the morning hours when cognitive abilities and concentration are needed for school or work and in the late afternoon or evening when students often do homework. Early formulations relied on a twice daily administration of an immediate release formulation, causing problems with compliance. Various long-acting formulations were developed and are now available that have been shown in clinical trials to be effective for 8-14 hours (Brams et al., *Current Medical Research and Opinion*, vol. 26 no. 8, pgs 1809-1825, August 2010).

SUMMARY

The compositions and methods of the present disclosure provide novel formulations and methods for treating diseases or conditions that are responsive to CNS stimulants. Such conditions include but are not limited to ADD, ADHD, narcolepsy, excessive daytime sleepiness, major depressive disorder, bipolar depression, negative symptoms in schizophrenia, chronic fatigue, fatigue associated with chemotherapy or binge eating disorder. The compositions and methods are effective for treating the adult, pediatric and adolescent populations that are in need of such treatment.

The disclosed compositions and methods provide a convenient method of administration in that a single dose can be taken typically in the evening prior to going to bed, or at whatever time of day one retires for an extended period of sleep and the release of the drug is delayed for 4 to 12 hours in some examples and then released in a controlled or sustained manner. It is an aspect of the disclosure that the lag time can be controlled through design of the formulation and that the lag can thus be 4, 5, 6, 7, 8, 9, 10, 11, or 12 hours or intermediate times within the range. It is also understood that the administration time is not necessarily tied to a patient's sleep time or sleep cycle, but that administration can be from 4-12 hours prior to the time a patient needs a therapeutic dose whether he or she sleeps during the lag or not.

In certain embodiments, the compositions are water-soluble capsules that contain coated particles such as beads or minitablets. These particles are coated with an outer, delayed release coating and an inner, sustained release coating over a drug containing core. The delayed release allows the subject to sleep, and as the outer layer of the composition dissolves and the sustained release layer begins to lose some of its integrity, the drug starts to slowly release. This results in a low, but therapeutic level of drug in the plasma of the patient when that patient would normally wake up and prepare for the day. Subsequent to this slow release, the drug release rate increases over a period of about eight to ten hours or more, to continue to provide a therapeutic amount during the typically active part of the day. The compositions and methods disclosed herein thus provide a single dose that is conveniently taken prior to sleeping and that provides a therapeutic effect from the time a subject normally awakes and through the productive portion of the day.

Although the present compositions are described as effective as a once-a-day dosage, it is understood that additional doses can be administered as needed at the direction of a physician. The description herein is primarily directed to treatment of persons with a typical schedule of going to sleep from around 9 P.M. to about midnight, for example, and sleeping for 6-9 hours. It is understood, however, that the use and efficacy of the compositions and methods is not limited to such a schedule, but can be adopted for use with different daily schedules, such as night workers, or people with longer, shorter or more variable sleep patterns.

In certain embodiments, the compositions disclosed herein include, but are not limited to tablets, minitablets or beads contained in a water-soluble capsule. The minitablets or beads can include a drug containing core or a drug coated inert bead core in which the drug core or drug layer can also contain an optional disintegrant, osmagent or pore-forming agent. In certain embodiments the disintegrant can be a superdisintegrant. In certain embodiments the drug layer or core is enclosed by a sustained release layer that can include a water-insoluble and water permeable polymer layer that controls the rate of absorption of water and release of the drug. The outer, delayed release layer is coated on the sustained release layer. The delayed release layer may contain a plasticizer or solubility can be pH dependent. The delayed release layer can thus be a pH dependent layer that is insoluble in aqueous solution at a pH below 5.5 and soluble at the higher pH normally found in the ileum or colon, or it can be a pH independent layer. In certain embodiments, an outer, pH dependent layer dissolves in the higher pH of the ileum or colon. As the sustained release layer then loses integrity the sustained release layer ruptures and releases the remaining drug in the core.

The active ingredients include CNS stimulants that are effective to treat ADD and ADHD or other conditions associated with dopamine or norepinephrine neural pathways. The active ingredients include, but are not limited to the active isomers of amphetamines and amphetamine salts, or mixed amphetamine salts, including salts of dextroamphetamine, and methylphenidate and its active salts, all of which can be used as racemic mixtures or pure isomers such as d-threo methylphenidate. The disclosed compositions can also include one or more prodrug of CNS stimulants, including but not limited to amino acid conjugated active ingredients such as 1-lysine-d-amphetamine, for example.

The compositions and methods of the present disclosure can be described in certain embodiments, therefore, as solid, oral pharmaceutical compositions including a core comprising a therapeutic amount of a CNS stimulant, at least one pharmaceutically acceptable excipient and optionally a disintegrant, osmagent, or a pore-forming agent; a sustained release layer coating the core; and a delayed release layer enclosing the sustained release layer, wherein the combination of the sustained release and delayed release layers provide a 3-8, 10 or even 12-13 hour delay during which no more than 10% of the CNS stimulant is released when the composition is placed in a simulated gastric environment. The term simulated gastric environment is intended to be used herein to convey its ordinary meaning as understood in the art, and is understood in a broad sense to mean conditions that mimic oral administration, for example, an aqueous environment of low pH, 1-5 for example, followed after a period of up to about 2 hours with immersion in a higher pH aqueous environment, such as pH 6.8, for example, or a 3 stage environment in which the low pH is followed by an intermediate pH of about 6 wherein the environments are maintained at about 37.0° C. Alternatively, for certain embodiments a simulated gastric environment is described as the USP Apparatus I (Baskets) with agitation in which the composition is placed in 700 ml aqueous solution of 0.1N HCl pH 1.1, for up to 2 hours followed by 2-6 hours in sodium phosphate buffer at pH 6.0; followed by 6-20 hours in sodium phosphate buffer, pH 7.2, adding NaOH to adjust pH to 7.2.

Any of the solid oral pharmaceutical compositions disclosed herein can be in the form of coated beads, or they can be compressed into tablet or minitablet form. The beads or minitablets can then be apportioned in single dose amounts into water-soluble gelatin capsules, or into a liquid or gel suspension for administration.

An aspect of the compositions and methods of the present disclosure can also be described as solid, oral pharmaceutical compositions including a core comprising a therapeutic amount of a CNS stimulant and at least one pharmaceutically acceptable excipient wherein the core is substantially free of a disintegrant, osmagent, or a pore-forming agent; a sustained release layer coating the core; and a delayed release layer enclosing the sustained release layer, wherein the combination of the sustained release and delayed release layers provide a 3, 4, 5, 6, 7, 8, 9, 10, 11 or even a 12 hour delay during which no more than 10% of the CNS stimulant is released when the composition is placed in a simulated gastric environment.

A solid, oral pharmaceutical composition of the disclosure can be described as a formulation in which the in vitro dissolution rate of the dosage form when measured by the USP Apparatus I (Baskets) with agitation in which the composition is placed in 700 ml aqueous solution of 0.1N HCl pH 1.1, for up to 2 hours followed by 2-6 hours in sodium phosphate buffer at pH 6.0; followed by 6-20 hours in sodium phosphate buffer, pH 7.2, adding NaOH to adjust pH to 7.2 at 37° C.±0.5° C. is between 0 and about 20% drug released after 8 hours, between about 2 and about 30% released after 10 hours, between about 10% and about 65% released after 12 hours and between 45% and 95% released after 15 hours, and wherein the amount of active ingredient released per each hour increases from the period between 20% released and 65% released. The compositions and methods of the present disclosure can also be described as solid, oral pharmaceutical compositions in which the in vitro dissolution rate of the dosage form when measured by the USP Apparatus I (Baskets) with agitation in which the composition is placed in 700 ml aqueous solution of 0.1N HCl pH 1.1, for up to 2 hours followed by 2-6 hours in sodium phosphate buffer at pH 6.0; followed by 6-20 hours in sodium phosphate buffer, pH 7.2, adding NaOH to adjust pH to 7.2 at 37° C.±0.5° C. is between 0 and about 10% drug released after 6 hours, between about 15% and about 28% released after 10 hours, between about 40% and about 60% released after 12 hours and between about 80% and about 95% released after 15 hours, and wherein the amount of active ingredient released per each hour increases from the period between 20% released and 65% released, or as a solid, oral pharmaceutical composition as described when measured by the USP Apparatus I (Baskets) with agitation in which the composition is placed 700 ml aqueous solution of 0.1N HCl pH 1.1, for up to 2 hours followed by 2-6 hours in sodium phosphate buffer at pH 6.0; followed by 6-20 hours in sodium phosphate buffer, pH 7.2, adding NaOH to adjust pH to 7.2 at 37° C.±0.5° C., no more than about 10% of the agent is released within 6 hours and no more than about 50% of the agent is released within 12 hours, and wherein, when the composition is administered to a human, a plot of plasma concentration versus time after administration exhibits a single maximum between 12 and 20 hours after administration.

The solid oral pharmaceutical compositions of the present disclosure can also include a plurality of core pellets that in certain embodiments are substantially spherical beads. By substantially spherical beads is meant a population of beads in which the measured mean area ratio and circularity, are within 80% of a sphere. The core can consist essentially of a CNS stimulant and one or more excipients, or the core can consist essentially of the stimulant and one or more excipients coated on an inert non-pareil bead. These cores are then coated with two or more release control layers to produce a population of particles for drug delivery. It is an aspect of the compositions and methods of the present disclosure, however, that it is advantageous to provide a smooth spherical core to the extent possible in order to obtain a more consistent coating and a reproducible release profile of the active ingredient from the populations of particles.

The solid oral pharmaceutical compositions of the present disclosure also include a CNS stimulant which can be generally defined as a chemical entity that affects the dopamine or norepinephrine neural pathways. Preferred pharmaceutically active ingredients include, but are not limited to amphetamine, dextroamphetamine, the active isomers of amphetamines and amphetamine salts including salts of dextroamphetamine, methylphenidate and its active salts, or combinations thereof, all of which can be used as racemic mixtures or pure isomers such as d-threo methylphenidate, or a prodrug or pharmaceutical salt, or mixed pharmaceutical salts of any thereof alone or in combination. The disclosed compositions can also include a prodrug, including but not limited to amino acid conjugated active ingredients such as 1-lysine-d-amphetamine. Suitable excipients in the core of the pharmaceutical composition can include polyvinyl pyrollidone, hydroxypropylmethyl cellulose, lactose, sucrose, microcrystalline cellulose or combinations of any thereof.

It is an aspect of the disclosed compositions that the delayed release layer can include a pH dependent polymer or copolymer that is insoluble in aqueous medium at pH lower than 5.5. Such a delayed release layer can include, but is not limited to cellulose acetate phthalate, cellulose acetate trimaletate, hydroxyl propyl methylcellulose phthalate, polyvinyl acetate phthalate, acrylic polymers, polyvinyl acetaldiethylamino acetate, hydroxypropyl methylcellulose acetate succinate, cellulose acetate trimellitate, shellac, methacrylic acid copolymers, Eudragit L30D, Eudragit L100, Eudragit FS30D, Eudragit S100 or combinations of any thereof. The delayed release layer can also include a plasticizer, or in certain embodiments the delayed release layer can include methacrylic acid copolymer Type B, mono- and diglycerides, dibutyl sebacate and polysorbate 80.

In certain embodiments of the disclosed solid oral pharmaceutical compositions, the sustained release layer includes a water-insoluble and water-permeable polymer and can further include a water-soluble polymer. In certain embodiments, the sustained release layer includes, but is not limited to a cellulose ether derivative, an acrylic resin, a copolymer of acrylic acid and methacrylic acid esters with quaternary ammonium groups, a copolymer of acrylic acid and methacrylic acid esters or a combination of any thereof, or it can include ethyl cellulose, hydroxypropyl cellulose, dibutyl sebacate and a stearate salt such as magnesium stearate. It is understood that the carboxylic acid, sterarate can be associated with various cationic species including mono and divalent metals to produce a nontoxic salt. Such salts can include but are not limited to sodium, potassium, magnesium, zinc, or calcium stearates.

In certain embodiments the core can include a disintegrant and can include corn starch, potato starch, a pre-gelatinized starch, a modified starch, a sweetener, a clay, bentonite, microcrystalline cellulose, carboxymethylcellulose calcium, croscarmellose sodium, alginic acid, sodium alginate, cellulose polyacrilin potassium, an alginate, sodium starch glycolate, a gum, agar, guar, locust bean, karaya, pectin, tragacanth, crospovidone or low substituted hydroxypropyl cellulose. The compositions can also include a disintegrant, osmagent, or a pore-forming agent, which can be a salt, an acid, a base, a chelating agent, sodium chloride, lithium chloride, magnesium chloride, magnesium sulfate, lithium sulfate, polyol, mannitol, sulfatol, xylitol, a carbohydrate, a carbonate, a bicarbonate, electrolyte, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, alpha-hydroxy acids, citric acid, ascorbic acid, or a combination of any thereof. It is a further aspect of the disclosure that the disclosed formulations can include an abuse deterrent agent that can be a nasal irritant such as a capsaicinoid or sodium lauryl sulfate.

In certain embodiments the optional disintegrant, osmagent, or pore-forming agent constitutes from 0 to about 75% of the core by weight. The compositions can also include a swellable layer or a sealing layer disposed between the core and the sustained release layer. The swellable layer can include a superdisintegrant, an osmotic agent, or a combination thereof, and in certain embodiments includes a hydrophilic polymer such as polyethylene oxide and a binder and can further include a drug containing layer between the swellable layer and the sustained release layer and can include a seal between the swellable layer and the drug containing layer.

In certain embodiments the compositions and methods of the present disclosure can be described as a method of treating a condition in a subject with a disorder or condition responsive to the administration of a CNS stimulant, comprising orally administering the disclosed solid, oral pharmaceutical compositions. The method of treatment can include administering a single dosage form or two per day depending on the need of a particular patient. It is an aspect of the compositions and methods of the present disclosure that the administration of the dosage form on a once-a-day basis provides a delayed release of from about 4 to about 12 hours, followed by an increasing plasma concentration profile, which for a 24 hour period commencing with an administration of the dosage form results in a maximum plasma concentration ($C_{max}$) which occurs at least 12 hours, at least 14 hours, or at least 15 hours after administration.

The compositions and methods of the present disclosure can also be described in certain embodiments as solid, oral pharmaceutical compositions including a therapeutic amount of a CNS stimulant wherein the composition, when orally administered to a human, provides a delayed release of from 4 to 12 hours, an ascending plasma concentration of CNS stimulant for a period of from 7 to 12 hours and a maximum plasma concentration ($C_{max}$) from 10 to 19 hours after administration. In certain embodiments, the plasma concentration exhibits a single maximum.

The compositions and methods of the present disclosure can also be described in certain embodiments as solid, oral pharmaceutical compositions comprising a core comprising a therapeutic amount of a CNS stimulant and at least one pharmaceutically acceptable excipient wherein the core is substantially free of a disintegrant, osmagent, or a pore-forming agent; a sustained release layer coating the core; and a delayed release layer enclosing the sustained release layer, wherein when the composition is placed in a simulated gastric environment, the combination of the sustained release and delayed release layers provide: a mean 3 to 12 hour delay during which no more than 10% of the CNS stimulant is released and a mean ascending release of CNS agent from 8-16 hours after being placed in the simulated gastric environment.

Conditions or disorders that can be treated include, but are not limited to ADD, ADHD, excessive daytime sleepiness, major depressive disorder, bipolar depression, negative symptoms in schizophrenia, chronic fatigue, fatigue associated with chemotherapy or binge eating disorder. Attention deficit disorders are characterized by hyperactive, impulsive or inattentive symptoms that cause impairment in social, academic, or occupational functioning, and are often present in two or more settings, school (or work) and at home, for example. For the Inattentive Type, at least 6 of the following symptoms have persisted for at least 6 months: lack of attention to details/careless mistakes; lack of sustained attention; poor listener; failure to follow through on tasks; poor organization; avoids tasks requiring sustained mental effort; loses things; easily distracted; and forgetful. For the Hyperactive-Impulsive Type, at least 6 of the following symptoms have persisted for at least 6 months: fidgeting/squirming; leaving seat; inappropriate running/climbing; difficulty with quiet activities; "on the go"; excessive talking; blurting answers; can't wait turn, and intrusive behavior. The combined type includes both inattentive and hyperactive-impulsive behaviors.

It is understood that the term "treatment" as used herein is not limited to the cure or elimination of any condition or disorder nor is that term limited to the achievement of certain milestones or improvement criteria in a particular subject, but includes the administration of an agent for the purpose of achieving positive effects in terms of cognitive or behavioral function, reduction of symptoms or side effects. All such activities are considered to be treatment whether or not any improvement is immediately observable or measureable.

It is well known, for example, that certain side effects may occur in conjunction with administration of CNS stimulants. It is also known that these side effects can be related to the blood concentrations of stimulants in particular patients. These side effects can include, but are not limited to headache, nausea, dizziness, hot flush, decreased appetite, insomnia, abdominal discomfort (stomach ache), dry mouth, fast heartbeat, nervousness, mood swings, irritability, weight loss, or complaints of just not feeling good, with the most significant often being sleep or appetite related complaints. It is contemplated that treatment with the disclosed formulations will result in reduced incidence or severity of side effects relative to treatments in which the active agent is rapidly released in the stomach. As such, treatment would encompass not only reduction of symptoms of the condition or disorder but also reduction in side effects.

The compositions and active agents of this disclosure are administered in an "effective amount," "effective dose," or "therapeutically effective amount or dose." By an "effective" amount or a "therapeutically effective amount" or dose of a drug or pharmacologically active agent is meant a nontoxic but sufficient amount of the drug or agent to provide the desired effect. In the current disclosure, an "effective amount" is the amount of that composition or active agent that is effective to improve, ameliorate or prevent one or more symptoms of the condition being treated. The amount that is "effective" will vary from subject to subject, depending on the age, weight and general condition of the individual, or the particular active agent. A therapeutic or effective dose or amount is determined by a physician and is often based on empirical data obtained by administering increasing doses until the best balance of benefit vs. side effects is reached.

An effective dose in the compositions of the present disclosure, particular for treatment of ADHD include doses shown to be effective in the treatment of those conditions by oral dosage, including but not limited to 5, 9, 10, 15, 18, 20, 25, 27, 30, 35, 36, 45 or 54 mg once or twice daily, or the bioequivalent of such doses of the same active ingredient in an immediate release formulation. As such, the effective dose can be 60, 65, 70, 75, 80, 85, 90, 100 or up to 150 mg once or twice a day. It is also understood that other dosage ranges may be effective for conditions or symptoms other than ADHD and as such, the therapeutically effective drug concentration in the disclosed compositions can be from 0.1 to 1000 mg inclusive of any particular concentration within that range.

As used herein, the term "pharmaceutically acceptable salt" refers to nontoxic pharmaceutically acceptable salts as described (Ref. International J. Pharm., 1986, 33, 201-217; J. Pharm. Sci., 1997 (January), 86, 1, 1). Other salts well known to those in the art may, however, be useful in the preparation of compositions of the disclosure including, but not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The compositions and methods of the present disclosure can also be described in certain embodiments as solid, oral pharmaceutical compositions comprising a therapeutic amount of a CNS stimulant wherein the composition, when orally administered to a human, provides a delayed release of from 3-8 hours, an ascending rate of release of CNS stimulant for a period of from 7-12 hours and a maximum plasma concentration ($C_{max}$) from 10-16 hours after administration, and wherein a plot of the plasma concentration versus time after release can exhibit a single maximum, rather than two or more pulses of drug release. The solid oral pharmaceutical can be further defined as one in which no more than 10% of the CNS stimulant is released within 6 hours after administration.

In certain embodiments the compositions and methods of the present disclosure can be defined as solid, oral pharmaceutical compositions comprising: a core comprising a therapeutic amount of a CNS stimulant and at least one pharmaceutically acceptable excipient, a sustained release layer coating the core, and a delayed release layer enclosing the sustained release layer, wherein the core is substantially free of a disintegrant, osmagent, or a pore-forming agent; wherein when the composition is administered to a human, the combination of the sustained release and delayed release layers provide: a mean 3-8 hour delay during which no more than 10% of the CNS stimulant is released; a mean ascending plasma concentration of CNS agent from the onset of absorption to a period of from 12-16 hours after administration and in which the plasma concentration exhibits a single maximum.

The present disclosure can be described therefore in certain embodiments as a solid, oral pharmaceutical composition including a single population of beads, with beads including a core comprising methylphenidate or a pharmaceutical salt thereof and at least one pharmaceutically acceptable excipient, a sustained release layer enclosing the core; and a delayed release layer enclosing the sustained release layer. The sustained release layer can be a layer that releases the drug in a sigmoidal release curve in which a slow initial release period is followed by a period of more rapid release. Such a release pattern will also include an inflection point in which the rate of release decreases somewhere in the intermediate period between start of release and total release. This point can be most clearly determined by a "Hill Plot", or a plot of the first derivative of the release profile. The inflexion point is defined as the point at which the Hill plot transitions from a positive slope to a negative slope.

The oral formulation can be administered to a human subject in a fasted state resulting in a pharmacokinetic profile which includes a lag of at least 7 hours during which the plasma concentration of methylphenidate is less than 5% of the maximum plasma concentration (Cmax), a plasma area under the curve at 10 hours ($AUC_{0-10}$) after administration that is less than about 7% of $AUC_{0-48}$, and wherein the time to $C_{max}$ ($T_{max}$) is between 12 and 19 hours after administration. The described administration to a population of subjects also provides a significant improvement in ADHD related behavior or cognitive ability over a period of at least 12 continuous hours as measured by a validated rating scale. The meaning of a validated rating scale is described in more detail below.

In the practice of the disclosure, the improvement can be measured by the ADHD-RS-IV scale, BSFQ, CGI, CGI-P, PREMB, Permanent Product Measure of Performance (PERMP) scores, or SKAMP rating scale, for example, or by any validated rating scale as defined herein or known to those of skill in the art. It is an aspect of the disclosure that the formulation provides a significant improvement in Permanent Product Measure of Performance scores over a period of at least about 12 continuous hours when administered to a population of patients including adult, adolescent or child subjects. Administration of the disclosed compositions also provides a significant improvement over placebo in Permanent Product Measure of Performance scores over a period from about 11 through about 23 hours post-dose. For example, when the formulation is administered at about 8-10 PM, the formulation provides a significant improvement in PERMP scores during a 10-12 hour period from about 7 AM to about 9 PM the following day, and can include at least a 50% improvement over placebo.

As described herein, the formulation can also provide a significant improvement in SKAMP scores during a period of about 12 continuous hours and the improvement can be during a period from about 11 through about 23 hours post-dose. For example, when the formulation is administered at about 8-10 PM, it provides a significant improvement in SKAMP scores during a 10-12 hour period from about 7 AM to about 9 PM the following day.

The disclosed compositions also can provide a measureable improvement in early morning performance and control of symptoms of ADHD as measured by BSFQ scores over placebo when the composition is administered at about 8-10 PM. As described elsewhere herein, much of the disclosure is written in reference to treatment of attention deficit disorders, but the compositions and methods as described herein are not limited to a preferred embodiment, but can be used in the treatment of attention deficit disorder, attention deficit hyperactivity disorder, excessive daytime sleepiness, major depressive disorder, bipolar depression, negative symptoms in schizophrenia, chronic fatigue, fatigue associated with chemotherapy or binge eating disorder, for example, or for other conditions that respond to a CNS stimulant.

BRIEF DESCRIPTION OF THE DRAWINGS

The following drawings form part of the present specification and are included to further demonstrate certain aspects of the present inventions. The disclosure can be better understood by reference to one or more of these drawings in combination with the detailed description of specific embodiments presented herein.

DETAILED DESCRIPTION OF THE INVENTION

Figure 1A:
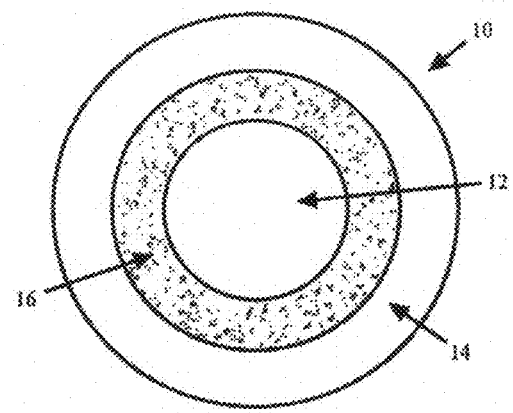
FIG. 1A is a schematic representation of a bead pharmaceutical composition with a drug containing core surrounded by a sustained release layer and a delayed release layer.

The present disclosure provides therapeutic compositions and methods for treatment of attention deficit disorder (ADD), attention deficit hyperactivity disorder (ADHD) or other conditions or disorders responsive to CNS stimulants by providing dosage forms that deliver a therapeutic amount of active drug in a delayed and controlled release pattern in order to maintain a therapeutic amount of drug through the active portion of the day. For pediatric patients including adolescents and also for adults, a therapeutic amount is desirable upon arising and throughout the morning, as well as through the afternoon hours in which work or homework needs to be done.

The disclosed formulations can provide a therapeutic amount of drug during extended periods of the day with a single administration. The dosage forms provide a delayed release such that the dosage form can be administered conveniently prior to the patient's sleeping. A small percentage of the drug can be released over the first 6-hours after administration such that the patient has already received a minimal therapeutic dose at the normal awakening time. The patient thus does not need to be awakened, given a pill, and then required to have breakfast and prepare for their day prior to experiencing a therapeutic effect.

The present disclosure can be described, therefore, as a method of treating a condition in a subject with a disorder or condition responsive to the administration of a methylphenidate, comprising orally administering an effective amount of methylphenidate or a pharmaceutical salt thereof in a formulation that when administered to said subject provides: (i) a lag period of at least 5 hours during which the plasma concentration of methylphenidate is less than 10% of the maximum concentration ($C_{max}$); (ii) a plasma area under the curve at 10 hours ($AUC_{0-10}$) after administration that is less than about 7% of $AUC_{0-48}$; and (iii) wherein the time to $C_{max}$ ($T_{max}$) is between 12 and 19 hours after administration and wherein administration to a population of subjects provides a significant improvement in ADHD related behavior or ability over a period of at least 12 continuous hours as measured by a validated rating scale. As used herein a validated rating scale is a scale, score or combined score that is validated or published in a peer reviewed journal, or is recognized as valid by those of skill in the art, or considered by a pharmaceutical regulatory agency such as the U.S. Food and Drug Administration or the European Medicines Agency, for example, as providing a valid measure of therapeutic efficacy.

The validated rating scale, score or combined score as used herein includes methods that are recognized by a government pharmaceutical regulatory agency, are published and/or relied upon in a peer reviewed journal, or in a clinical trial reported in a peer-reviewed journal or are endorsed by an association of physicians or clinicians. Examples of such methods or measurements include, but are not limited to the ADHD-RS-IV scale based on the Diagnostic and Statistical Manual of Mental Disorders, Fourth Edition criteria, the Before School Functioning Questionnaire (BSFQ), Clinical Global Impression (CGI), Clinical Global Impression of Improvement (CGI-I), Clinical Global Impresssion of Severity (CGI-S), Conors Global Index Parent (CGI-P), Diagnostic and Statistical Manual of Mental Disorders-Fourth Edition Text Revision (DSM-IV-TR), Parents Rating of Evening and Morning Behavior Revised (PREMB-R), Permanent Product Measure of Performance (PERMP) scores, Swanson, Kotkin, Agler, M-Flynn and Pelham (SKAMP) rating scale, or SKAMP-CS combined score.

The disclosure can be described in certain embodiments as a method in which when the formulation is administered to a population of adult, adolescent or pediatric subjects, the formulation provides a significant improvement over placebo in Permanent Product Measure of Performance scores over a period of at least about 12 continuous hours, the formulation provides a significant improvement over placebo in Permanent Product Measure of Performance scores over a period from about 11 through about 23 hours post-dose, or when the formulation is administered at about 8-10 PM, the formulation provides a significant improvement in PERMP scores during a 10-12 hour period from about 7 AM to about 9 PM the following day. In certain embodiments the significant improvement is at least a 50% improvement over placebo at each hour for a period of 12 hours.

The disclosure can also be described in certain embodiments as a method in which when the formulation is administered to a population of adolescent or child subjects, the formulation provides a significant improvement in SKAMP scores during a period of about 12 continuous hours and where the formulation provides a significant improvement in SKAMP scores during a period from about 11 through about 23 hours post-dose, or wherein when the formulation is administered at about 8-10 PM, the formulation provides a significant improvement in SKAMP scores during a 10-12 hour period from about 7 AM to about 9 PM the following day.

The present disclosure can also be described in certain embodiments as a method of treating attention deficit disorder or attention deficit hyperactivity disorder in a subject comprising orally administering to the subject a unit dose of methylphenidate or a pharmaceutical salt thereof in a unit dose that comprises a sustained release formulation comprising the methylphenidate or a pharmaceutical salt thereof enclosed in an outer coating that is insoluble in an aqueous medium at pH below 5.5, wherein the unit dose provides a lag period of at least 5 hours during which the subject's plasma concentration of methylphenidate or is less than 10% of the maximum concentration ($C_{max}$), wherein the plasma area under the curve at 10 hours ($AUC_{0-10}$) after administration is less than about 7% of $AUC_{0-48}$, wherein the time to $C_{max}$ ($T_{max}$) is between 12 and 19 hours after administration, and wherein administration to a population of subjects provides a significant improvement in ADHD related behavior or cognitive ability over a period of at least 12 continuous hours.

The validated rating scale, score or combined score as used herein includes methods that are recognized by a government pharmaceutical regulatory agency, are published and/or relied upon in a peer reviewed journal, or in a clinical trial reported in a peer-reviewed journal or are endorsed by an association of physicians or clinicians. Examples of such methods or measurements include, but are not limited to the ADHD-RS-IV scale based on the Diagnostic and Statistical Manual of Mental Disorders, Fourth Edition criteria, the Before School Functioning Questionnaire (BSFQ), Clinical Global Impression (CGI), Clinical Global Impression of Improvement (CGI-I), Clinical Global Impresssion of Severity (CGI-S), Conors Global Index Parent (CGI-P), Diagnostic and Statistical Manual of Mental Disorders-Fourth Edition Text Revision (DSM-IV-TR), Parents Rating of Evening and Morning Behavior Revised (PREMB-R), Permanent Product Measure of Performance (PERMP) scores, Swanson, Kotkin, Agler, M-Flynn and Pelham (SKAMP) rating scale, or SKAMP-CS combined score.

The disclosure can be described in certain embodiments as a method in which when the formulation is administered to a population of adult, adolescent or pediatric subjects, the formulation provides a significant improvement over placebo in Permanent Product Measure of Performance scores over a period of at least about 12 continuous hours, the formulation provides a significant improvement over placebo in Permanent Product Measure of Performance scores over a period from about 11 through about 23 hours post-dose, or when the formulation is administered at about 8-10 PM, the formulation provides a significant improvement in PERMP scores during a 10-12 hour period from about 7 AM to about 9 PM the following day. In certain embodiments the significant improvement is at least a 50% improvement over placebo at each hour for a period of 12 hours.

The disclosure can also be described in certain embodiments as a method in which when the formulation is administered to a population of adolescent or child subjects, the formulation provides a significant improvement in SKAMP scores during a period of about 12 continuous hours and where the formulation provides a significant improvement in SKAMP scores during a period from about 11 through about 23 hours post-dose, or wherein when the formulation is administered at about 8-10 PM, the formulation provides a significant improvement in SKAMP scores during a 10-12 hour period from about 7 AM to about 9 PM the following day.

The formulations disclosed herein also provide an ascending release of the drug over the next 8-16 hours or so after the delay period, or up to 16 hours after administration of the dosage forms. The dosage forms thus can provide a delayed release followed by a sigmoidal release curve as shown in the accompanying drawings, FIG. 5.

CNS Stimulants

Stimulant medications (e.g., methylphenidate and amphetamines and prodrugs) are often prescribed to treat individuals diagnosed with ADHD. According to the National Institute of Health, all stimulants work by increasing dopamine levels in the brain. Dopamine is a brain chemical (or neurotransmitter) associated with pleasure, movement, and attention. The therapeutic effect of stimulants is achieved by slow and steady increases of dopamine, which are similar to the natural production by the brain. The doses prescribed by physicians start low and increase gradually until a therapeutic effect is reached.

Treatment of ADHD with stimulants, often in conjunction with psychotherapy, helps to improve the symptoms of ADHD, as well as the self-esteem, cognition, and social and family interactions of the patient. The most commonly prescribed medications include amphetamines and methylphenidate. These medications have a paradoxically calming and "focusing" effect on individuals with ADHD. Researchers speculate that because methylphenidate amplifies the release of dopamine, it can improve attention and focus in individuals who have dopamine signals that are weak.

Amphetamines that are useful in the disclosed formulations and methods include amphetamine and its isomers such as dextroamphetamine, d,l amphetamines and their pharmaceutically acceptable salts, such as sulfate, saccharate, and aspartate salts, for example. Amphetamines are non-catecholamine, sympathomimetic amines with CNS stimulant activity. Peripheral actions include elevations of systolic and diastolic blood pressures and weak bronchodilator and respiratory stimulant action.

Dextroamphetamine is the dextro isomer of the compound d,l-amphetamine sulfate, a sympathomimetic amine of the amphetamine group. Chemically, dextroamphetamine is d-alpha-methylphenethylamine. Dextroamphetamine can be used in the practice of the present disclosure, or various pharmaceutically acceptable salts of dextroamphetamine can be used.

Methylphenidate

Methylphenidate is another CNS (CNS) stimulant that was approved by the FDA in 1955 for the hypeactivity. Methylphenidate can be prescribed in a racemic mix of dextro and levo conformations or as the pure dextro isomer. Methylphenidate has two chiral centers in the molecule and thus can also be further refined to enrich the d threo isomer. The use of pharmaceutically acceptable salts of methylphenidate, such as methylphenidate hydrochloride is also contemplated by the present disclosure.

It is understood that the active pharmaceutical ingredients of the present disclosure can be present as prodrugs that are activated in the body of a user. One form of prodrug has an amino acid conjugated to the active ingredient. When the amino acid is enzymatically cleaved, the active drug is released. Prodrugs comprising a lysyl, isoleucyl or aspartyl conjugate are contemplated to be useful in the practice of the present disclosure.

Formulations

The formulations of the disclosure are designed to provide novel release and plasma profiles that include a first lag phase followed by a sigmoidal release phase. By providing this profile, the dosage forms provide a timed, prolonged therapeutic effect when taken once a day. Based on the release characteristics, in which the dosage form passes through the stomach prior to release, the formulations disclosed herein provide at least the following further advantages: low variability in gastric emptying, low risk of sudden dose dumping, low incidence of gastric discomfort and low intra- and inter-individual variability.

A first example of a dosage form is a single population of beads that can be administered in a capsule or a liquid or gel suspension containing the beads. An example of a bead structure 10 is shown in schematic form in FIG. 1A-B. In FIG. 1A, the inner circle represents a drug containing core, which includes the active ingredient or prodrug, the appropriate excipients and optionally a superdisintegrant or osmagent. A core can include, for example, an active agent, a disintegrant, osmagent, or pore-forming agent, and a binder. An exemplary core includes about 20-25% active agent, about 45-60% microcrystalline cellulose, about 10-30% potassium chloride and about 3-5% binder such as polyvinyl pyrrolidone or hydroxypropyl cellulose, for example. The drug containing core can be made by a variety of processes known in the art, including wet granulation, extrusion, and spheronization. In this embodiment, two layers cover the core. The first layer is a sustained release layer and the outer layer is a delayed release layer that is optionally pH dependent. In certain embodiments, the core as shown in FIG. 1A can be an inert non-pareil bead. The inner core is a bead of sugar and starch or it can be composed of microcrystalline cellulose. Any spherical bead that is suitable for forming the core bead and is pharmaceutically acceptable can be used. In such embodiments, the drug and excipients of the core are layered onto the core bead, providing a three layer formulation.

The outermost layer 14 is a delayed release or an enteric coating. In certain embodiments this layer comprises a water-soluble polymer, a water-insoluble polymer, a plasticizer and a lubricant. The time of delay of drug release is controlled by the ratio of water-soluble and insoluble polymers, the plasticizer concentration, amount of lubricant, and the coating weight gain, which can be up to 35-45%. Alternatively this layer is a pH dependent polymer that dissolves at pH above 5.5.

A sustained release layer 16 is designed to provide a slower initial rate of release that increases over a period of up to 8-10 hours after the layer is exposed to an aqueous environment. The increasing drug profile can be achieved by a membrane that becomes more permeable over time. An example of a sustained release layer includes a water-soluble polymer, a water-insoluble polymer, a plasticizer and a lubricant. The rate of drug release can be controlled or sustained by varying the ratio of water-soluble and water-insoluble polymers and by varying the coating thickness up to 15-45% weight gain.

Figure 1B:
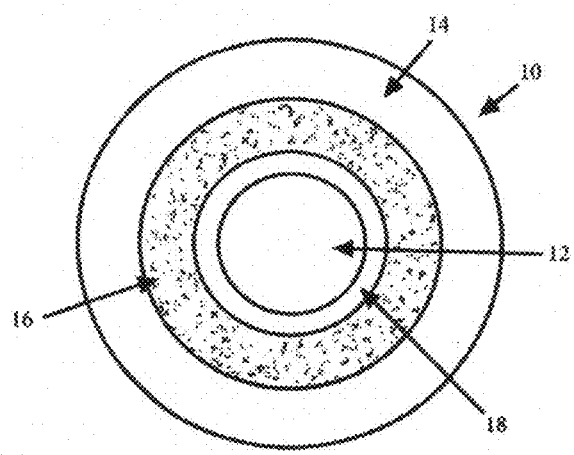
FIG. 1B a composition as in 1A with an added swellable layer disposed between the sustained release layer and the drug containing core.

An alternative embodiment is shown in FIG. 1B. In this figure, a swellable layer 18, including a superdisintegrant or osmotic agent is disposed between the core and the sustained release layer.

Figure 3:
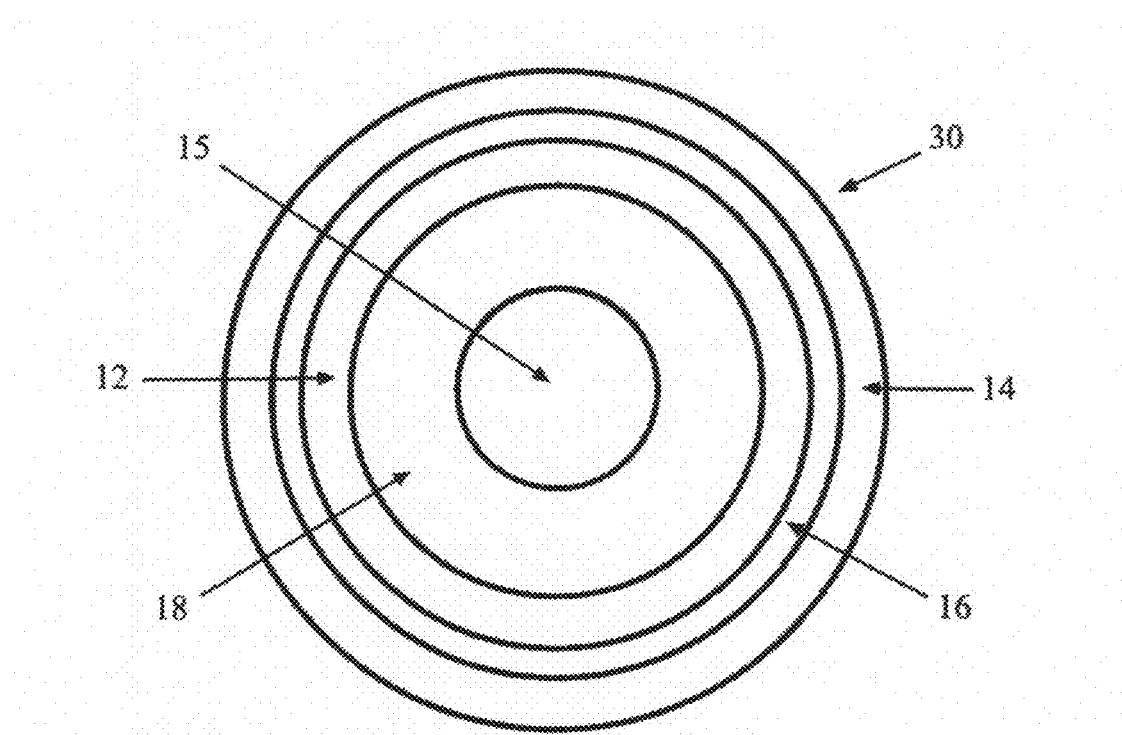
FIG. 3 is a schematic representation of a bead pharmaceutical composition that includes a core surrounded by 4 layers, an inert inner core, a swelling polymer, a drug layer, a sustained release layer and an enteric layer.

In certain embodiments, the compositions and methods of the present disclosure include a formulation of 4 layers 30 as shown in FIG. 3. This formulation can include an inner core 15 of a non-pareil bead and 4 concentric layers from inner to outer described as, a swelling polymer layer 18, drug layer 12, a sustained release layer 16 and a pH dependent delayed release layer 14, which can be a pH dependent layer.

In certain embodiments, the 4 layer composition can be made in a step-wise fashion. In the first step, a hydrophilic polymer suspended in ethanol with a binder is coated onto nonpareil beads to a 30-50% weight gain. In certain embodiments PolyOx Coagulant SFP (PEO) marketed by the Dow Chemical Company is the hydrophilic polymer and hydroxypropyl cellulose (HPC LF) is added as the binder. The PolyOx layer is then sealed with a hydroxypropyl cellulose such as Klucel® EF to a 10% weight gain. The active pharmaceutical ingredient (API) is then suspended in ethanol with a binder and coated onto the layered bead and the sustained release and delayed release coatings are applied as described herein.

Figure 2A:
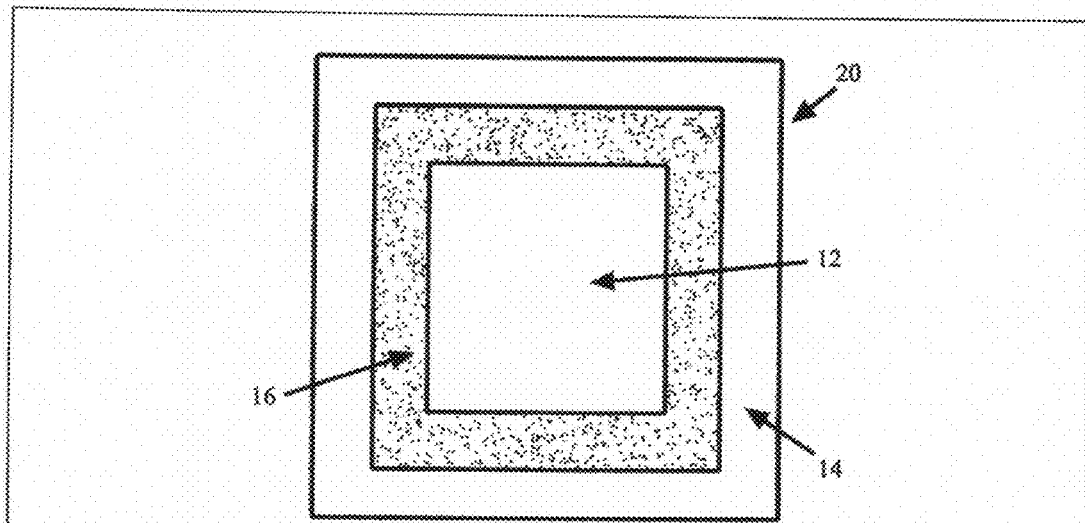
FIG. 2A is a schematic representation of a minitablet pharmaceutical composition with a drug containing core surrounded by a sustained release layer and a delayed release layer.
Figure 2B:
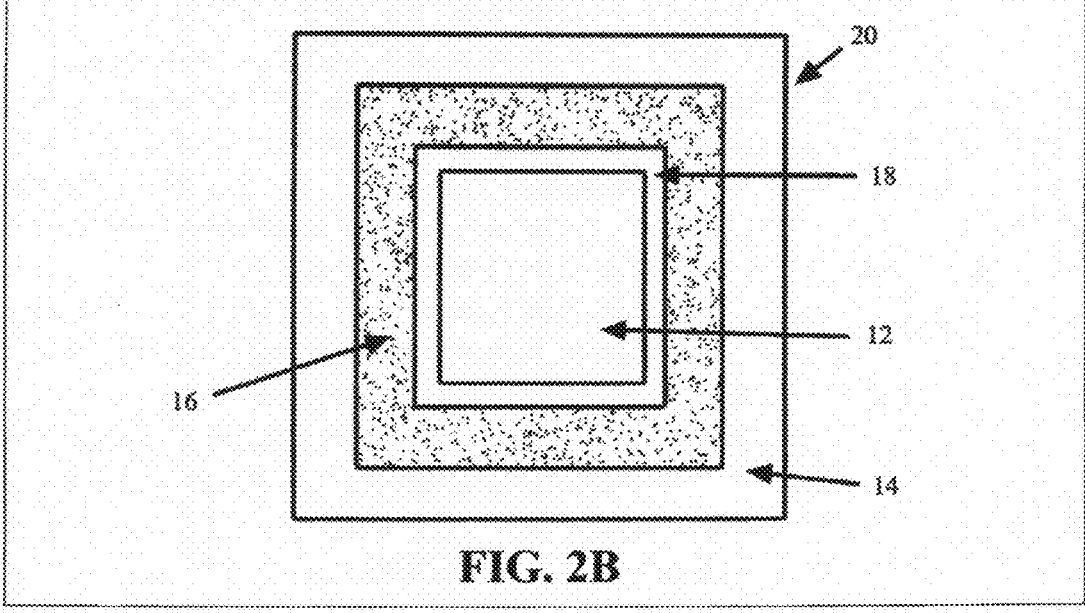
FIG. 2B a composition as in 2A with an added swellable layer disposed between the sustained release layer and the drug containing core.

FIGS. 2A-B represent embodiments in which the core is a minitablet 20 rather than a bead. The core and layers in FIGS. 2A and B are functionally the same as the like numbered layers on the beads in FIG. 1A-B, except there is no optional inert core.

Various water-soluble polymers can be used in the disclosed formulations. Such polymers include, but are not limited to polyethylene oxide (PEO), ethylene oxide-propylene oxide co-polymers, polyethylene-polypropylene glycol (e.g. poloxamer), carbomer, polycarbophil, chitosan, polyvinyl pyrrolidone (PVP), polyvinyl alcohol (PVA), hydroxyalkyl celluloses such as hydroxypropyl cellulose (HPC), hydroxyethyl cellulose, hydroxymethyl cellulose and hydroxypropyl methylcellulose, sodium carboxymethyl cellulose, methylcellulose, hydroxyethyl methylcellulose, hydroxypropyl methylcellulose, polyacrylates such as carbomer, polyacrylamides, polymethacrylamides, polyphosphazines, polyoxazolidines, polyhydroxyalkylcarboxylic acids, alginic acid and its derivatives such as carrageenate alginates, ammonium alginate and sodium alginate, starch and starch derivatives, polysaccharides, carboxypolymethylene, polyethylene glycol, natural gums such as gum guar, gum acacia, gum tragacanth, karaya gum and gum xanthan, povidone, gelatin or the like.

In certain embodiments, at least the delayed release layer includes one or more polymers such as an acrylic polymer, acrylic copolymer, methacrylic polymer or methacrylic copolymer, including but not limited to Eudragit® L100, Eudragit® L100-55, Eudragit® L 30 D-55, Eudragit® S100, Eudragit® 4135F, Eudragit® RS, acrylic acid and methacrylic acid copolymers, methyl methacrylate, methyl methacrylate copolymers, ethoxyethyl methacrylates, cyanoethyl methacrylate, aminoalkyl methacrylate copolymer, polyacrylic acid, polymethacrylic acid, methacrylic acid alkylamine copolymer, polymethyl methacrylate, polymethacrylic acid anhydride, polymethacrylate, polyacrylamide, polymethacrylic acid anhydride and glycidyl methacrylate copolymers, an alkylcellulose such as ethylcellulose, methylcellulose, calcium carboxymethyl cellulose, certain substituted cellulose polymers such as hydroxypropyl methylcellulose phthalate, and hydroxypropyl methylcellulose acetate succinate, cellulose acetate butyrate, cellulose acetate phthalate, and cellulose acetate trimaleate, polyvinyl acetate phthalate, polyester, waxes, shellac, zein, or the like.

Eudragits are well known polymers and copolymers useful for controlled release applications. The EUDRAGIT® grades for enteric coatings are based on anionic polymers of methacrylic acid and methacrylates. They contain —COOH as a functional group. They dissolve at ranges from pH 5.5 to pH 7. EUDRAGIT® FS 30 D is the aqueous dispersion of an anionic copolymer based on methyl acrylate, methyl methacrylate and methacrylic acid. It is insoluble in acidic media, but dissolves by salt formation above pH 7.0. Eudragit L100-55 and L30-55 dissolve at pH above 5.5. Eudragit L100 and S100 dissolve at pH above 6.0.

Sustained-release EUDRAGIT® formulations are employed for many oral dosage forms to enable time-controlled release of active ingredients. Drug delivery can be controlled throughout the whole gastro-intestinal tract for increased therapeutic effect and patient compliance. Different polymer combinations of EUDRAGIT® RL (readily permeable) and RS (sparingly permeable) grades allow custom-tailored release profiles and enable a wide range of alternatives to achieve the desired drug delivery performance. The EUDRAGIT® NE polymer is a neutral ester dispersion which requires no plasticizer and is particularly suitable for granulation processes in the manufacture of matrix tablets and sustained release coatings.

Exemplary osmagents or osmotic agents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art.

As used herein, the term "disintegrant" is intended to mean a compound used in solid dosage forms to promote the disruption of a solid mass (layer) into smaller particles that are more readily dispersed or dissolved. Exemplary disintegrants include, by way of example and without limitation, starches such as corn starch, potato starch, pre-gelatinized and modified starches thereof, sweeteners, clays, bentonite, microcrystalline cellulose (e.g., Avicel™), carboxymethylcellulose calcium, croscarmellose sodium, alginic acid, sodium alginate, cellulose polyacrilin potassium (e.g., Amberlite™), alginates, sodium starch glycolate, gums, agar, guar, locust bean, karaya, pectin, tragacanth, crospovidone and other materials known to one of ordinary skill in the art. A superdisintegrant is a rapidly acting disintegrant. Exemplary superdisintegrants include crospovidone and low substituted HPC.

In preferred embodiments, a plasticizer is also included in the oral dosage form. Plasticizers suitable for use in the present invention include, but are not limited to, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, acetyl triethyl citrate, tributyl citrate and allyl glycolate.

It is an aspect of the compositions and methods of the present disclosure that the formulations or dosage forms can also incorporate one or more ingredients that discourage or prevent abuse of the active ingredients by crushing and inhaling a powdered form of the formulations. As such, a nasal irritant can be included, either as a separate layer, or incorporated into an outer layer, a sustained release layer or the core of the dosage forms. Exemplary irritants include, but are not limited to sodium lauryl sulfate, which is also called sodium dodecyl sulfate or capsaicinoids including capsaicin and synthetic capsaicins. In certain embodiments, the dosage forms include from 1% to 10% sodium lauryl sulfate.

The compositions of the present disclosure can also include one or more functional excipients such as lubricants, thermal lubricants, antioxidants, buffering agents, alkalinizing agents, binders, diluents, sweeteners, chelating agents, colorants, flavorants, surfactants, solubilizers, wetting agents, stabilizers, hydrophilic polymers, hydrophobic polymers, waxes, lipophilic materials, absorption enhancers, preservatives, absorbents, cross-linking agents, bioadhesive polymers, retardants, pore formers, and fragrance.

Lubricants or thermal lubricants useful in the present invention include, but are not limited to fatty esters, glyceryl monooleate, glyceryl monostearate, wax, carnauba wax, beeswax, vitamin E succinate, and a combination thereof.

As used herein, the term "antioxidant" is intended to mean an agent that inhibits oxidation and thus is used to prevent the deterioration of preparations by oxidation due to the presence of oxygen free radicals or free metals in the composition. Such compounds include, by way of example and without limitation, ascorbic acid, ascorbyl palmitate, butylated hydroxyanisole (BHA), butylated hydroxytoluene (BHT), hypophophorous acid, monothioglycerol, sodium ascorbate, sodium formaldehyde sulfoxylate and sodium metabisulfite and others known to those of ordinary skill in the art. Other suitable antioxidants include, for example, vitamin C, sodium bisulfite, vitamin E and its derivatives, propyl gallate or a sulfite derivative.

Binders suitable for use in the present invention include beeswax, carnauba wax, cetyl palmitate, glycerol behenate, glyceryl monostearate, glyceryl palmitostearate, glyceryl stearate, hydrogenated castor oil, microcrystalline wax, paraffin wax, stearic acid, stearic alcohol, stearate 6000 WL1644, gelucire 50/13, poloxamer 188, and polyethylene glycol (PEG) 2000, 3000, 6000, 8000, 10000 or 20000.

A buffering agent is used to resist change in pH upon dilution or addition of acid or alkali. Such compounds include, by way of example and without limitation, potassium metaphosphate, potassium phosphate, monobasic sodium acetate and sodium citrate anhydrous and dihydrate, salts of inorganic or organic acids, salts of inorganic or organic bases, and others known to those of ordinary skill in the art, As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

Exemplary binders include: polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcelluloses and cellulosic derivatives such as low substituted HPC (L-HPC), methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; PLA and PLGA, polyesters (shellac), wax such as carnauba wax, beeswax; polysaccharides such as cellulose, tragacanth, gum arabic, guar gum, and xanthan gum.

Exemplary chelating agents include EDTA and its salts, alphahydroxy acids such as citric acid, polycarboxylic acids, polyamines, derivatives thereof, and others known to those of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors that have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particular flavors are the grape and cherry flavors and citrus flavors such as orange.

Suitable surfactants include Polysorbate 80, sorbitan monooleate, polyoxymer, sodium lauryl sulfate or others known in the art. Soaps and synthetic detergents may be employed as surfactants. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

A wetting agent is an agent that decreases the surface tension of a liquid. Wetting agents would include alcohols, glycerin, proteins, peptides water miscible solvents such as glycols, hydrophilic polymers Polysorbate 80, sorbitan monooleate, sodium lauryl sulfate, fatty acid alkali metal, ammonium, and triethanolamine salts, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

Solubilizers include cyclodextrins, povidone, combinations thereof, and others known to those of ordinary skill in the art.

Exemplary waxes include carnauba wax, beeswax, microcrystalline wax and others known to one of ordinary skill in the art.

Exemplary absorption enhancers include dimethyl sulfoxide, Vitamin E PGS, sodium cholate and others known to one of ordinary skill in the art.

Preservatives include compounds used to prevent the groweighth of microorganisms. Suitable preservatives include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and others known to those of ordinary skill in the art.

Examples of absorbents include sodium starch glycolate (Explotab™, Primojel™) and croscarmellose sodium (Ac-Di-Sol™), cross-linked PVP (Polyplasdone™ XL 10), veegum, clays, alginates, PVP, alginic acid, carboxymethylcellulose calcium, microcrystalline cellulose (e.g., Avicel™), polacrillin potassium (e.g., Amberlite™), sodium alginate, corn starch, potato starch, pregelatinized starch, modified starch, cellulosic agents, montmorrilonite clays (e.g., bentonite), gums, agar, locust bean gum, gum karaya, pectin, tragacanth, and other disintegrants known in to those of ordinary skill in the art.

A cross-linking agent is defined as any compound that will form cross-links between the moieties of the polymer. A cross-linking agent can include, by way of example and without limitation, an organic acid, an alpha-hydroxy acid, and a beta-hydroxy acid. Suitable cross-linking agents include tartaric acid, citric acid, fumaric acid, succinic acid and others known to those of ordinary skill in the art.

Bioadhesive polymers include polyethylene oxide, KLUCEL (hydroxypropylcellulose), CARBOPOL, polycarbophil, GANTREZ, Poloxamer, and combinations thereof, and others known to one of ordinary skill in the art.

Retardants are agents that are insoluble or slightly soluble polymers with a glass transition temperature (Tg) above 45° C., or above 50° C. before being plasticized by other agents in the formulation including other polymers and other excipients needed for processing. The excipients include waxes, acrylics, cellulosics, lipids, proteins, glycols, and the like.

Exemplary pore formers include water-soluble polymers such as polyethylene glycol, propylene glycol, polaxamer and povidone; binders such as lactose, calcium sulfate, calcium phosphate and the like; salts such as sodium chloride, magnesium chloride and the like; combinations thereof and other similar or equivalent materials which are widely known in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol, sucrose, fructose and other such materials known to those of ordinary skill in the art.

It should be understood that compounds used in the art of pharmaceutical formulation generally serve a variety of functions or purposes. Thus, if a compound named herein is mentioned only once or is used to define more than one term herein, its purpose or function should not be construed as being limited solely to that or those named purpose(s) or function(s).

It is an aspect of the compositions and methods of the present disclosure that the disclosed pharmaceutical formulations provide novel release profiles in vivo and when orally administered to a human. The formulations provide a lag time of from 4-12 hours in certain embodiments followed by release of 85% of the drug over the following 9 hours in an ascending dose.

The dissolution profile is performed in conditions designed to mimic the gastric environment, or the environment that is encountered by an oral composition that is swallowed by a human. Although residence time in the stomach varies, a typical test places the composition in the low pH solution of 0.1N HCl for two hours to mimic the residence time in stomach acid. The composition is then placed in a higher pH aqueous solution, about pH 6 for 2-6 hours followed by typically pH 6.8 to mimic the environment of the ileum and colon. As used herein, simulated gastric conditions encompasses both the acidic first stage and the subsequent higher pH stages of a normal human gastrointestinal tract.

Following the delay period, the plasma concentration increases over approximately 9-10 hours to a reach a maximum plasma concentration ($C_{max}$). Based on this release profile, a dose taken at 9:00 P.M with a 6 hour delay begins to release the drug at about 3 A.M. and the maximum plasma concentration is reached about 16 hours later.

It is a further aspect of the compositions and methods of the present disclosure that the drug can begin to be slowly released during the lag time. This release is determined by the composition of the delayed release layer as described herein. Some examples of a small release during the lag time are those in which no more than about 10% of the drug is released during the 3-12 hour lag. It is also understood that a greater percentage, 12%, 15%, 18% or even 20%, can be released as the delayed release layer becomes more permeable.

Disclosed herein, therefore, are pharmaceutical preparations for once daily administration of a CNS stimulant for treatment of conditions that respond to such drugs, such as ADD, ADHD, bipolar depression, narcolepsy, sleeping disorders, and fatigue. The dosage is formulated to be taken prior to going bed and starts to release after a lag of several hours so the patient has absorbed a sufficient amount of drug to have a therapeutic effect while awakening and preparing to leave for work or school. It is a further aspect of the formulations that the drug is released in an ascending dose through the day to overcome any acute tolerance effect and maintain a therapeutic level of drug.

An embodiment of the compositions and methods of the present disclosure is a dosage form that includes a capsule enclosing a single population of beads or minitablets that include a core and 2 or more coatings surrounding the core. The inner core is a bead or minitablet containing an API and one or more excipients. The core is enclosed in a sustained release layer, and an outer, delayed release layer.

In certain embodiments the sustained release layer includes a combination of water-soluble polymers and water-insoluble polymers. The sustained release coating can contain a combination of polyethylene oxide and an ethylcellulose, for example, or a hydroxypropylmethyl cellulose and ethylcellulose. An ethylcellulose product that can be used in the disclosed dosage forms is Ethocel™, marketed under a trade mark of The Dow Chemical Company. The rate of dissolution of the sustained release layer can be controlled by adjusting the ratio of water-soluble polymer to water-insoluble polymer in the coating or layer. The weight ratio of water-insoluble to water-soluble polymers can be adjusted, for example and without limitation, from 90:10 to 10:90, from 80:20 to 20:80, from 75:25 to 25:75, from 70:30 to 30:70, from 67.5:33.5 to 33.5:67.5 from 60:40 to 40:60, from 56:44 to 44:56, or to 50:50.

The sustained release coating can also contain plasticizers such as triethyl citrate (TEC) at levels of from 3% to 50% of the combined weight of the polymers. Other additives to the coating can include titanium dioxide, talc, colloidal silicone dioxide or citric acid.

Some examples of sustained release layers are shown in the following table. The various formulations include those in which the ratios of water-insoluble to water-soluble polymers are varied and one in which the ratios are reversed. Citric acid was added to a formula to keep the micro environment pH in the film low to inhibit the dissolution of HPMCAS-LF, which dissolves at ≥pH5.5 thus creating a lag at the beginning of the dissolution curve. In certain embodiments, the active ingredient, or API can be included in the sustained release layer. In initial testing metronidazole, a model drug, was micronized and added to the formulation as a suspension. Any of the appropriate disclosed API's can be added to the sustained release layer, however.

TABLE 1

Exemplary Sustained Release Layers

| Component | A (% w/w) | B (% w/w) | C (% w/w) | D (% w/w) | E (% w/w) | F (% w/w) |
|---|---|---|---|---|---|---|
| Ethocel | 51.0 | 34.9 | 34.5 | 34.4 | 60.2 | 36.1 |
| API | | | | 47.2 | | |
| PEO | | | | | 36.1 | 60.2 |
| HPMC E5 P | 17.0 | 13.1 | | | | |
| HPMCAS-LF | | | 27.6 | 11.5 | | |
| Talc | 3.6 | 2.8 | 3.6 | 2.4 | | |
| Titanium Dioxide | 24.0 | 18.5 | 24.0 | | | |
| Citric acid | | | | 6.9 | | |
| Colloidal silicon dioxide | 0.4 | | | | | |
| TEC | 4.0 | 26.2 | 3.4 | 4.6 | 3.6 | 3.6 |
| Totals* | 100.0 | 100.0 | 100.0 | 100.0 | 100.0 | 100.0 |

*Figures may not sum to 100, due to rounding

An exemplary core was synthesized as shown in Table 2. In this example, an osmotic agent is added to the core.

TABLE 2

| Component | Pellet Core (% w/w) |
|---|---|
| API | 20.0 |
| Avicell PH101 | 47.0 |
| Potassium chloride | 30.0 |
| Klucell EF | 3.0 |
| Totals | 100.0 |

A sustained release layer with the formula shown in the right hand column (F) of Table 1 was synthesized on an API containing bead. The formula was designated 2009-043-10A when the sustained release layer provided a 25% weight gain and 2009-043-10 when the sustained release layer provided a 35% gain. Additional layers were synthesized as shown in columns A and B of Table 1. In column B, the formula of column A was modified such that the colloidal silicon dioxide was removed and the plasticizer was increased to 50% w/w of the polymer level. All of the other ratios as shown in column A were maintained.

The formula of column A was also modified to produce the sustained release layer of column C of Table 1. In this formula, the colloidal silicon dioxide was removed and citric acid was added. The ratio of Ethocel:HPMCAS was decreased from 75:25 to 56:44. This formula was expected to provide a lower pH in the microenvironment to increase the lag time. A sample layered to produce a 25% weight gain and another sample with a 45% weight gain were subjected to dissolution testing.

Another embodiment of a sustained release layer was produced in which the drug or API was included in the sustained release layer. This layer is described in column D of Table 1. In this formula, the ratio between Ethocel and HPMCAS was 75:25. A micronized drug was added to the formula as a suspension. A sample with a 25% weight gain was subjected to dissolution testing.

Core tablets as described in Table 2 were coated with a sustained release layer formulated as in column A of Table 1. This formulation exhibited an initial slow drug release (3% in the first 3 hours).

Another embodiment of a sustained release coating was designed with polyethyleneoxide (PEO) to ethyl cellulose ratio of 37.5:62.5. Talc was also added to one sample at 10% to improve the coating process. The presence of talc did not affect drug release. The release profiles for these formulations processed with a 25% weight gain and a 40% weight gain were also determined. The formulations exhibited a 1 hour lag and the drug was substantially completely released within 9 hours.

While the disclosed compositions of a capsule containing a single population of beads or minitablets with a sustained release layer and an outer, delayed release layer are shown here in to be an effective delivery system with novel release characteristics and surprisingly low variability in absorption when administered to humans, it is understood that alternative compositions can be used in light of the present disclosure.

In certain embodiments a drug containing core bead or minitablet is coated with a delayed release layer that includes one or more water-insoluble polymers, one or more water-soluble polymers and a silicone oil to achieve a desired delay or lag time prior to release as in the present disclosure. Lag time and release are controlled by the proportion of the two types of polymers and the thickness of the layer. In such embodiments, the delayed release layer can include, but is not limited to cellulose acetate phthalate, cellulose acetate trimaletate, hydroxyl propyl methylcellulose phthalate, polyvinyl acetate phthalate, acrylic polymers, polyvinyl acetaldiethylamino acetate, hydroxypropyl methylcellulose acetate succinate, cellulose acetate trimellitate, shellac, methacrylic acid copolymers, Eudragit L30D, Eudragit L100, Eudragit FS30D, Eudragit S100 or combinations of any thereof. The delayed release layer can also include a plasticizer, or in certain embodiments the delayed release layer can include methacrylic acid copolymer Type B, mono- and diglycerides, dibutyl sebacate and polysorbate 80. The delayed release layer can also include a cellulose ether derivative, an acrylic resin, a copolymer of acrylic acid and methacrylic acid esters with quaternary ammonium groups, a copolymer of acrylic acid and methacrylic acid esters or a combination of any thereof. The layer can further include a powder component such as talc as a carrier for the silicone oil.

In certain embodiments of the invention, a CNS stimulant can be contained in a delayed and/or controlled release capsule. In such embodiments a water-insoluble capsule contains one or more compartments in which the drug or active agent is held. Additionally one or more absorbents, superabsorbents or osmagents are included in the drug containing compartments. The capsules also include one more apertures plugged with a water-soluble polymer, at least one in fluid communication with each compartment and a delayed release layer enclosing the entire capsule.

In such embodiments the length of initial delay can be controlled by the composition and thickness of the outer, delayed release layer. This layer can be a pH dependent layer or a pH independent layer as disclosed herein. When the capsule is administered to a human, the delayed release layer begins to lose integrity as the capsule passes through the GI tract. When the water-soluble plugs are exposed and dissolve, aqueous fluid enters the drug containing compartment(s) and is absorbed by the absorbent or osmagent, thus driving the active agent from the capsule through the aperture. The release profile can be controlled by the concentration and absorption characteristics of the absorbent or osmagent to obtain the desired profile.

Sustained Release Coatings on Dextroamphetamine Sulfate Pellets

Formulations of the disclosure are made in which hydrophobic excipients are introduced to give an added delay in the drug release. The plasticizer level is kept at 7.26% of the Ethocel™ level. The formulations are described in Table 3.

TABLE 3

Sustained Release Formulations

| Component | Lot Number | | | | | | | | |
|---|---|---|---|---|---|---|---|---|---|
| | 2009-066-51 | 2009-066-53 | 2009-066-59 | 2009-066-64 | 2009-066-67 % W/W | 2009-066-69 | 2009-066-72 | 2009-066-75 | 2009-066-78 |
| Ethocel ™ Std. 10 | 55.8 | 55.8 | 38.5 | 43.0 | 45.4 | 55.9 | 53.2 | 50.7 | 45.4 |
| Klucel ™ (EF) | 8.9 | 8.9 | 6.1 | 1.3 | 11.3 | | 2.9 | 5.6 | 11.3 |
| Triethyl Citrate | 2.6 | 2.6 | 2.8 | 3.1 | 3.3 | | | | |
| Imperial Talc 500 | 52.6 | | | | | | | | |
| Dibutyl Sebacate | | | | | | 4.1 | 3.9 | 3.7 | 3.3 |
| Magnesium Stearate | | 52.6 | 52.6 | 52.6 | 40.0 | 40.0 | 40.0 | 40.0 | 40.0 |

These formulations were coated to a 30% weight gain level and samples were submitted for testing at 10 mg free base capsule dose. The dissolution testing took place in pH 7.0 buffer with a paddle speed of 75 rpm.

Lot 2009-066-51 has a water-insoluble to water-soluble ratio of 80:20. This results in a significantly faster release profile. The API releases 25% in the first hour. In further formulations talc was removed and replaced with magnesium stearate.

In Lot 2009-066-53, which contained magnesium stearate, the initial release was significantly slower. Further changes included increasing the Ethocel™ level in Lot-59 and -64 while decreasing the Klucel® level. The ratio of Ethocel™ to Klucel® in Lot-59 and -64 respectfully is 86:14 and 97:3. This change was expected to slow the release from Lot 53, but the dissolution release time actually increased. Lot-67 included a decrease of the magnesium stearate and decrease in the Ethocel™ to Klucel® ratio (back to 80:20). This resulted in a release faster than the model profile.

Replacement of the hydrophilic plasticizer TEC with dibutyl sebacate (DBS), a hydrophobic plasticizer resulted in a significantly longer delay prior to initial release. Lot 2009-066-69 was the first lot utilizing DBS as a plasticizer.

With the addition of DBS and the removal of Klucel®, the initial drug release was less than 2% over 8 hours.

Klucel® was added back into the formulation in Lot 2009-066-72. The ratio of Ethocel™ to Klucel® was 95:5. The dissolution profile was similar to Lot 2009-066-69. In Lot 2009-066-75, the ratio of Ethocel™ to Klucel® decreased from 95:5 to 90:10. This change did not result in a different release profile compared to the two previous formulations.

For Lot 2009-066-78, the ratio of Ethocel™ to Klucel® was decreased to 80:20, for a higher level of water-soluble polymer. Formulation 2009-066-78 exhibited a 20% drug release over 4 hours followed by an increasing release until over 80% release.

DOE Sustained Release Coatings

A design of experiment (DOE) was set up with three ratios of Ethocel™ to Klucel® ratios: 70:30, 75:25, and 80:20. The coatings were applied in the GPCG2 with a 1.0 mm spray nozzle. For a DOE coating run 650.0 g of pellets were used. The pellets consisted of 80% w/w placebo pellets and 20% Dextroamphetamine sulfate pellets. The pellets were diluted to conserve the D-amphetamine sulfate pellets. The DOE formulations are shown in Table 4. Each coating formulation contained 12% solids w/w. The solvents consisted of ethanol to DI water at a ratio of 95:5.

magnesium stearate level was decreased from 40% w/w/ to 25% w/w. By making these changes, the dissolution profile shifts to the right far beyond the model profile. The DOE 11 formulation is similar to Lot 2009-066-78 (see Table 3 and Table 4 for formulations). DOE 11, 3, and 4 have release profiles that are close to the model profile. All three have an Ethocel™ to Klucel® ratio of 80:20, but differ in percent w/w of the hydrophobic excipients. The DOE 3 coating was the closest profile to the model.

Stability of DOE 3 and DOE 4

Figure 6:
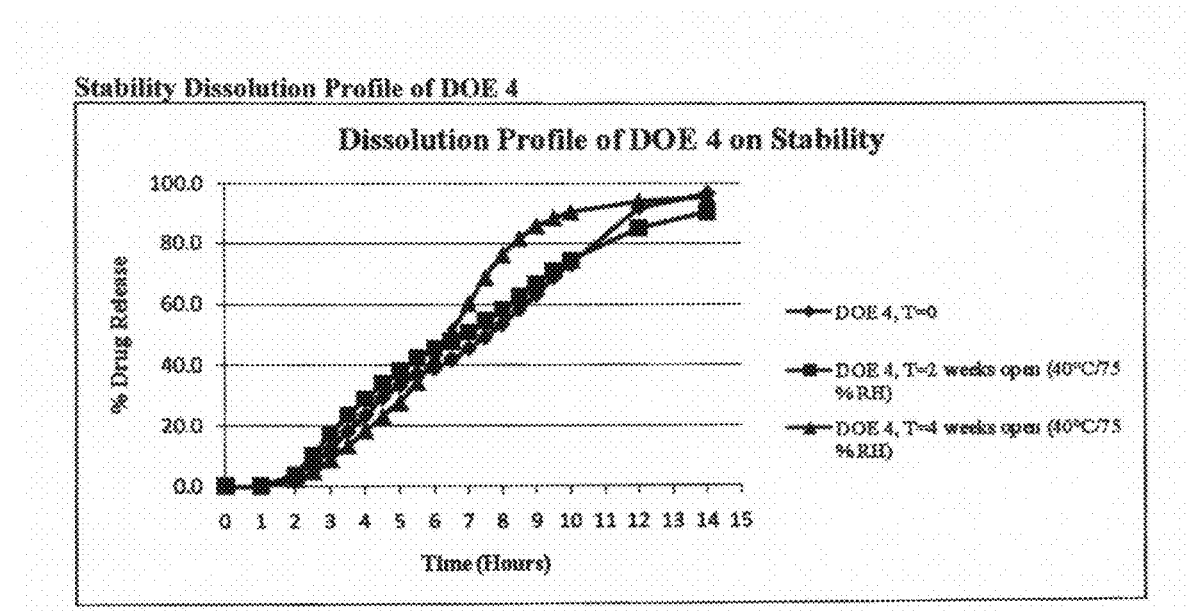
FIG. 6 is a graph of stability dissolution profile of DOE 4.
Figure 7:
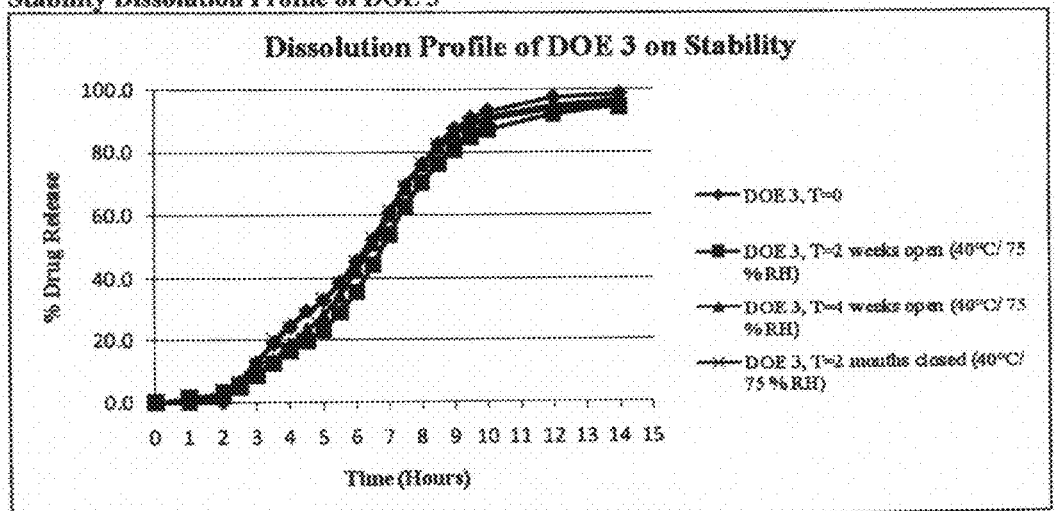
FIG. 7 is a graph of stability dissolution profile of DOE 3.

For a stability study, 13.6 mg (equivalent to 10.0 mg free base dose) dose capsules were loaded into HDPE bottles and loaded into the following stability chambers for the study: 40° C./75% RH, 25° C./60% RH, and 30° C./65% RH. Pellets were also loaded into HDPE bottles with no capsules at 40° C./75% RH for an open container study. After 2 and 4 weeks for the open container study at 40° C./75% RH dissolution testing of the pellets took place in pH 7.2 phosphate buffer. The dissolution results are shown in FIG. 6 and FIG. 7.

All of the dissolution profiles from the different stability time points had similar drug release profiles, demonstrating that the sustained release coatings are stable. The next step in the development was to add a pH dependent coating on top of the sustained release coating.

TABLE 4

DOE Formulations

| | Lot Number | | | | | | | | | | |
|---|---|---|---|---|---|---|---|---|---|---|---|
| | 2009-104-13 | 2009-104-17 | 2009-104-44 | 2009-104-48 | 2009-104-52 | 2009-104-55 | 2009-104-58 | 2009-104-61 | 2009-104-81 | 2009-138-12 | 2009-138-29 |
| | DOE Run | | | | | | | | | | |
| | 1 | 2 | 3 | 4 | 5 | 6 | 7 | 8 | 9 | 10 | 11 |
| Component | | | | | | % W/W | | | | | |
| Ethocel ™ Std. 10 | 41.18 | 36.64 | 49.15 | 39.29 | 34.84 | 43.30 | 41.59 | 46.43 | 41.86 | 57.58 | 44.08 |
| Klucel ® (EF) | 17.65 | 15.70 | 12.29 | 9.82 | 14.93 | 18.56 | 10.40 | 11.61 | 13.95 | 14.39 | 11.02 |
| Dibutyl Sebacate | 6.1 | 2.66 | 3.56 | 5.89 | 5.23 | 3.14 | 3.02 | 6.96 | 4.19 | 3.03 | 4.91 |
| Magnesium Stearate | 35.00 | 45.00 | 35.00 | 45.00 | 45.00 | 35.00 | 45.00 | 35.00 | 40.00 | 25.00 | 40.00 |

Each of the DOE formulations was coated to 30% weight gain, then samples were loaded into capsules at 13.6 mg dose (equivalent to 10.0 mg free base dose), and submitted for dissolution testing in pH 7.2 phosphate buffer with a paddle speed of 75 rpm.

Figure 4:
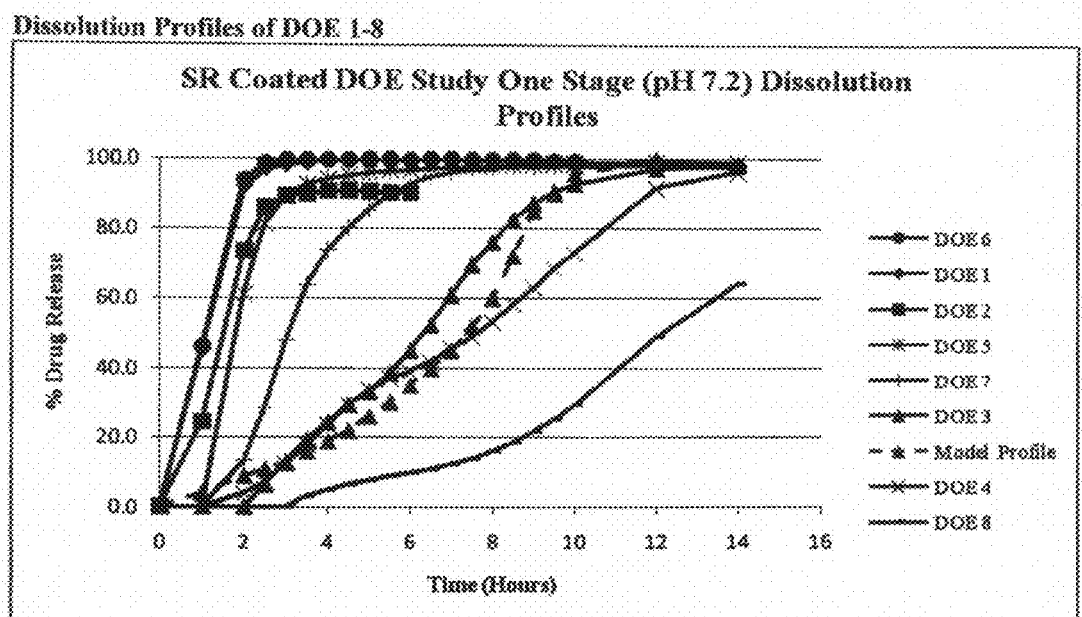
FIG. 4 is a graph of dissolution profiles of DOE 1-8.

A standard mixing procedure was developed for the sustained released coating preparations as follows. Charge the ethanol into an appropriate sized beaker. Place the beaker under a lab mixer with a Cowles blade attached. Create a vortex by increasing the mixing speed and charge the Ethocel™, Klucel®, and DBS into the ethanol. The speed of the mixer is turned down so there is no vortex and the excipients mixed until dissolved. Once the excipients dissolve, a vortex can be created for the addition of the magnesium stearate. The magnesium stearate is mixed for a minimum of 30 minutes or until no agglomerates are present. Adding the DI water to the mixing dispersion is the last step of the process. The first eight DOE dissolution profiles are shown in FIG. 4.

Figure 5:
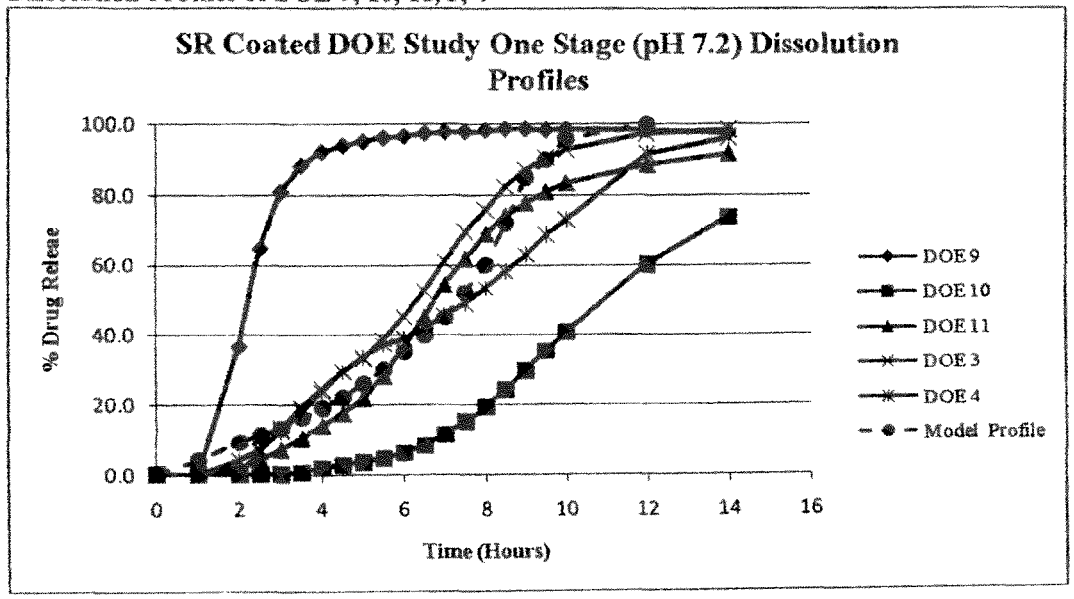
FIG. 5 is a graph of dissolution profiles of DOE 9, 10, 11, 3, 4.

As shown in FIG. 5, DOE 9 had an Ethocel™ to Klucel® ratio of 75:25 and produced a faster dissolution release. In DOE 10 the Ethocel™ Klucel® ratio was 80:20 and the pH Dependent Coatings For the pH dependent coatings studies, the DOE 3 pellets were used. Samples of 13.6 mg dose (10.0 mg free base dose) were loaded into capsules. The dissolution testing took place for 2 hours (T=0-2 hour) in 0.1N HCl, then in pH 6.0 phosphate buffer for 4 hours (T=2-6 hour), and finally in pH 7.0 phosphate buffer for the remaining time. The formulations are shown in Table 5.

TABLE 5 pH dependent Formulations

| Lot Number | 2009-104-76 | 2009-104-78 | 2009-104-92[1] | 2009-138-22 | 2009-138-25 |
|---|---|---|---|---|---|
| Component | | | % W/W | | |
| Eudragit ® S 100 | 60.6 | | 60.0 | 76.9 | 80.6 |
| Eudragit ® FS 30 D | | 64.5 | | | |
| Triethyl Citrate | 9.1 | 3.2 | 9.1 | | |
| Dibutyl Sebacate | | | | 7.7 | 8.1 |
| Magnesium Stearate | | | | 15.4 | |
| ImperialTalc 500 | 30.3 | 32.3 | 30.3 | | |

TABLE 5-continued pH dependent Formulations

| Lot Number | 2009-104-76 | 2009-104-78 | 2009-104-92[1] | 2009-138-22 | 2009-138-25 |
|---|---|---|---|---|---|
| Imwitor ® 900 K | | | | | 8.1 |
| Tween ® 80 | | | | | 3.2 |

[1]Same formulation as Lot 2009-104-76, but coated at a product temperature 4° C. higher.

Figure 8:
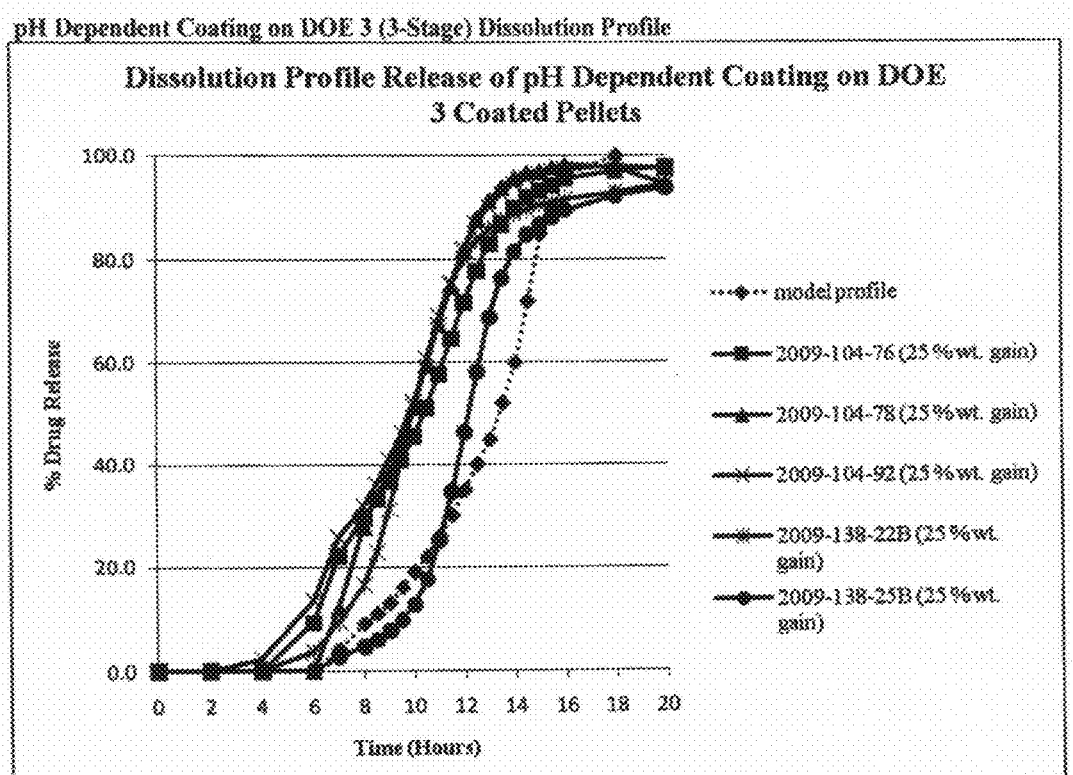
FIG. 8 is a graph of enteric coating on DOE 3 (3-Stage) dissolution profile.

The S 100 coatings are made with alcohol/DI water as the solvent at 94.4% w/w to 5.6% w/w and the FS 30 D coating is aqueous only. The dissolution profiles are shown in FIG. 8.

Lot 2009-104-78 exhibited a delay of 6 hours followed by a fast release. The S 100 formulation with GMS (Imwitor 900 K) at 10% w/w was then coated on the DOE 3 pellets. Lot 2009-138-25B exhibits a delay at the start of the drug release followed by a release curve that is similar to the model profile.

pH Dependent/SR Coated DOE 3 Pellets

The study with a pH dependent coating on the DOE 3 SR coating was repeated with a 100% active core pellet batch (no placebo pellets). The coating parameters are shown in Table 6.

TABLE 6

Lot 2009-138-32 Coating Parameters

| Parameters | Ranges |
|---|---|
| Product Temperature | 32.0-33.0° C. |
| Inlet Temperature | 48.4-54.1° C. |
| Exhaust Temperature | 29.3-30° C. |
| Process Air | 40-53 m³/h |
| Atomization Air | 2.0 Bar |
| Spray Time | 126.75 min |
| Spray Rate | 12.8 g/min |

Figure 9:
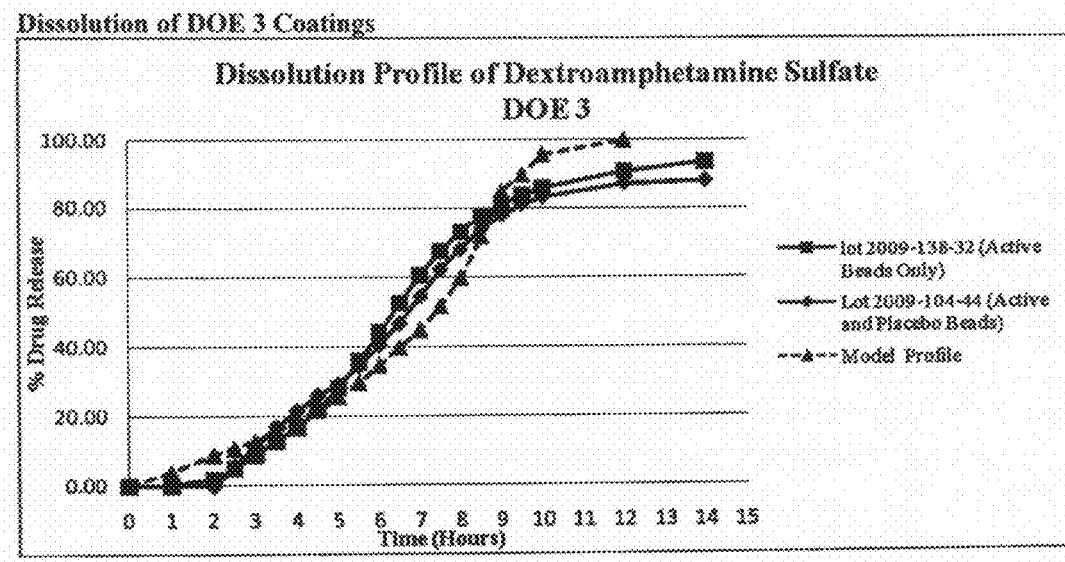
FIG. 9 is a graph of dissolution of DOE 3 coatings.

The dissolution profiles of the active and placebo diluted pellets of the DOE 3 coatings are shown in FIG. 9.

Figure 10:
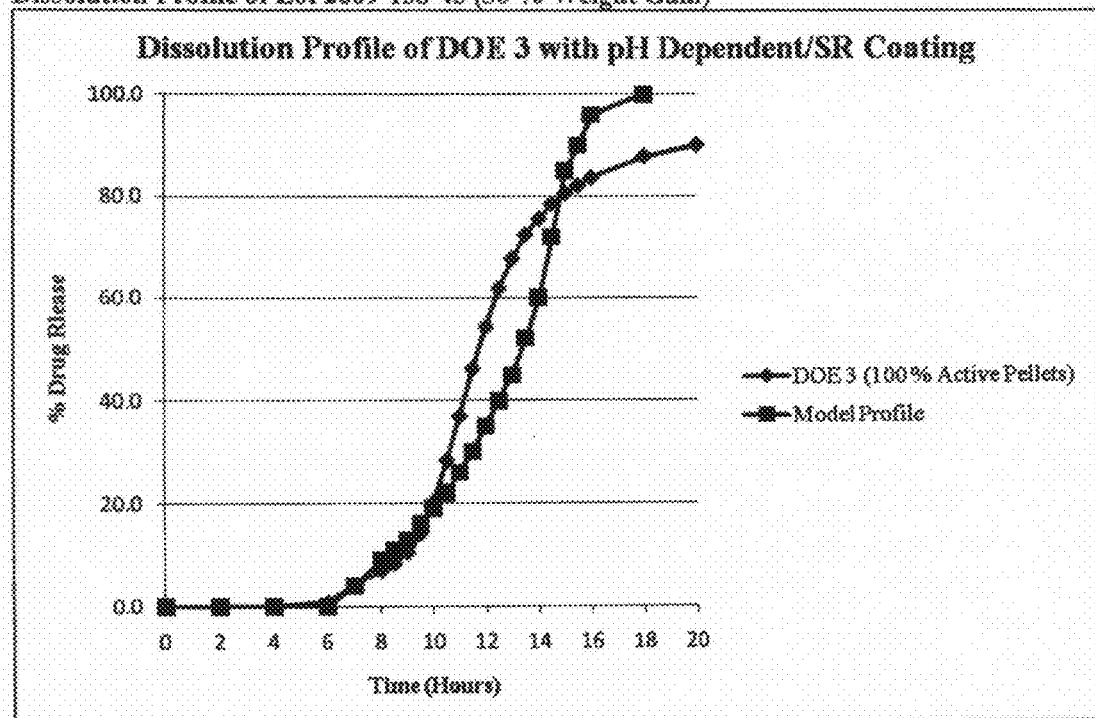
FIG. 10 is a graph of dissolution profile of Lot 2009-138-45 (30% Weight Gain).

The pH dependent coating (Lot 2009-138-45) containing GMS was then coated on the sustained release DOE 3 coating. The pellets were coated to a 30% weight gain with a sample pulled at 25% weight gain. The pellets were dosed into 13.6 mg capsules (10.0 mg freebase) and tested in the 3-stage dissolution study. The coating parameters are in Table 7 and the dissolution profiles are shown in FIG. 10.

TABLE 7

Lot 2009-138-45 Coating Parameters

| Parameters | Ranges |
|---|---|
| Product Temperature | 32.0-33.0° C. |
| Inlet Temperature | 48.4-54.1° C. |
| Exhaust Temperature | 29.3-30° C. |
| Process Air | 40-53 m³/h |
| Atomization Air | 2.0 Bar |
| Spray Time | 126.75 min |
| Spray Rate | 12.8 g/min |

Figure 11:
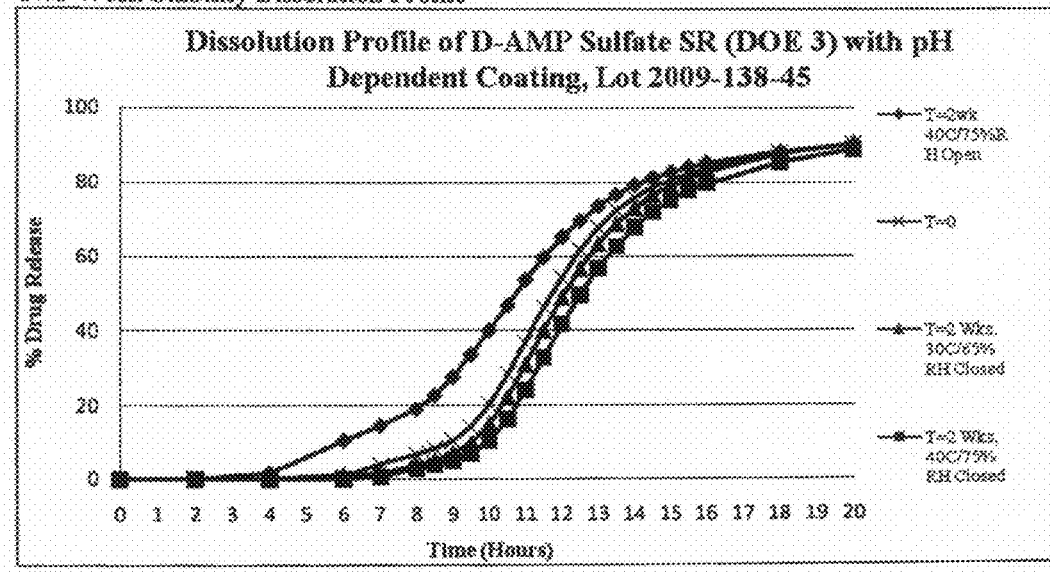
FIG. 11 is a graph of two-week stability dissolution profile.

At the 10-hour time point, DOE 3 had released 20% of the drug, closely matching the target profile. A portion of the pellets from DOE 3 (Lot 2009-138-45) were encapsulated to 13.6 mg dose (equivalent to 10 mg free base dose) in gelatin capsules and placed on stability. Bottles were filled with 16 capsules and placed in the following conditions: 4 bottles at 40° C./75% relative humidity, 4 bottles at 30° C./65% relative humidity, 1 bottle at 25° C./60% relative humidity. Two bottles just containing pellets equivalent to 16 capsules were placed in 40° C./75% relative humidity for an open dish accelerated study. After being in stability for two weeks samples were pulled from open container, 30° C./65% relative humidity, and 40° C./75% relative humidity. The dissolution profiles for these samples are shown in FIG. 11.

Figure 12:
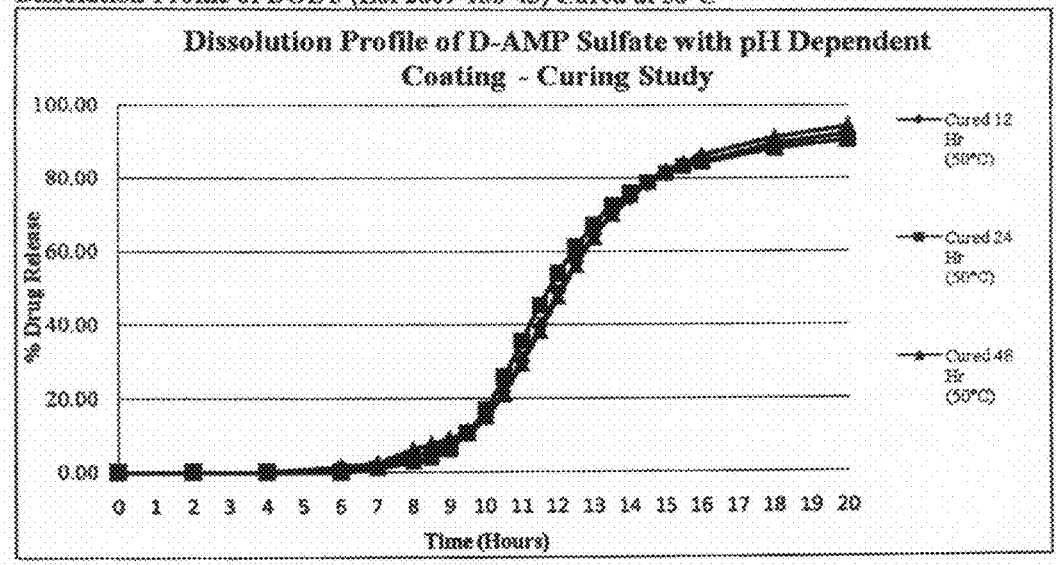
FIG. 12 is a graph of dissolution profile of DOE 3 (Lot 2009-138-45) cured at 50° C.

The two-week open container pellets started to release the drug at the 4-hour time point. The initial pellets and the other closed container samples did not start drug release until after the 6-hour time point. The two closed container samples released the drug slower than the initial release. It was presumed that pellets were absorbing moisture causing the GMS (Imwitor®) to become unstable and releasing the drug faster in the open container study. To try to stabilize the GMS, samples from Lot 2009-138-45 were placed in an oven and cured for 12 hours, 24 hours, and 48 hours at 50° C. The dissolution results are located in FIG. 12.

Figure 13:
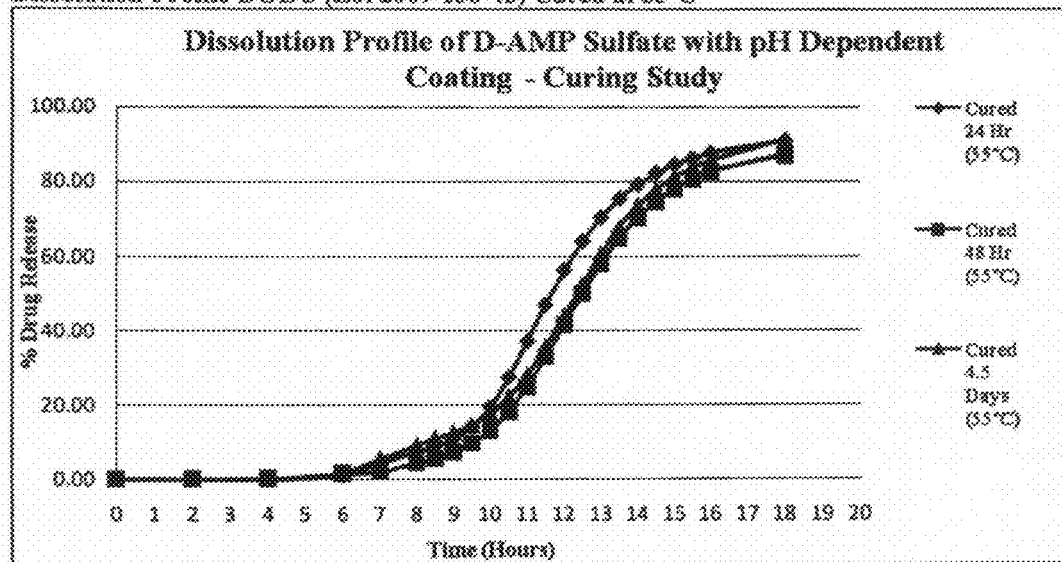
FIG. 13 is a graph of dissolution profile DOE 3 (Lot 2009-138-45) cured at 55° C.

At 50° C., the curing time did not affect the drug release. Another curing study was set up with the oven set at 55° C. Samples from Lot 2009-138-45 (DOE 3) were cured for 24, 48, and 108 hours (4.5 days). The dissolution profiles are shown in FIG. 13.

The release of drug after curing the pellets at 55° C. was not directly dependent on time. For the samples cured at 55° C., the pellets were dosed (13.6 mg/10.0 mg free base dose) into gelatin and HPMC capsules. The HPMC capsules contain a one-gram desiccant in each bottle to absorb any excess moisture. The samples were cured at 50° C. dosed only in the HPMC capsules with the one-gram desiccant in each bottle. Sixteen capsules were loaded into each bottle. The stability conditions are shown in Table 8.

TABLE 8

Stability Conditions for Cured Pellets

| Stability Conditions | 40° C./75% RH | 30° C./65% RH | 25° C./60% RH | 40° C./75% RH (Pellets only Open Container) |
|---|---|---|---|---|
| Capsule Type | Number of Bottles per Condition | | | |
| HPMC at 55° C. | 4 | 4 | 1 | 2 |
| Gelatin at 55° C. | 4 | 4 | 1 | |
| HPMC at 50° C. | 4 | 4 | 1 | 2 |

Figure 14:
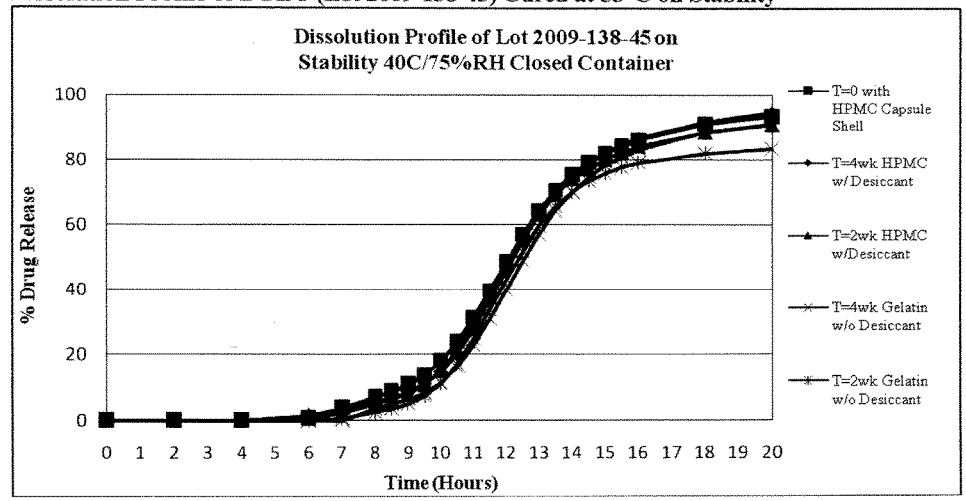
FIG. 14 is a graph of dissolution profile of DOE 3 (Lot 2009-138-45) cured at 55° C. on stability.

After 2 and 4 weeks, the samples cured at 55° C. were pulled and dissolution testing performed on them. The dissolution results for the stability samples are shown in FIG. 14.

For pellets cured at 55° C. loaded into the HPMC capsules the dissolution profile for the initial, 2-week, and 4-week samples gave similar results. This demonstrates product stability under those conditions. The gelatin-loaded capsules produced a dissolution profile a little slower than the initial release at 2- and 4-week samples.

Figure 15:
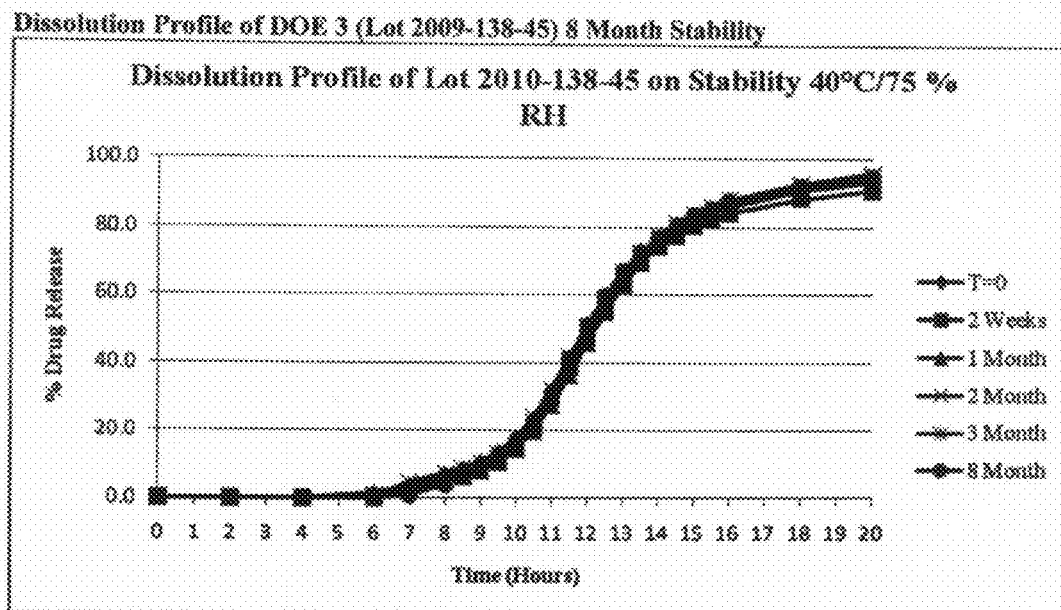
FIG. 15 is a graph of dissolution profile of DOE 3 (Lot 2009-138-45) 8 month stability.

Lot 2009-138-45 (DOE 3, SR and pH Coated) containing HPMC capsules with desiccant was left on stability 40° C./75% RH (closed container) for 8 months. Samples were pulled at 2, 3, and 8 months for dissolution testing. The dissolution profiles for the HPMC capsules containing the D-amphetamine sulfate pellets are shown in FIG. 15.

After 8 months in accelerated stability, the D-amphetamine sulfate has a similar profile to the initial release profile (T=0). The only difference is a slower release between hours 7-10.

Example 1

An example of a core pellet as described herein contains the following components as produced in a 5 kg batch.
Batch size 5,000 grams
Granulation Medium Solids 6%

TABLE 9

| Component | mg/1 mg pellet | % w/w | g/batch |
|---|---|---|---|
| Dextroamphetamine Sulfate, USP | 22.0 | 22.0 | 1100.0 |
| Avicel PH-101 | 65.0 | 65.0 | 3250.0 |
| Starch 1500 | 10.0 | 10.0 | 500.0 |
| Methocel E5 P LV[1] | 3.0 | 3.0 | 150.0 |
| Total | 10.0 | 100.0 | 5000.0 |
| DI Water | removed during processing | | 2356.0 |

In processing the extra water is added into the granulation medium. Water is 47.12% of the dry blend batch size. The granulation medium is 2506.0 grams and the spray rate is 418±20 g/min.

Example 2

An example of a sustained release coating to be applied to the core pellet is prepared with the following components.
Core batch size—1100.0 g
Coating weight gain—30%
Solids—12.0%

TABLE 10

| Component | mg/1 g pellet | solvent ratio | % w/w | g/batch |
|---|---|---|---|---|
| Ethocel S 10 | 14.75 | | 49.15 | 162.2 |
| Klucel EF | 3.69 | | 12.29 | 40.6 |
| Dibutyl Sebacate | 1.07 | | 3.56 | 11.7 |
| Mag Stearate 2257 | 10.50 | | 35.00 | 115.5 |
| | | | 100.00 | 330.0 |
| Ethanol | | 95 | | 2299.0 |
| DI Water | | 5 | | 121.0 |
| Theoretical amount of coated pellets (g) | | 1430 | | |

Example 3

An S100 pH dependent coating formulated for a 30% weight gain is formulated with the following components.
Coating weight gain—30%
Solids—10.0%
Batch size—715 g
Core pellet amount—550 g

TABLE 11

| Component | mg/1 g pellet | solvent ratio | % w/w | g/batch |
|---|---|---|---|---|
| Eudragit S100 | 24.18 | | 80.6 | 133.0 |
| Imwitor 900K | 2.43 | | 8.1 | 13.4 |
| Dibutyl Sebacate | 2.43 | | 8.1 | 13.4 |
| Tween 80 | 0.96 | | 3.2 | 5.3 |
| Ethanol | | 94.4 | | 1402.5 |
| DI Water | | 5.6 | | 82.5 |
| | | | 100.0 | 1650.0 |
| Theoretical amount of coated pellets (g) | 880.0 | | | |

Example 4

An S100 pH dependent coating formulated for a 50% weight gain contains the following components.
Coating weight gain—50.0%
Solids—10.0%
Batch size—715 g
Core pellet amount—550 g

TABLE 12

| Component | mg/1 g pellet | solvent ratio | % w/w | g/batch |
|---|---|---|---|---|
| Eudragit S100 | 40.30 | | 80.6 | 221.7 |
| Imwitor 900K | 4.05 | | 8.1 | 22.3 |
| Dibutyl Sebacate | 4.05 | | 8.1 | 22.3 |
| Tween 80 | 1.60 | | 3.2 | 8.8 |
| Ethanol | | 94.4 | | 2337.5 |
| DI Water | | 5.6 | | 137.5 |
| | | | 100.0 | 2750.0 |
| Theoretical amount of coated pellets (g) | 990.0 | | | |

Example 5

A formulation was made with a pellet core as in Example 1, a sustained release coating as in Example 2 and a pH dependent coating with a 30% weight gain as in Example 3.

TABLE 13

| Component | mg/1 g pellet | % w/w |
|---|---|---|
| Dextroamphetamine Sulfate USP | 22.00 | 13.75 |
| Avicel PH-101 | 65.00 | 40.63 |
| Starch 1500 | 10.00 | 6.25 |
| Methocel E5 P LV[1] | 3.00 | 1.88 |
| Ethocel Std 10 | 14.75 | 9.22 |
| Klucel EF | 3.69 | 2.30 |
| Dibutyl Sebacate | 1.07 | 0.67 |
| Mag Stearate 2257 | 10.50 | 6.56 |
| Eudragit S100 | 24.18 | 15.11 |
| Imwitor 900K | 2.43 | 1.52 |
| Dibutyl Sebacate | 2.43 | 1.52 |
| Tween 80 | 0.96 | 0.60 |
| | 160.00 | 100.00 |

Example 6

A formulation was made with a pellet core as in Example 1, a sustained release coating as in Example 2 and a pH dependent coating with a 50% weight gain as in Example 3.

TABLE 14

| Component | mg/1 g pellet | % w/w |
|---|---|---|
| Dextroamphetamine Sulfate USP | 22.00 | 12.22 |
| Avicel PH-101 | 65.00 | 36.11 |
| Starch 1500 | 10.00 | 5.56 |
| Methocel E5 P LV[1] | 3.00 | 1.67 |
| Ethocel Std 10 | 14.75 | 8.19 |
| Klucel EF | 3.69 | 2.05 |
| Dibutyl Sebacate | 1.07 | 0.59 |
| Mag Stearate 2257 | 10.50 | 5.83 |
| Eudragit S100 | 40.30 | 22.39 |
| Imwitor 900K | 4.05 | 2.25 |
| Dibutyl Sebacate | 4.05 | 2.25 |
| Tween 80 | 1.60 | 0.89 |
| | 180.00 | 100.00 |

Example 7

An example of a sustained release coating with an alternate ratio of water-soluble (Klucel) to water-insoluble polymer (Ethocel) is prepared with the following components to obtain a faster release profile.

Core batch size—1100.0 g
Coating weight gain—30%
Solids—12.0%

TABLE 15

| Component | mg/1 g pellet | solvent ratio | % w/w | g/batch |
|---|---|---|---|---|
| Ethocel Std 10 | 12.48 | | 41.59 | 137.2 |
| Klucel EF | 3.12 | | 10.40 | 34.3 |
| Dibutyl Sebacate | 0.90 | | 3.01 | 9.9 |
| Mag Stearate 2257 | 13.50 | | 45.00 | 148.5 |
| | | | | 330.0 |
| Ethanol | | 95 | | 2299.0 |
| DI Water | | 5 | | 121.0 |
| | | | 100.00 | 2750.0 |
| Theoretical amount of coated pellets (g) | 1430 | | | |

Example 8

A formulation was made with a pellet core as in Example 1, a sustained release coating as in Example 7 and a pH dependent coating with a 30% weight gain as in Example 3.

TABLE 16

| Component | mg/1 g pellet | % w/w |
|---|---|---|
| Dextroamphetamine Sulfate USP | 22.00 | 13.75 |
| Avicel PH-101 | 65.00 | 40.63 |
| Starch 1500 | 10.00 | 6.25 |
| Methocel E5 P LV[1] | 3.00 | 1.88 |
| Ethocel Std 10 | 12.48 | 7.80 |
| Klucel EF | 3.12 | 1.95 |
| Dibutyl Sebacate | 0.90 | 0.56 |
| Mag Stearate 2257 | 13.50 | 8.44 |
| Eudragit S100 | 24.18 | 15.11 |
| Imwitor 900K | 2.43 | 1.52 |
| Dibutyl Sebacate | 2.43 | 1.52 |
| Tween 80 | 0.96 | 0.60 |
| | 160.00 | 100.00 |

Example 9

A formulation was made with a pellet core as in Example 1, a sustained release coating as in Example 7 and a pH dependent coating with a 50% weight gain as in Example 4.

TABLE 17

| Component | mg/1 g pellet | % w/w |
|---|---|---|
| Dextroamphetamine Sulfate USP | 22.00 | 12.22 |
| Avicel PH-101 | 65.00 | 36.11 |
| Starch 1500 | 10.00 | 5.56 |
| Methocel E5 P LV[1] | 3.00 | 1.67 |
| Ethocel Std 10 | 12.48 | 6.93 |
| Klucel EF | 3.12 | 1.73 |
| Dibutyl Sebacate | 0.90 | 0.50 |
| Mag Stearate 2257 | 13.50 | 7.50 |

TABLE 17-continued

| Component | mg/1 g pellet | % w/w |
|---|---|---|
| Eudragit S100 | 40.30 | 22.39 |
| Imwitor 900K | 4.05 | 2.25 |
| Dibutyl Sebacate | 4.05 | 2.25 |
| Tween 80 | 1.60 | 0.89 |
| | 180.00 | 100.00 |

Example 10

Another example of a sustained release coating according to the disclosure is prepared with the following components.

Core batch size—1100.0 g
Coating weight gain—30%
Solids—12.0%

TABLE 18

| Component | mg/1 g pellet | solvent ratio | % w/w | g/batch |
|---|---|---|---|---|
| Ethocel Std 10 | 13.22 | | 44.08 | 145.5 |
| Klucel EF | 3.1 | | 11.02 | 36.4 |
| Dibutyl Sebacate | 1.47 | | 4.90 | 16.2 |
| Mag Stearate 2257 | 12.00 | | 40.00 | 132.0 |
| Solvents | | | | |
| Ethanol | | 95 | | 2299.0 |
| DI Water | | 5 | | 121.0 |
| | | | 100.00 | 2750.0 |
| Theoretical amount of coated pellets (g) | 1430 | | | |

Example 11

A formulation was made with a pellet core as in Example 1, a sustained release coating as in Example 10 and a pH dependent coating with a 30% weight gain as in Example 3.

TABLE 19

| Component | mg/1 g pellet | % w/w |
|---|---|---|
| Dextroamphetamine Sulfate USP | 22.00 | 13.75 |
| Avicel PH-101 | 65.00 | 40.63 |
| Starch 1500 | 10.00 | 6.25 |
| Methocel E5 P LV[1] | 3.00 | 1.88 |
| Ethocel Std 10 | 13.22 | 8.27 |
| Klucel EF | 3.31 | 2.07 |
| Dibutyl Sebacate | 1.47 | 0.92 |
| Mag Stearate 2257 | 12.00 | 7.50 |
| Eudragit S100 | 24.18 | 15.11 |
| Imwitor 900K | 2.43 | 1.52 |
| Dibutyl Sebacate | 2.43 | 1.52 |
| Tween 80 | 0.96 | 0.60 |
| | 160.00 | 100.00 |

Example 12

An example of a core pellet free of starch or osmagent as described herein contains the following components as produced in a 2 kg batch. These core pellets are used in Examples 17-21.

TABLE 20

| Component | mg/1 g pellet | % w/w | g/batch |
|---|---|---|---|
| Dextroamphetamine Sulfate, USP | 220 | 22.0 | 440 |
| Microcrystalline Cellulose, NF | 780 | 78.0 | 1560 |
| Total | 1000 | 100.0 | 2000 |
| DI Water | removed during processing | | 1440 |

Example 13

An example of a slow sustained release coating as described herein for use in Slow Release Formulation (1 and 2) 25% SR+20% or 30% pH Coating.

TABLE 21

| SR Coat Slow Release (1 and 2) | | | | |
|---|---|---|---|---|
| Coating Weight gain: | | 25.0 | | |
| Solids %: | | 12.0 | | |
| Component | mg/g | solvent ratio | % w/w | g/batch |
| Ethyl Cellulose, NF | 81.5 | | 8.15 | 123 |
| Hydroxypropyl Cellulose, NF | 20.4 | | 2.04 | 31 |
| Dibutyl Sebacate, NF | 5.9 | | 0.59 | 9 |
| Magnesium Stearate, NF | 58.0 | | 5.80 | 88 |
| Ethanol (denatured) | | 95 | | 1742 |
| DI Water | | 5 | | 92 |
| Theoretical amount of coated pellets (g) | | 1250 | | |

Example 14

An example of a slow enteric coatings as described herein for use in Slow Release Formulation (1 and 2) 25% SR+20% or 30% pH Coating.

TABLE 22

| S100 pH Dependent Coat Slow Release (1) | | | | |
|---|---|---|---|---|
| Coating Weight gain: | | 20% | | |
| Solids %: | | 10% | | |
| Batch size (g) | | 1500 | | |
| Core pellet amount (g) | | 1250 | | |
| Component | mg/g | solvent ratio | % w/w | g/batch |
| Methacrylic Acid Copolymer Type-B | 133.7 | | 13.37 | 202 |
| Mono-and Di-glycerides, NF | 13.4 | | 1.34 | 20 |
| Dibutyl Sebacate, NF | 13.4 | | 1.34 | 20 |
| Polysorbate 80, NF | 5.3 | | 0.53 | 8 |
| Ethanol (denatured) | | 94.4 | | 2138 |
| DI Water | | 5.6 | | 113 |
| Theoretical amount of coated pellets (g) | 1500 | | | |

TABLE 23

| S100 pH Dependent Coat Slow Release (2) | | | | |
|---|---|---|---|---|
| Coating Weight gain: | | 30% | | |
| Solids %: | | 10% | | |
| Batch size (g) | | 1625 | | |
| Core pellet amount (g) | | 1250 | | |
| Component | mg/g | solvent ratio | % w/w | g/batch |
| Methacrylic Acid Copolymer Type-B | 185.1 | | 18.51 | 302 |
| Mono-and Di-Glycerides, NF | 18.6 | | 1.86 | 30 |
| Dibutyl Sebacate, NF | 18.6 | | 1.86 | 30 |
| Polysorbate 80, NF | 7.4 | | 0.74 | 12 |
| Ethanol (denatured) | | 94.4 | | 3206 |
| DI Water | | 5.6 | | 169 |
| Theoretical amount of coated pellets (g) | 1625 | | | |

Example 15

An example of a medium sustained release coating as described herein for use in Medium Release Formulation (1 and 2) 20% SR+20% or 30% pH Coating.

TABLE 24

| SR Coat Medium Release (1 and 2) | | | | |
|---|---|---|---|---|
| Coating Weight gain: 20% | | | | |
| Solids %: | | 12% | | |
| Component | mg/g | solvent ratio | % w/w | g/batch |
| Ethyl Cellulose, NF | 134.0 | | 13.40 | 98 |
| Hydroxypropyl Cellulose, NF | 33.5 | | 3.35 | 25 |
| Dibutyl Sebacate, NF | 9.7 | | 0.97 | 7 |
| Magnesium Stearate, NF | 95.5 | | 9.55 | 70 |
| Ethanol (denatured) | | 95 | | 1393 |
| DI Water | | 5 | | 73 |
| Amount of coated pellets (g) | 1200 | | | |

TABLE 25

| S100 pH Dependent Coat Medium Release (1) | | | | |
|---|---|---|---|---|
| Coating Weight gain: | | 20.0 | | |
| Solids %: | | 10.0 | | |
| Batch size (g) | | 1440 | | |
| Core pellet amt (g) | | 1000 | | |
| Component | mg/g | solvent ratio | % w/w | g/batch |
| Methacrylic Acid Copolymer Type-B | 120.3 | | 12.03 | 193 |
| Mono-and Di-Glycerides, NF | 13.6 | | 1.36 | 19 |
| Dibutyl Sebacate, NF | 13.6 | | 1.36 | 19 |
| Polysorbate 80, NF | 5.4 | | 0.54 | 8 |
| Ethanol (denatured) | | 94.4 | | 2077 |
| DI Water | | 5.6 | | 123 |
| Amount of coated pellets (g) | 1440 | | | |

TABLE 26

S100 pH Dependent Coat Medium Release (2)

| | |
|---|---|
| Coating Weight gain: | 30% |
| Solids %: | 10% |
| Batch size (g) | 1560 |
| Core pellet amount (g) | 1200 |

| Component | mg/g | solvent ratio | % w/w | g/batch |
|---|---|---|---|---|
| Methacrylic Acid Copolymer Type-B | 185.1 | | 18.51 | 290 |
| Mono-and Di-Glycerides, NF | 18.6 | | 1.86 | 29 |
| Dibutyl Sebacate, NF | 18.6 | | 1.86 | 29 |
| Polysorbate 80, NF | 7.3 | | 0.73 | 12 |
| Ethanol (denatured) | | 94.4 | | 3210 |
| DI Water | | 5.6 | | 190 |
| Amount of coated pellets (g) | | | | 1560 |

Example 16

An example of fast release coatings for Fast Release Formulation 20% SR+20% pH Coating.

TABLE 27

SR Coat Fast Release

| | |
|---|---|
| Coating Weight gain: | 20.0 |
| Solids %: | 12 |

| Component | mg/g | solvent ratio | % w/w | g/batch |
|---|---|---|---|---|
| Ethyl Cellulose, NF | 57.5 | | 5.75 | 83 |
| Hydroxypropyl Cellulose, NF | 14.4 | | 1.44 | 21 |
| Dibutyl Sebacate, NF | 4.2 | | 0.42 | 6 |
| Magnesium Stearate, NF | 6.22 | | 6.22 | 90 |
| Ethanol (denatured) | | 95 | | 1393 |
| DI Water | | 5 | | 73 |
| Amount of coated pellets (g) | | | | 1200 |

TABLE 28

S100 pH Dependent Coat Fast Release

| | |
|---|---|
| Coating Weight gain: | 20% |
| Solids %: | 10% |
| Batch size (g) | 1440 |
| Core pellet amount (B) | 1200 |

| Component | mg/g | solvent ratio | % w/w | g/batch |
|---|---|---|---|---|
| Methacrylic Acid Copolymer Type-B | 133.7 | | 13.37 | 193 |
| Mono-and Di-Glycerides, NF | 13.4 | | 1.34 | 19 |
| Dibutyl Sebacate, NF | 13.4 | | 1.34 | 19 |
| Polysorbate 80, NF | 5.3 | | 0.53 | 8 |
| Ethanol (denatured) | | 94.4 | | 2077 |
| DI Water | | 5.6 | | 123 |
| Amount of coated pellets (g) | | | | 1440 |

Example 17

An example of a composition of Dextroamphetamine Sulfate, 30 mg capsules (Slow Release Formulation 1) with a core as described in Example 12, 25% sustained release coating weight gain, +20% delayed release (enteric) coating weight gain.

TABLE 29

| | | Strength (label claim) 30 mg | |
|---|---|---|---|
| Component and Quality Standard (and Grade, if applicable) | Function | Quantity per unit (mg) | % |
| Dextroamphetamine Sulfate, USP | Active ingredient | 30.00 | 14.59 |
| Microcrystalline Cellulose, NF (Avicel PH-101) | Binder | 106.36 | 51.74 |
| Ethyl Cellulose, NF (Ethocel Standard 10 Premium) | Film Former | 16.76 | 8.15 |
| Hydroxypropyl Cellulose, NF (Klucel EF Pharm) | Film Former | 4.19 | 2.04 |
| Dibutyl Sebacate, NF | Film Plasticizer | 1.21 | 0.59 |
| Magnesium Stearate, NF | Hydrophobic Film Component | 11.93 | 5.80 |
| Methacrylic Acid Copolymer Type-B (Eudragit S 100) | Film Former | 27.48 | 13.37 |
| Mono-and Di-Glycerides, NF (Imwitor 900K) | Film Plasticizer | 2.76 | 1.34 |
| Dibutyl Sebacate, NF | Film Plasticizer | 2.76 | 1.34 |
| Polysorbate 80, NF | Solubilizer | 1.09 | 0.53 |
| Talc USP, EP | | 1.02 | 0.50 |
| Total | | 205.56 | 100.0 |

Example 18

An example of a composition of Dextroamphetamine Sulfate, 30 mg capsules (Slow Release Formulation 2) with a core as in Example 12, 25% sustained release coating weight gain, +30% delayed release (enteric) coating weight gain.

TABLE 30

| | | Strength (label claim) 30 mg | |
|---|---|---|---|
| Component and Quality Standard (and Grade, if applicable) | Function | Quantity per unit (mg) | % |
| Dextroamphetamine Sulfate, USP | Active ingredient | 30.00 | 13.47 |
| Microcrystalline Cellulose, NF (Avicel PH-101) | Binder | 106.36 | 47.76 |
| Ethyl Cellulose, NF (Ethocel Standard 10 Premium) | Film Former | 16.76 | 7.53 |

TABLE 30-continued

| Component and Quality Standard (and Grade, if applicable) | Function | Strength (label claim) 30 mg | |
|---|---|---|---|
| | | Quantity per unit (mg) | % |
| Hydroxypropyl Cellulose, NF (Klucel EF Pharm) | Film Former | 4.19 | 1.88 |
| Dibutyl Sebacate, NF | Film Plasticizer | 1.21 | 0.54 |
| Magnesium Stearate, NF | Hydrophobic Film Component | 11.93 | 5.36 |
| Methacrylic Acid Copolymer Type-B (Eudragit S 100) | Film Former | 41.22 | 18.51 |
| Mono-and Di-Glycerides, NF (Imwitor 900K) | Film Plasticizer | 4.14 | 1.86 |
| Dibutyl Sebacate, NF | Film Plasticizer | 4.14 | 1.86 |
| Polysorbate 80, NF | Solubilizer | 1.64 | 0.74 |
| Talc USP, EP | | 1.11 | 0.50 |
| Total | | 222.7 | 100.0 |

Example 19

An example of a composition of Dextroamphetamine Sulfate, 30 mg capsules (Medium Release Formulation 1) with a core as in Example 12, 20% sustained release coating weight gain, +20% delayed release (enteric) coating weight gain.

TABLE 31

| Component and Quality Standard (and Grade, if applicable) | Function | Strength (label claim) 30 mg | |
|---|---|---|---|
| | | Quantity per unit (mg) | % |
| Dextroamphetamine Sulfate, USP | Active ingredient | 30.00 | 15.44 |
| Microcrystalline Cellulose, NF (Avicel PH-101) | Binder | 106.36 | 54.73 |
| Ethyl Cellulose, NF (Ethocel Standard 10 Premium) | Film Former | 13.40 | 6.90 |
| Hydroxypropyl Cellulose, NF (Klucel EF Pharm) | Film Former | 3.35 | 1.72 |
| Dibutyl Sebacate, NF | Film Plasticizer | 0.97 | 0.50 |
| Magnesium Stearate, NF | Hydrophobic Film Component | 9.55 | 4.91 |
| Methacrylic Acid Copolymer Type-B (Eudragit S 100) | Film Former | 26.38 | 12.03 |
| Mono-and Di-Glycerides, NF (Imwitor 900K) | Film Plasticizer | 2.65 | 1.36 |
| Dibutyl Sebacate, NF | Film Plasticizer | 2.65 | 1.36 |
| Polysorbate 80, NF | Solubilizer | 1.05 | 0.54 |
| Talc USP, EP | | 0.98 | 0.50 |
| Total | | 194.34 | 100.0 |

Example 20

An example of a composition of Dextroamphetamine Sulfate, 30 mg capsules (Medium Release Formulation 2) with a core as in Example 12, 20% sustained release coating weight gain, +30% delayed release (enteric) coating weight gain.

TABLE 32

| Component and Quality Standard (and Grade, if applicable) | Function | Strength (label claim) 30 mg | |
|---|---|---|---|
| | | Quantity per unit (mg) | % |
| Dextroamphetamine Sulfate, USP | Active ingredient | 30.00 | 14.03 |
| Microcrystalline Cellulose, NF (Avicel PH-101) | Binder | 106.36 | 49.75 |
| Ethyl Cellulose, NF (Ethocel Standard 10 Premium) | Film Former | 13.40 | 6.27 |
| Hydroxypropyl Cellulose, NF (Klucel EF Pharm) | Film Former | 3.35 | 1.57 |
| Dibutyl Sebacate, NF | Film Plasticizer | 0.97 | 0.45 |
| Magnesium Stearate, NF | Hydrophobic Film Component | 9.55 | 4.47 |
| Methacrylic Acid Copolymer Type-B (Eudragit S 100) | Film Former | 39.57 | 18.51 |
| Mono-and Di-Glycerides, NF (Imwitor 900K) | Film Plasticizer | 3.98 | 1.86 |
| Dibutyl Sebacate, NF | Film Plasticizer | 3.98 | 1.86 |
| Polysorbate 80, NF | Solubilizer | 1.57 | 0.73 |
| Talc USP, EP | | 1.06 | 0.50 |
| Total | | 213.79 | 100.0 |

Example 21

An example of a composition of Dextroamphetamine Sulfate, 30 mg capsules (Fast Release Formulation) with a core as in Example 12, 20% sustained release coating weight gain, +20% delayed release (enteric) coating weight gain.

TABLE 33

| Component and Quality Standard (and Grade, if applicable) | Function | Strength (label claim) 30 mg | |
|---|---|---|---|
| | | Quantity per unit (mg) | % |
| Dextroamphetamine Sulfate, USP | Active ingredient | 30.00 | 15.20 |
| Microcrystalline Cellulose, NF (Avicel PH-101) | Binder | 106.36 | 53.90 |
| Ethyl Cellulose, NF (Ethocel Standard 10 Premium) | Film Former | 11.34 | 5.75 |
| Hydroxypropyl Cellulose, NF (Klucel EF Pharm) | Film Former | 2.84 | 1.44 |
| Dibutyl Sebacate, NF | Film Plasticizer | 0.82 | 0.42 |
| Magnesium Stearate, NF | Hydrophobic Film Component | 12.27 | 6.22 |
| Methacrylic Acid Copolymer Type-B (Eudragit S 100) | Film Former | 26.38 | 13.37 |
| Mono-and Di-Glycerides, NF (Imwitor 900K) | Film Plasticizer | 2.65 | 1.34 |
| Dibutyl Sebacate, NF | Film Plasticizer | 2.65 | 1.34 |
| Polysorbate 80, NF | Solubilizer | 1.05 | 0.53 |
| Talc USP, EP | | 0.98 | 0.50 |
| Total | | 197.34 | 100.0 |

Example 22

The five formulations described in Examples 17-21 were subjected to dissolution testing as described. The dissolution data are shown in the following table.

TABLE 34

| TIME (HOURS) | FAST (446604) 20% SR; 20% EC | MEDIUM (446603) 20% SR; 30% EC | MEDIUM (446605) 20% SR; 20% EC | SLOW (446602) 25% SR; 20% EC | SLOW (446606) 25% SR; 30% EC |
|---|---|---|---|---|---|
| 0. | 0.0 | 0.0 | 0.0 | 0.0 | 0.0 |
| 2. | 1.6 | 2.9 | 0.2 | 0.0 | 0.5 |
| 4. | 2.4 | 5.7 | 0.6 | 0.0 | 1.3 |
| 6. | 4.0 | 9.9 | 1.4 | 0.0 | 2.1 |
| 7. | 6.6 | 13.1 | 2.5 | 1.1 | 2.7 |
| 8. | 9.7 | 16.3 | 5.0 | 3.0 | 3.1 |
| 9. | 15.0 | 19.6 | 11.9 | 7.9 | 3.3 |
| 10. | 25.8 | 23.0 | 25.7 | 18.0 | 4.4 |
| 12. | 57.7 | 39.1 | 60.6 | 47.6 | 14.4 |
| 14. | 81.5 | 64.0 | 81.4 | 71.9 | 41.7 |
| 16. | 91.7 | 79.7 | 90.5 | 85.1 | 66.4 |
| 20. | 97.7 | 89.8 | 96.2 | 94.8 | 85.7 |

Figure 16:
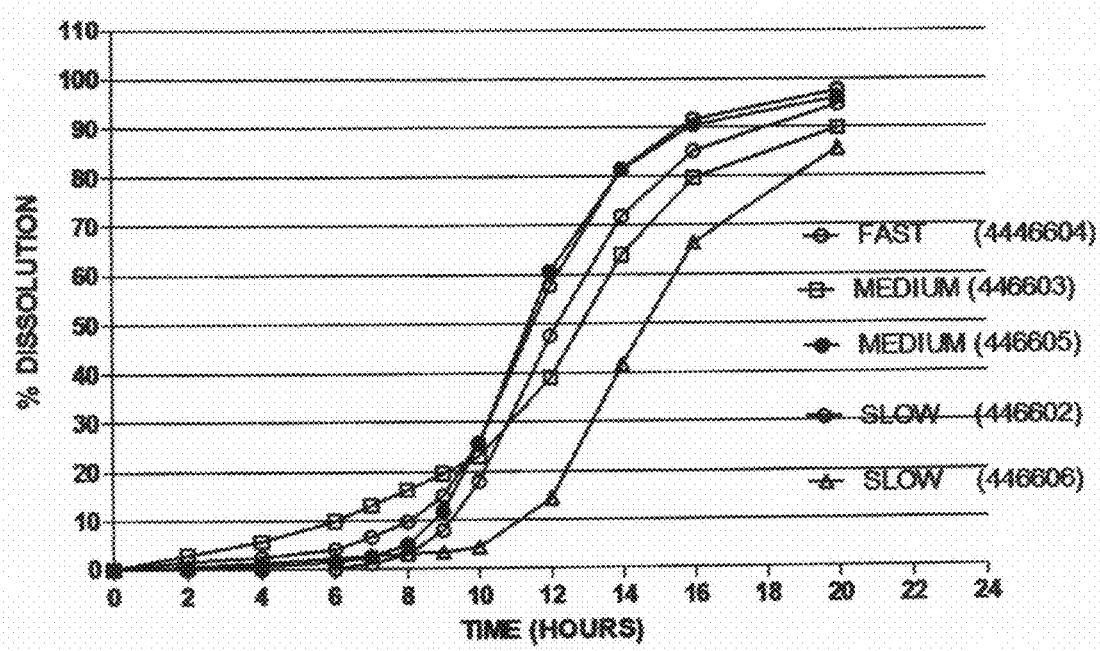
FIG. 16 is a graph of the dissolution profiles of the formulations described in Examples 14-18.

A graph of the dissolution data is shown in FIG. 16. As can be seen in the graph, the formulations provided a delayed release of from 6-10 hours followed by a sustained increasing release over the next 10 hours.

Example 23

A parallel, five-arm, open-label, single-dose, fasting study of Dextroamphetamine 30 mg capsules in healthy, non-smoking male subjects was conducted, administering the five formulations described in Examples 13-17 to 56 healthy male volunteers aged 18 to 45 years.

Five formulations were administered orally during the trial:

Treatment A: 1 Dextroamphetamine Sulfate Capsule, 30 mg, CII (20% SR, 30% ER coat, Medium Release);

Treatment B: 1 Dextroamphetamine Sulfate Capsule, 30 mg, CII (25% SR, 20% ER coat, Slow Release);

Treatment C: 1 Dextroamphetamine Sulfate Capsule, 30 mg, CII (20% SR, 20% ER coat, Fast Release), Treatment D: 1 Dextroamphetamine Sulfate Capsule, 30 mg, CII (25% SR, 30% ER coat, Slow Release);

Treatment E: 1 Dextroamphetamine Sulfate Capsule, 30 mg, CII (20% SR, 20% ER coat, Medium Release).

The pharmaceuticals were administered daily at 8 AM and plasma amphetamine concentrations were determined hourly for 20 hours beginning at hour 2. Using the validated method (D24 Version 00), dextroamphetamine and the internal standard, amphetamine-d5, were extracted from human plasma (200.0 µL), with potassium ethylenediaminetetraacetic acid ($K_2EDTA$) as an anticoagulant, by liquid-liquid extraction, evaporation under nitrogen, and reconstitution in 200.0 µL of mobile phase (0.05% Triflouroacetic Acid: Acetonitrile, 80:20, v/v). An aliquot of this extract was injected into a High Performance Liquid Chromatography (HPLC) system, detected using an API 3000 with HSID tandem mass spectrometer, and quantitated using peak area ratio method.

Method sensitivity and selectivity were achieved by detecting distinct precursor to product ion mass transitions for dextroamphetamine (136.2→119.1) and the internal standard, amphetamine-d5 (141.2→124.1), at defined retention times under reverse chromatographic conditions.

Evaluation of the assay, using defined acceptance criteria, was carried out by the construction of an eight (8) point calibration curve (excluding zero concentration) covering the range of 0.200 ng/mL to 51.200 ng/mL for dextroamphetamine in human plasma. The slope and intercept of the calibration curves were determined through weighted linear regression analysis (1/conc.$^2$). Two calibration curves and duplicate QC samples (at three concentration levels) were analyzed along with each batch of the study samples. Peak area ratios were used to determine the concentration of the standards, quality control samples, and the unknown study samples from the calibration curves.

Figure 17:
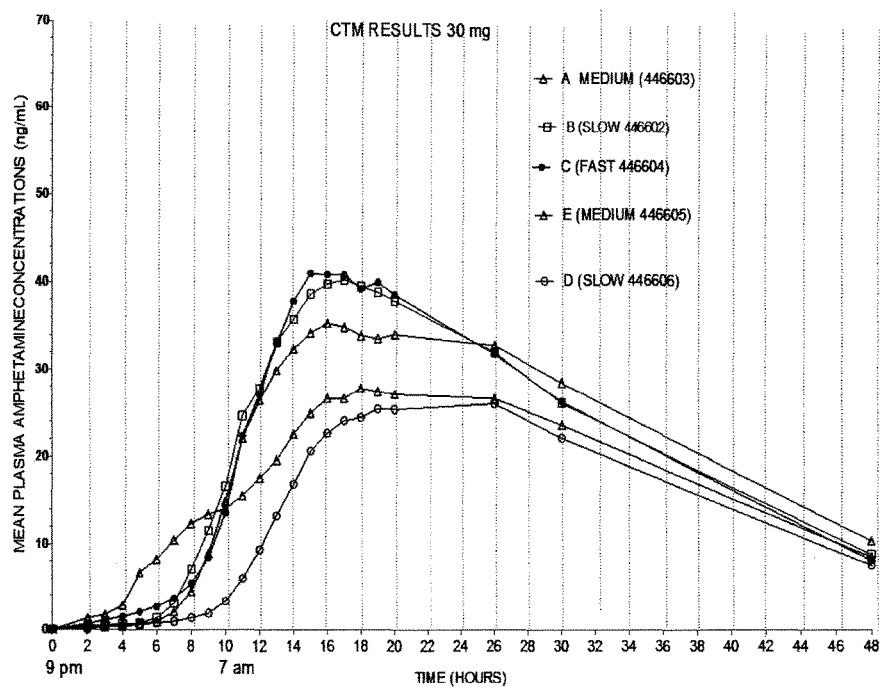
FIG. 17 is a graph of the plasma concentration of healthy volunteers after ingesting the formulations of Examples 14-18.
Figure 18:
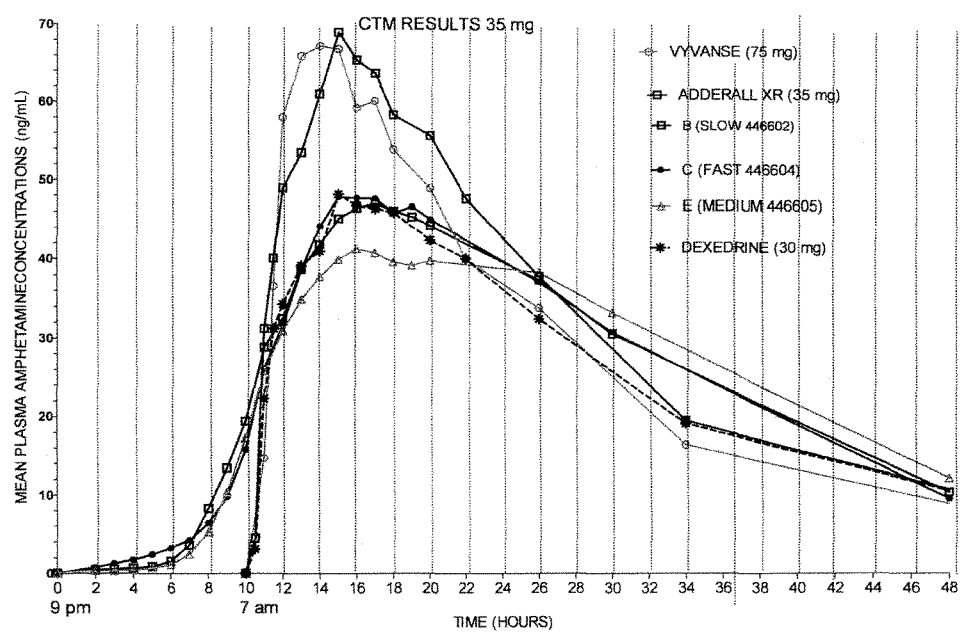
FIG. 18 is a comparison of the data of FIG. 17 with commercially available formulations.

The plasma concentrations are shown in FIG. 17, in which the beginning time of day is set to 9 PM. An overlay of the pharmacokinetic data of three commercial formulations, Dexedrine, Adderall® XR and Vyvanse® are overlayed with the data of FIG. 17 in FIG. 18.

As shown in the table below, at the early time points, 0-6 hours and 0-10 hours, exposure was highest for Treatment A and this correlated with the early dissolution observed for this formulation. Exposure from 0 to $T_{max}$ was marginally higher for Treatment A than the other treatments, but was more variable than Treatments B and C. Treatment C was higher than B but was more variable. For Treatment D the exposure 0 to $T_{max}$ was relatively high (considering total $AUC_{0-inf}$), but the Treatment D $T_{max}$ values occurred later than the other treatments.

TABLE 35

| | Dextroamphetamine Partial Exposure Metrics | | | | | | | |
|---|---|---|---|---|---|---|---|---|
| | $AUC_{0-6}$ (ng · hr/mL) | | $AUC_{0-10}$ (ng · hr/mL) | | $AUC_{0-Tmax}$ (ng · hr/mL) | | $AUC_{0-inf (ng/mL)}$ | |
| Treatment | Mean (N) | CV (%) | Mean (N) | CV (%) | Mean | CV (%) | Mean | CV (%) |
| A | 16.7 (10) | 29.9 | 63.8 (10) | 23.9 | 286.0 | 60.2 | 991.5 | 42.6 |
| B | 2.1 (12) | 78.8 | 32.9 (12) | 41.2 | 234.6 | 20.7 | 1142.4 | 16.7 |
| C | 6.5 (10) | 38.1 | 30.7 (10) | 40.5 | 278.5 | 37.4 | 1250.3 | 20.7 |
| D | 1.6 (12) | 44.7 | 7.3 (12) | 41.3 | 266.0 | 50.7 | 869.9 | 27.7 |
| E | 2.1 (12) | 33.3 | 27.3 (12) | 34.0 | 264.2 | 60.2 | 1069.5 | 35.8 |

The mean Tmax values for treatments A, B, C, D and E were 17.9, 16.4, 17.7, 22.6 and 17.8 hours, respectively.

The early exposure (0-6 hours and 0-10 hours) provided by these formulations was very low relative to $AUC_{0-inf}$ and is shown in the Table below together with $AUC_{0-Tmax}$ in terms of percentages of the mean values of these partial exposure metrics relative to mean values of $AUC_{0-inf}$ for each of the five treatments

TABLE 36

| Treatment | $AUC_{0-6}$ | $AUC_{0-10}$ | $AUC_{0-Tmax}$ |
|---|---|---|---|
| A | 1.7 | 6.4 | 28.8 |
| B | 0.1 | 2.9 | 20.5 |
| C | 0.5 | 2.5 | 22.3 |
| D | 0.2 | 0.8 | 30.6 |
| E | 0.2 | 2.6 | 24.7 |

The exposure was less than 2% for all treatments (0-6 hours) and less than 5% for the AUC (0-10 hours) except for Treatment A (6.4%).

Seventeen subjects experienced a total of 25 adverse events ("AEs") during the study. The most frequent AEs are expressed as fractions, relative to the total number of AEs experienced after each treatment.

No AE was reported more than once after administration of Treatment A [Dextroamphetamine Sulfate Capsule, 30 mg, CII (20% SR, 30% pH coat, Medium Release)], Treatment C [Dextroamphetamine Sulfate Capsule, 30 mg, CII (20% SR, 20% pH coat, Fast Release)] and Treatment D [Dextroamphetamine Sulfate Capsule, 30 mg, CII (25% SR, 30% pH coat, Slow Release)].

After administration of Treatment B (Dextroamphetamine Sulfate Capsule, 30 mg, CII (25% SR, 20% pH coat, Slow Release), the most frequently AEs were headache (2/7) and somnolence (2/7).

After administration of Treatment E [(Dextroamphetamine Sulfate Capsule, 30 mg, CII (20% SR, 20% pH coat, Medium Release)], the most frequently AE was dry mouth (2/8).

No AE was reported after the end-of-study exam.

Five AEs were "probably" related to the study drug, and 12 AEs were "possibly" related to the study drug. All subjects who experienced AEs during this study recovered completely.

No serious adverse events (SAEs) were reported.

Example 24

Composition of Methylphenidate, 54 mg Capsules (Slow Release Formulation, 25% SR Weight Gain+30% pH Dependent Weight Gain)

TABLE 37

| Component and Quality Standard (and Grade, if applicable) | Function | Strength (label claim) 54 mg | |
|---|---|---|---|
| | | Quantity per unit (mg) | % |
| Methylphenidate Hydrochloride, USP, CII | Active ingredient | 54.00 | 13.54 |
| Microcrystalline Cellulose, NF (Avicel PH-101) | Binder | 191.45 | 48.00 |
| Ethyl Cellulose, NF (Ethocel Standard 10 Premium) | Film Former | 30.16 | 7.56 |
| Hydroxypropyl Cellulose, NF (Klucel EF Pharm) | Film Former | 7.54 | 1.89 |
| Dibutyl Sebacate, NF | Film Plasticizer | 2.18 | 0.55 |
| Magnesium Stearate, NF | Hydrophobic Film Component | 21.48 | 5.39 |
| Methacrylic Acid Copolymer Type-B (Eudragit S 100) | Film Former | 74.19 | 18.60 |
| Mono-and Di-Glycerides, NF (Imwitor 900K) | Film Plasticizer | 7.46 | 1.87 |
| Dibutyl Sebacate, NF | Film Plasticizer | 7.46 | 1.87 |
| Polysorbate 80, NF | Solubilizer | 2.95 | 0.74 |
| Total | | 398.87 | 100.0 |

Example 25

Composition of Methylphenidate, 54 mg Capsules (Slow Release Formulation, 20% SR Weight Gain+20% pH Dependent Weight Gain)

TABLE 38

| Component and Quality Standard (and Grade, if applicable) | Function | Strength (label claim) 54 mg | |
|---|---|---|---|
| | | Quantity per unit (mg) | % |
| Methylphenidate Hydrochloride, USP, CII | Active ingredient | 54.00 | 15.28 |
| Microcrystalline Cellulose, NF (Avicel PH-101) | Binder | 191.45 | 54.16 |
| Ethyl Cellulose, NF (Ethocel Standard 10 Premium) | Film Former | 20.42 | 5.78 |
| Hydroxypropyl Cellulose, NF (Klucel EF Pharm) | Film Former | 5.11 | 1.45 |
| Dibutyl Sebacate, NF | Film Plasticizer | 1.48 | 0.42 |
| Magnesium Stearate, NF | Hydrophobic Film Component | 22.09 | 6.25 |
| Methacrylic Acid Copolymer Type-B (Eudragit S 100) | Film Former | 47.48 | 13.43 |
| Mono-and Di-Glycerides, NF (Imwitor 900K) | Film Plasticizer | 4.77 | 1.35 |
| Dibutyl Sebacate, NF | Film Plasticizer | 4.77 | 1.35 |
| Polysorbate 80, NF | Solubilizer | 1.89 | 0.53 |
| Total | | 353.46 | 100.0 |

Example 26

TABLE 39

Composition of Methylphenidate, 54 mg Capsules (Slow Release Formulation, 20% SR Weight Gain + 30% EC pH Dependent Weight Gain)

| Component and Quality Standard (and Grade, if applicable) | Function | Strength (label claim) 54 mg | |
|---|---|---|---|
| | | Quantity per unit (mg) | % |
| Methylphenidate Hydrochloride, USP, CII | Active ingredient | 54.00 | 15.95 |
| Microcrystalline Cellulose, NF (Avicel PH-101) | Binder | 162.00 | 47.84 |
| Ethyl Cellulose, NF (Ethocel Standard 10 Premium) | Film Former | 21.23 | 6.27 |
| Hydroxypropyl Cellulose, NF (Klucel EF Pharm) | Film Former | 5.31 | 1.57 |
| Dibutyl Sebacate, NF | Film Plasticizer | 7.84 | 2.32 |
| Magnesium Stearate, NF | Hydrophobic Film Component | 15.12 | 4.46 |
| Methacrylic Acid Copolymer Type-B (Eudragit S 100) | Film Former | 62.68 | 18.51 |
| Mono-and Di-Glycerides, NF (Imwitor 900K) | Film Plasticizer | 6.30 | 1.86 |
| Polysorbate 80, NF | Solubilizer | 2.49 | 0.74 |
| Talc | Encapsulation Lubricant | 1.68 | 0.50 |
| Total | | 338.65 | 100.0 |

TABLE 40

Composition of Methylphenidate, 54 mg Capsules
(Fast Release Formulation, 20% SR Weight
Gain + 15% EC pH Dependent Weight Gain)

| Component and Quality Standard (and Grade, if applicable) | Function | Strength (label claim) 54 mg Quantity per unit (mg) | % |
|---|---|---|---|
| Methylphenidate Hydrochloride, USP, CII | Active ingredient | 54.00 | 18.03 |
| Microcrystalline Cellulose, NF (Avicel PH-101) | Binder | 162.00 | 54.08 |
| Ethyl Cellulose, NF (Ethocel Standard 10 Premium) | Film Former | 21.23 | 7.09 |
| Hydroxypropyl Cellulose, NF (Klucel EF Pharm) | Film Former | 5.31 | 1.77 |
| Dibutyl Sebacate, NF | Film Plasticizer | 4.69 | 1.57 |
| Magnesium Stearate, NF | Hydrophobic Film Component | 15.12 | 5.05 |
| Methacrylic Acid Copolymer Type-B (Eudragit S 100) | Film Former | 31.34 | 10.46 |
| Mono-and Di-Glycerides, NF (Imwitor 900K) | Film Plasticizer | 3.15 | 1.05 |
| Polysorbate 80, NF | Solubilizer | 1.24 | 0.41 |
| Talc | Encapsulation Lubricant | 1.49 | 0.50 |
| Total | | 299.57 | 100.0 |

Example 27

Method of Processing Coated Methylphenidate Capsules

In a preferred manufacturing process, methylphenidate HCl and microcrystalline cellulose (Avicel PH-101) are blended in a Hobart Mixer. Purified water is added to the dry mixture and the wet granulation is extruded (MG-55 Multi granulator). The extrudate is then spheronized into pellets (Caleva Model# SPH250). The wet pellets are dried (Fluid Air Model# 0050) and sieved (30 mesh<Acceptable<20 mesh).

The sustained release coating is added as follows: a dispersion of Ethyl Cellulose NF (Ethocel Standard 10 Premium), Klucel EF, Dibutyl Sebacate, NF, magnesium stearate, NF, ethanol and purified water, USP is prepared in an overhead stirrer. The dispersion is applied to the uncoated methylphenidate pellets in the fluid bed and the coated pellets are sieved as before. It is understood that in this context of this example, the term "dispersion" can refer to various two phase systems in which at least some solids are dispersed in a liquid phase. The term "dispersion", as used herein, can thus include, but is in no way limited, either wholly or partly, the concepts of colloids, emulsions and/or suspensions.

The enteric coating is prepared as follows: a dispersion of Methacrylic Acid Copolymer Type B (Eudragit S100), Mono and di-glycerides, NF (Inwitor 900K), Dibutyl Sebacate, NF, Polysorbate 80, NF, ethanol and purified water, USP are mixed in an overhead stirrer to obtain a dispersion. The dispersion is applied to the sustained release coated methylphenidate pellets in the fluid bed. The enteric coated pellets are encapsulated to obtain the methylphenidate capsules.

Example 28

This example describes results of a randomized, single-center, single-dose, open-label, crossover, comparative bioavailability study in healthy adult volunteers. The study was designed to compare two methylphenidate HCl modified release formulations with each other, and with an immediate release, marketed formulation of methylphenidate HCl (Ritalin®).

This study compared 54 mg MPH00400 and 54 mg MPH00500, modified-release methylphenidate formulations, with 20 mg Ritalin®. A total of 12 subjects were randomly assigned to 3 treatment sequence cohorts of 4 subjects each, and received all 3 treatments in crossover fashion, with washout periods between treatment doses of approximately 4 days. The order of treatment administrations for Cohort I was Ritalin®, MPH00400, MPH00500; for Cohort II was MPH00400, MPH00500, Ritalin®; and for Cohort III was MPH00500, Ritalin®, MPH00400.

MPH00400 consists of a slow-release capsule (20% sustained-release coating, 30% pH coat, slow release) of 54 mg methylphenidate as well as microcrystalline cellulose, ethyl cellulose, hydroxypropyl cellulose, dibutyl sebacate, magnesium stearate, methacrylic acid copolymer type-B (Eudragit S 100), mono- and diglycerides, dibutyl sebacate and polysorbate 80 (total capsule weight: 338.65 mg). The formulation is described in more detail in Table 39 in Example 26.

MPH00500 consists of a fast-release capsule (20% sustained-release coating, 15% pH coat, fast release) of 54 mg methylphenidate as well as microcrystalline cellulose, ethyl cellulose, hydroxypropyl cellulose, dibutyl sebacate, magnesium stearate, methacrylic acid copolymer type-B (Eudragit S 100), mono- and diglycerides, dibutyl sebacate and polysorbate 80 (total capsule weight: 299.57 mg). The formulation is described in more detail in Table 40 in Example 26.

MPH00400 and MPH00500 were administered orally with 240 mL room temperature water at approximately 9 PM, at least 3 hours after consuming a low-fat dietary supplement meal (350-450 kcal). For the purpose of this study, subjects were considered to be in the fasted state.

Blood samples for pharmacokinetic analysis were collected during the treatment phase of the study. During treatment with Ritalin®, blood samples were collected 10 minutes predose and at 0.25, 0.5, 1, 1.5, 2, 2.5, 3, 3.5, 4, 5, 6, 8, 10, 12, 14, 17, 20 and 24 hours postdose. For treatment with MPH00400 and MPH00500, blood samples were collected 10 minutes predose and at 2, 3, 4, 5, 6, 7, 8, 9, 10, 11, 12, 13, 14, 15, 16, 17, 18, 19, 20, 24, 30, 36 and 48 hours postdose.

MPH00400 and MPH00500 are investigational modified-release formulations of methylphenidate hydrochloride that have differing dissolution release rates (slow and fast, respectively). The formulations consist of coated drug particles (in the form of pellets) in a water-soluble capsule shell. The pellets are coated with an outer delayed-release coating and an inner sustained-release coating over a drug-containing core, with each unit capsule containing 54 mg methylphenidate. Two film-coated bead formulations have been developed for clinical study, the compositions of which differ, to achieve a range of release profiles (slow release for MPH00400 and fast release for MPH00500).

Pharmacokinetic parameters for plasma methylphenidate were calculated using noncompartmental analyses, including:

$AUC_{0-t}$: Area under the plasma concentration-time curve to time point t (ng*h/mL), in which t is the last time point over the time interval with a measurable drug concentration;

$AUC_{0-\infty}$: AUC to infinite time (ng*h/mL);
$C_{max}$: Maximum drug concentration in plasma (ng/mL);
$T_{max}$: Time to reach maximum concentration (h);
λz: Terminal elimination rate constant (hr-1);
$t_{1/2}$: Half-life of elimination (h).

For bioequivalence testing, $C_{max}$ values and $AUC_{0-t}$ values were dose-normalized by dividing the individual value of the parameter by the weight of the drug administered (mg) for the treatments.

To explore the influence of subject weight on observed pharmacokinetic exposure, the individual total exposure ($AUC_{0-t}$) and peak exposure ($C_{max}$) were normalized (corrected) for body weight. This process of deriving the body weight corrected exposure ("DWN") involved dividing the value of individual parameters by the dose administered to the subject in terms of mg/kg body weight.

Figure 19:
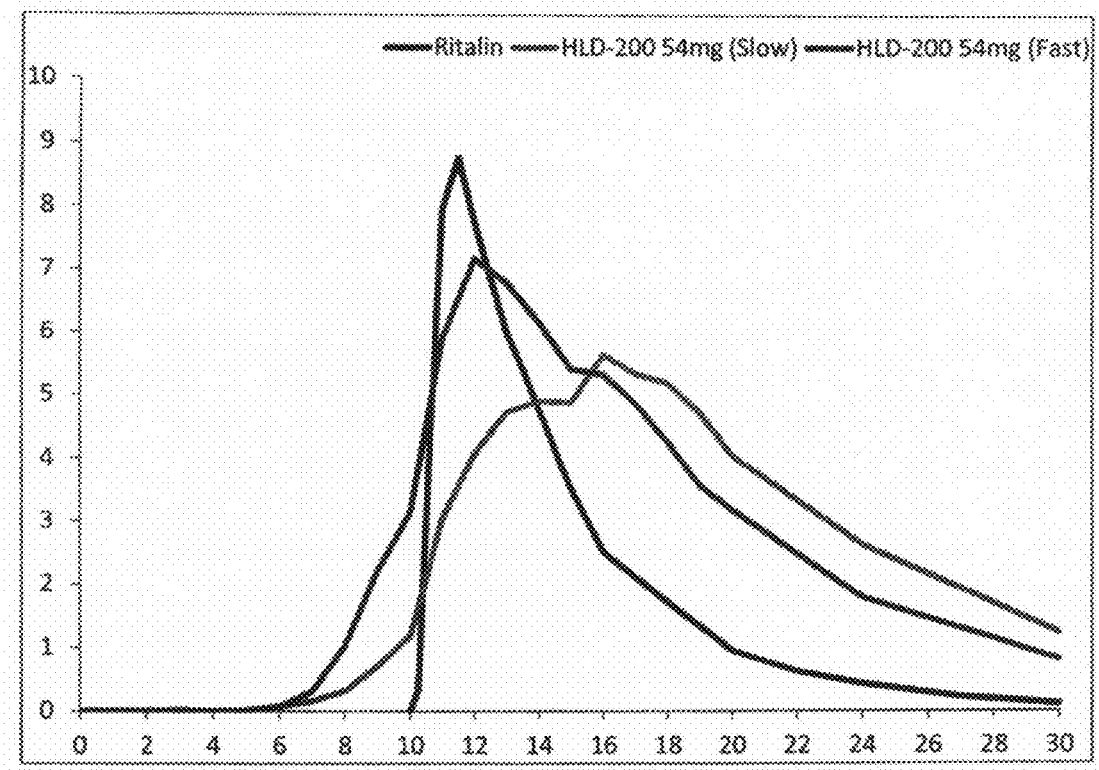
FIG. 19 is a comparison of mean plasma concentration of commercially available Ritalin® with the methylphenidate test formulas as described in Example 28.

Table 41 presents results of pharmacokinetic analyses for the PK evaluable analysis set. Reliable $AUC_{0-\infty}$ could not be obtained for MPH00400 or MPH00500 because of the formulations' late drug absorptions, which interfered with evaluation of the terminal elimination rate constant. The $AUC_{0-t}$ parameter (24 hours for Ritalin®, 48 hours for MPH00400 and MPH00500) was considered to be a reliable measure of total exposure for all treatments. This parameter was used as the relative measure of total drug exposure for MPH00400 and MPH00500. A graph of the PK data is shown in FIG. 19.

Generally, the trend of mean concentration time values was representative of the individual subjects within a treatment. MPH00400 was more slowly absorbed than MPH00500 (83.4 ng*h/mL vs. 82.6 ng*h/mL, respectively), but Cmax for MPH00500 was higher than that for MPH00400 (7.48 ng/mL vs. 5.99 ng/mL, respectively), with a later $T_{max}$ value for MPH00400 (15.58 h vs. 13.0 h for MPH00500).

The dose level of Ritalin® used in the study (20 mg) was selected with the intention of matching an estimate of the expected peak $C_{max}$ that would be provided by the 54-mg experimental formulations. The mean $C_{max}$ value observed for Ritalin® treatment (8.9 ng/mL), however was 19% higher than the observed mean value observed for MPH00500 (7.48 ng/mL) and 49% higher than that observed for MPH00400 (5.99 ng/mL).

Mixed model analysis of methylphenidate parameters comparing MPH00400 and MPH00500 with each other and to Ritalin® demonstrated that the relative dose-normalized bioavailability in terms of the mean of individual ratios for $C_{max}$ of MPH00400 and MPH00500 to Ritalin® was 25% and 30%, respectively. Based on the geometric mean ratios for $AUC_{0-t}$, relative dose-normalized bioavailability compared with Ritalin® was 73% and 72% for MPH00400 and MPH00500, respectively.

TABLE 41

Summary of Methylphenidate HCl Parameters, Pharmacokinetic Evaluable Analysis Set

| Treatment | | $C_{max}$ (ng/ml) | $T_{max}$ (h) | $AUC_{0-t}$ (ng*hr/mL) |
|---|---|---|---|---|
| MPH00400 | Mean ± SD (n) | 5.99 ± 1.44 | 15.58 ± 1.73 | 83.4 ± 22.6 |
| | Range (min, max) | 3.93, 8.66 | 13.0, 18.0 | 43.0, 129.8 |
| | Median | 5.85 | 16.0 | 80.0 |
| | CV % | 24.0 | 11.1 | 27.1 |
| MPH00500 | Mean ± SD (n) | 7.48 ± 2.96 | 13.0 ± 2.04 | 82.6 ± 23.1 |
| | Range (min, max) | 3.92, 12.50 | 11.0, 17.0 | 52.3, 132.3 |
| | Median | 5.94 | 12.0 | 81.9 |
| | CV % | 39.6 | 15.7 | 28.0 |
| IR METHYL-PHENIDATE HCl | Mean ± SD (n) | 8.90 ± 2.40 | 1.54 ± 0.40 | 42.0 ± 10.4 |
| | Range (min, max) | 5.92, 15.09 | 1.0, 2.5 | 26.4, 61.0 |
| | Median | 8.55 | 1.50 | 40.0 |
| | CV % | 27.0 | 25.7 | 24.8 |

Following evening administration of MPH00400 and MPH00500, there was a delay of approximately 6 hours prior to drug release the next morning. Exposure characteristics for both MPH00400 and MPH00500 were highly extended throughout the day, but were even more extended for MPH00400, with a later mean Tmax value for MPH00400 compared with that for MPH00500 (15.58 h vs. 13.0 h). The mean Cmax value for Ritalin® was 19% higher than for MPH00500 and 49% higher than that for MPH00400.

The PK data for the MPH00400, slow release formulation was also compared to published PK data for a sustained release, marketed formulation of methylphenidate HCl, (Concerta®). The dosage strength of 80 mg MPH00400 was chosen as the equivalent of 54 mg of Concerta®. The parameters for the 80 mg dose are calculated from the 54 mg dose data based on a linear equivalence dosage model.

The comparison of the test formulation MPH00400 calculated to reflect an 80 mg dose and the published Concerta® PK profile is shown in FIG. 20, again as mean plasma concentrations vs. time in hours. Eighty mg was chosen as the equivalent because the test formula is absorbed much lower in the GI tract and may have decreased bioavailability. The comparisons demonstrate the pharmacokinetic equivalence of the reference and test formulations.

Figure 20:
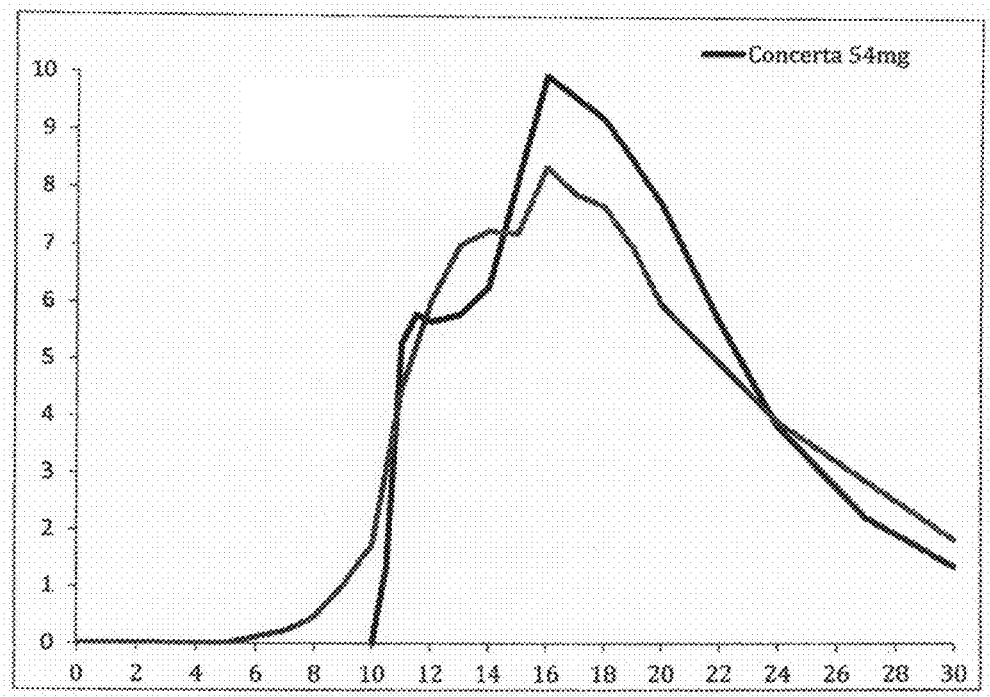
FIG. 20 is a comparison of mean plasma concentration of commercially available Concerta® with the methylphenidate test formulas as described in Example 28.
Figure 21:
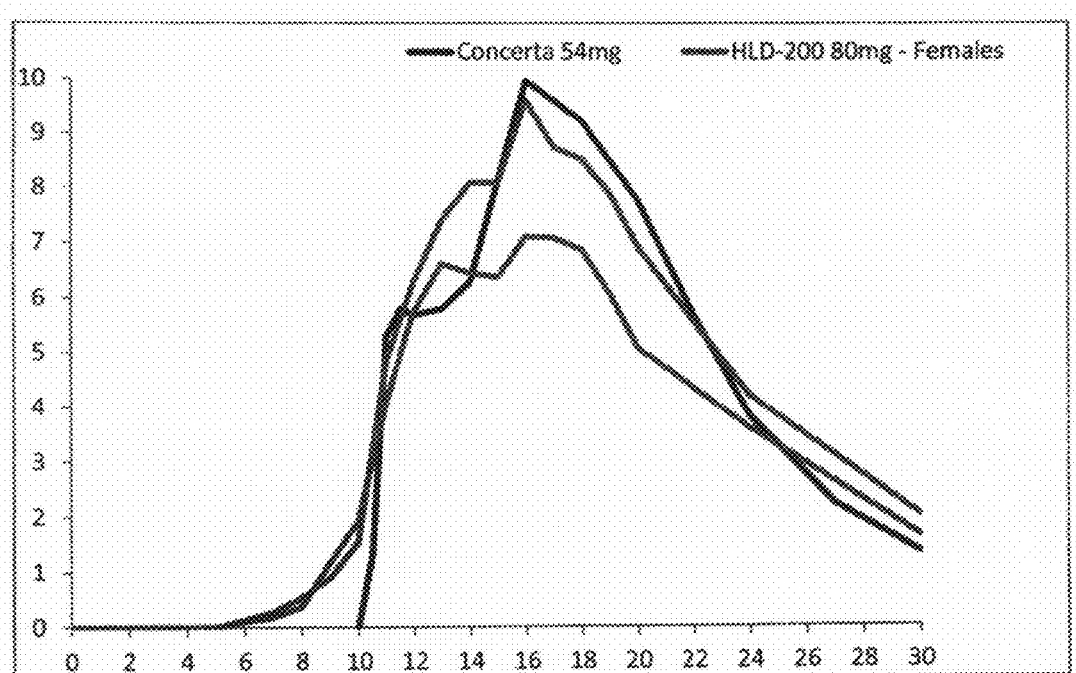
FIG. 21 is a graph showing the gender effect in the comparison with Concerta® from Example 28.
Figure 22:
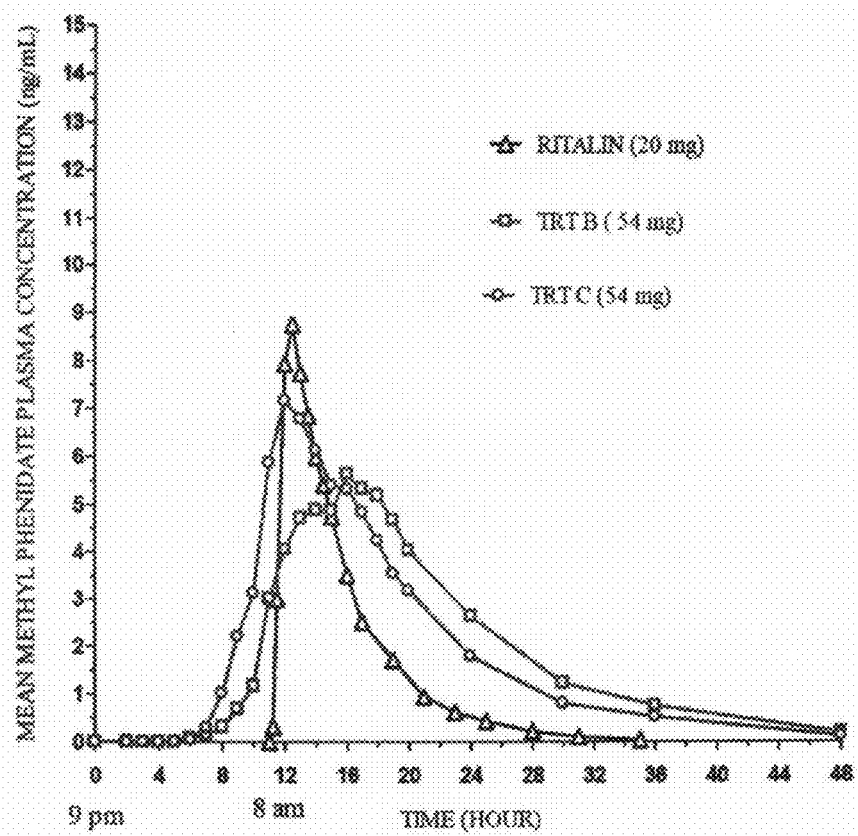
FIG. 22 is a comparison of mean plasma concentration time values for the modified release (MR) formulations MPH004 and MPH005 and the reference Ritalin® described in Example 28.

FIG. 21 shows the data as in FIG. 20 with the test subjects broken into two groups based on gender. The plasma levels are lower in the female group, presumably due to the faster metabolism expected in female subjects.

TABLE 42

Comparison of test formulation MPH00400 calculated to reflect an 80 mg dose and the published Concerta ® PK profile

| | $C_{max}$ (ng/ml) | CV (%) | $T_{max}$ (hrs) | CV (%) | AUC (ng · h/mL) | CV (%) |
|---|---|---|---|---|---|---|
| Concerta ® (54 mg) | 10.5 | 32.4 | 7.2 | 20.8 | 118.9[§] | 38.6 |
| MPH 00400 *(54 mg) | 5.99 | 24.0 | 15.6 | 11.1 | 83.4[§] | 27.1 |
| MPH 00400 (80 mg)** | 8.87 | 24.0 | 15.6 | 11.1 | 123.6[§] | 27.1 |

*MPH00400 was the selected formulation for the HLD200 product for further development
**Linear dose extrapolation from 54 mg doses
[§]For Concerta ® $AUC_{0-inf}$ is shown from FDA Clin. Pharm. Review, for HLD200 $AUC_{0-t}$ is shown where τ was 48 hours
$C_{max}$ Maximum plasma drug concentration post dose
$T_{max}$ Time to maximum plasma concentration
CV Coefficient of variation

Example 29

This example describes a Phase I, single center clinical trial examining the pharmacokinetic effects of 100 mg of HLD200 modified release formulations of methylphenidate in healthy adult volunteers in a fasted, fed and sprinkled state under a randomized three-way crossover design. The objective of the study is to determine the rate and extent of absorption (i.e., PK) of HLD200 modified release (MR) following single treatment (B-HLD200) in healthy adult volunteers in fasted, fed, and sprinkled states as well as tolerability in healthy adult volunteers.

Single-treatment B-HLD200 (100 mg) administered p.o. in the late evening, at approximately 9 PM with 240 ml of ambient temperature water following a fasted state, following a high fat meal, and when sprinkled in applesauce randomly crossed over to different treatment sequences in 6 cohorts with 7 days of washout between treatment periods. PK parameters $C_{max}$, $T_{max}$ and AUC are shown in Table 41 for all subjects and separated by gender.

Figure 23:
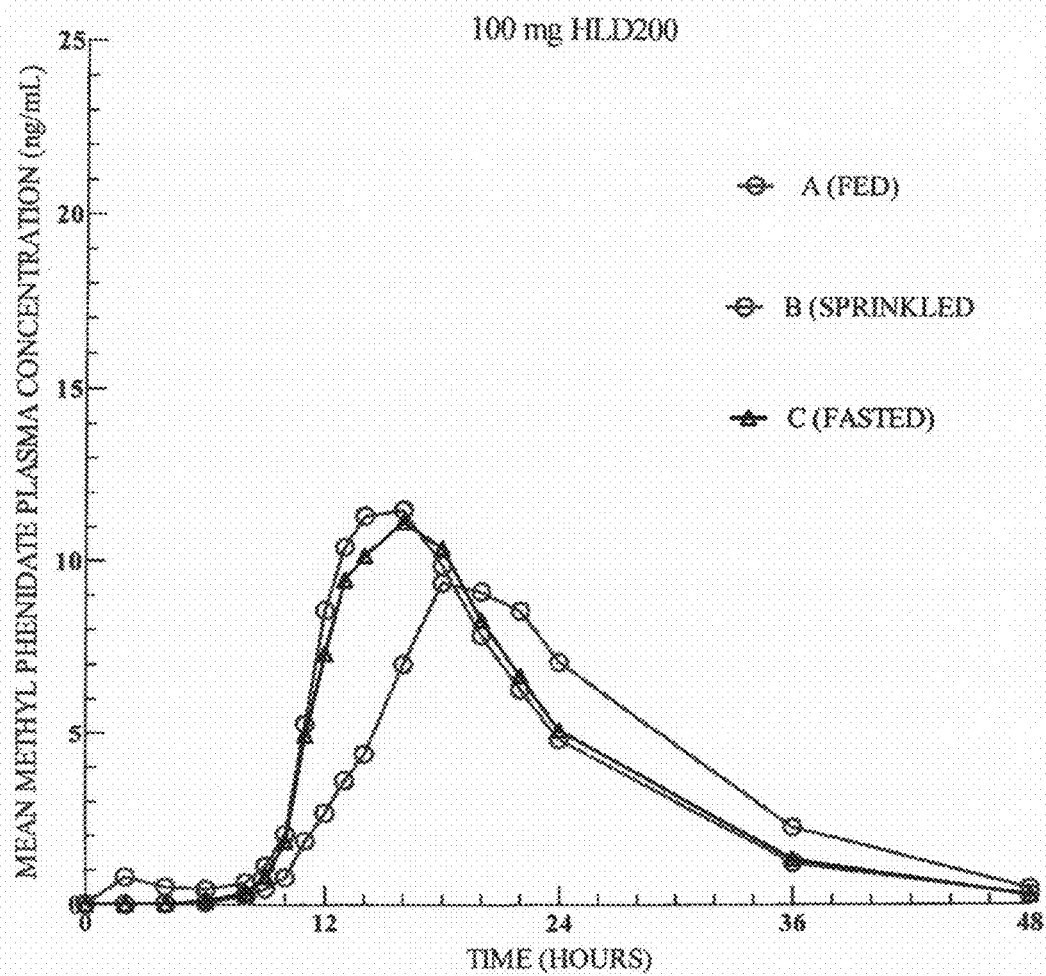
FIG. 23 is a comparison of mean plasma concentration time values for a 100 mg dose of HLD200 taken in a fed state, a fasted state and sprinkled on apple sauce as described in Example 29.
Figure 24:
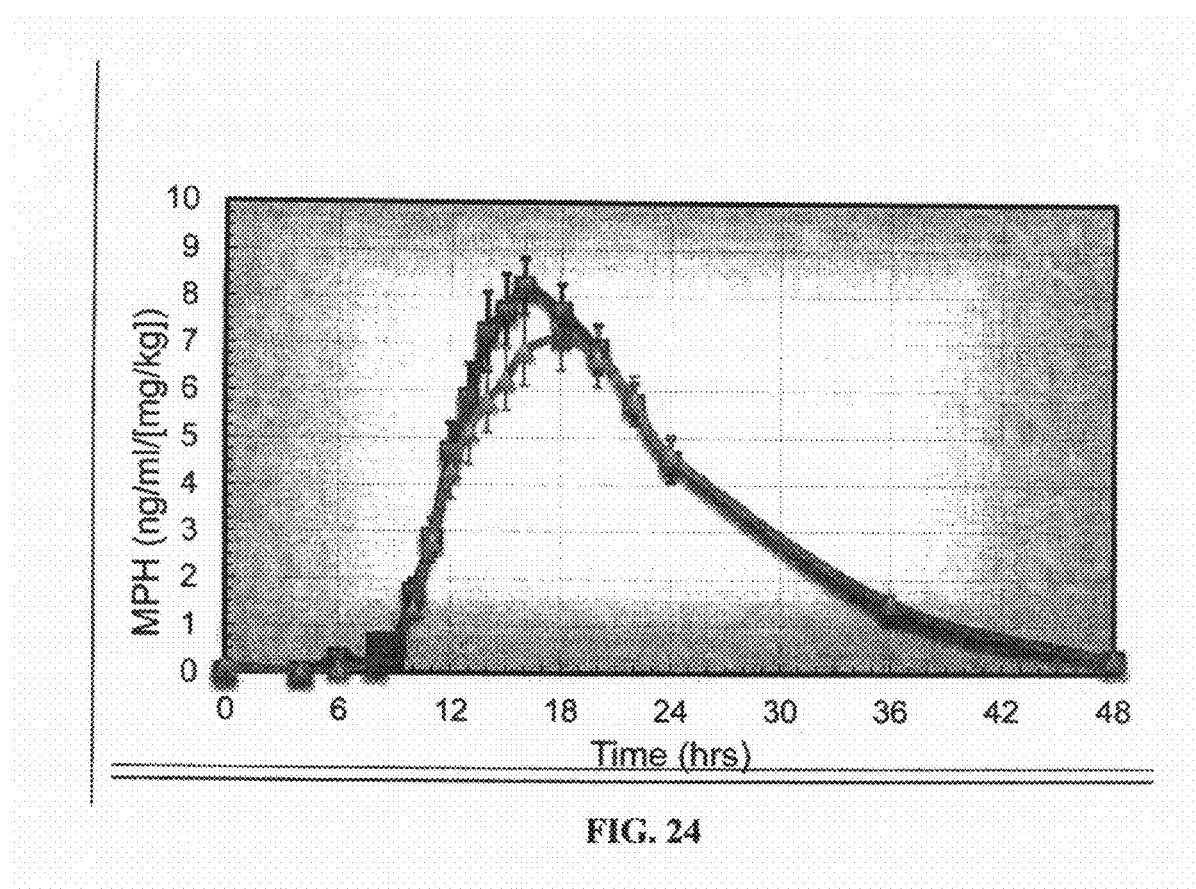
FIG. 24 is mean plasma concentration time values for adolescent and pediatric subjects after administration of MR methylphenidate as described in Example 30.

A graph of the mean plasma concentration time values is shown in FIG. 23. It can be seen that the PK curves exhibit lag and exposure profiles similar to those in the reported adult clinical trials described above, which were conducted in a fasted state.

TABLE 43

Mean Methylphenidate Pharmacokinetic Parameters following Administration of 100 mg HLD200 to Adult Normal Volunteers in the Fed, Sprinkled on Food and Fasted States

| PK Parameter | Treatment A (Fed) 100 mg | Treatment B (Sprinkled) 100 mg | Treatment C (Fasted) 100 mg |
|---|---|---|---|
| Lagtime (hr) ± CV (%) | | | |
| All Subjects [N] | 5.30 ± 51.6 [17] | 0.56 ± 240.5 [18] | 4.5 ± 41.9 [18] |
| Female ♀ [N] | 4.86 ± 52.5 [7] | 0.00 [7] | 4.0 ± 28.9 [7] |
| Male ♂ | 5.60 ± 52.6 [10] | 0.91 ± 180.1 [11] | 4.82 ± 46.2 [11] |
| $C_{max}$ ± CV (%) | | | |
| All Subjects [N] | 10.65 ± 43.5 [17] | 12.58 ± 33.8 [18] | 12.5 ± 31.4 [18] |
| Female ♀ [N] | 13.15 ± 44.7 [7] | 14.99 ± 32.4 [7] | 15.41 ± 29.1 [7] |
| Male ♂ [N] | 8.69 ± 29.2 [10] | 11.04 ± 28.5 [11] | 10.64 ± 19.8 [11] |
| Median $T_{max}$ (hr) | 18.0 | 15.02 [18] | 15.06 [18] |
| All Subjects [N] Range | 14-22 [17] | 12-16.0 [18] | 12-20 [18] |
| Female ♀ [N] | 18.00 [7] 18-22 [7] | 16.00 [7] 14-18 [11] | 16.00 [7] 13-18 [11] |
| Male ♂ [N] | 19.00 [10] 14-22 [10] | 14.5 [7] 12-16 [11] | 14.0 [7] 12-20 [11] |
| $AUC_{0-t}$ ± CV (%) (ng•hr/mL) | | | |
| All Subjects [N] | 164.3 ± 41.3 [17] | 169.7 ± 37.2 [18] | 166.5 ± 27.7 [18] |
| Female ♀ [N] | 197.3 ± 41.7 [7] | 208.1 ± 35.4 [7] | 191.6 ± 29.7 [7] |
| Male ♂ [N] | 141.2 ± 33.6 [10] | 145.2 ± 29.4 [11] | 150.6 ± 20.6 [11] |
| $AUC_{0-inf}$ ± CV (%) (ng•hr/mL) | | | |
| All Subjects [N] | 169.2 ± 41.5 [17] | 173.2 ± 36.6 [18] | 169.2 ± 27.6 [18] |
| Female ♀ [N] | 202.5 ± 42.0 [7] | 212.1 ± 35.0 [7] | 194.4 ± 29.0 [7] |
| Male ♂ [N] | 145.8 ± 34.1 [10] | 148.5 ± 28.5 [11] | 153.1 ± 21.4 [11] |

Example 30

A multiple-cohort, open-label, single-dose, fasting study of methylphenidate 54 mg capsules was conducted, administering a single formulation to 18 adolescent (aged 13-17) and 11 pediatric (aged 6-12) subjects diagnosed with ADHD. Formulations were administered orally during the trial.

A graph of the plasma methylphenidate concentrations for adolescent and pediatric subjects are shown in FIG. 23, in which the beginning time of day is set to 9 PM (t=0 hours). The data is presented as dose-weight adjusted pharmacokinetic data for both adolescent and pediatric populations described above.

The mean values for the $AUC_{0-10}$, $AUC_{0-Tmax}$, $AUC_{0-t}$ and $AUC_{0-inf}$ in pharmacokinetic parameters for the adolescent subjects are presented below in Table 44. This comparison serves to highlight that significant drug release does not occur between the 9 PM administration of the drug and 7 AM the next morning.

TABLE 44

Comparison of Mean Values for Methylphenidate Partial Exposure Metrics (Adolescents)

| | Subject | | | |
|---|---|---|---|---|
| | $AUC_{0-10}$ | $AUC_{0-Tmax}$ | $AUC_{0-t}$ | $AUC_{0-inf}$ |
| | | •(ng•hr/mL) | | |
| Mean | 1.1 | 32.1 | 105.5 | 109.6 |
| SD | 0.73 | 10.0 | 31.6 | 33.8 |
| CV % | 65.6 | 31.3 | 30.0 | 30.8 |

The mean values for the $AUC_{0-10}$, $AUC_{0-Tmax}$, $AUC_{0-t}$ and $AUC_{0-inf}$ in children are shown below in Table 45. These data again highlight the lack of significant release of drug for up to 10 hours following administration (9 PM-7 AM).

TABLE 45

Comparison of Mean Values for Methylphenidate Partial AUC Exposure Metrics (Children)

| | Subject | | | |
|---|---|---|---|---|
| | $AUC_{0-10}$ | $AUC_{0-Tmax}$ | $AUC_{0-t}$ | $AUC_{0-inf}$ |
| | | •(ng•hr/mL) | | |
| Mean | 2.7 | 61.3 | 205.5 | 210.1 |
| SD | 1.6 | 22.3 | 80.4 | 80.9 |
| CV % | 58.1 | 36.5 | 39.1 | 38.5 |

A summary of the primary pharmacokinetic parameters from the adolescents, children and adults (previous first-in-man study) is shown in the Table 46 below. The dose body weight normalization of the mean $AUC_0$-t and $C_{max}$ parameters shows that the three groups exhibited close similarity, but the mean dose body weight normalized $C_{max}$ for the children was lower than the adolescents by 16% and lower than the adults by 18.5%. However, the corresponding values for the dose body weight normalized $AUC_{0-t}$ were almost the same for the three groups. The $T_{max}$ parameter appeared to be occurring later (18.2 v 16.2 hours) in the children compared with the adolescents, but there no was statistical difference between the two groups using the Mann Whitney non parametric test. The adult $T_{max}$ data set was different from the children (p=0.03) but not different from the adolescents.

TABLE 46

Comparison of Mean Methylphenidate Pharmacokinetic Parameters from Groups

| Parameter | Adolescents N = 18 | Children N = 11 | Adults N = 12 |
|---|---|---|---|
| Mean $C_{max}$ (ng/mL) ± CV (%) | 7.17 ± 23.7 | 11.64 ± 36.3 | 5.99 ± 24.0 |
| Median Tmax (Range) | 16.3 (13.9-22.1) | 18.2 (12.4-22.0) | 16.0 (13-18) |
| Mean $AUC_{0-t}$ ± ng•hr/mL [CV (%)] | 105.5 ± 30.0 | 205.5 ± 39.1 | 83.4 ± 27.1 |
| Mean AUC0-inf ± CV (%) | 109.6 ± 30.8 | 210.1 ± 38.5 | † |
| DWN* parameters | | | |
| Mean $C_{max}$ (ng/mL)/ [mg/kg] ± CV (%) | 8.84 ± 34.5 | 7.44 ± 30.1 | 9.13 ± 35.2 |
| Mean $AUC_{0-t}$ (ng/mL/) [mg/kg] ± CV (%) | 129.4 ± 34.8 | 129.7 ± 27.3 | 126.5 ± 35.5 |
| Mean $AUC_{0-inf}$ (ng/mL/) [mg/kg] ± CV (%) | 134.4 ± 35.7 | 132.7 ± 27.2 | † |

*dose in mg divided by body weight
† no data available

Ten of 18 adolescent subjects treated with HLD200 experienced a total of 10 adverse events ("AEs") during the study. Six of 11 pediatric subjects experience a total of 7 AEs. Upper abdominal pain and upper respiratory infection were both reported by two adolescent subjects who were treated with HLD200, but no other AE was reported more than once in this patient population. Both dizziness and pharyngitis were reported in 2 pediatric subjects treated with HLD200, but no other AE was reported more than once in this patient population. No adolescent subject reported dizziness and no pediatric subject reported abdominal pain as AEs.

There were 5 treatment emergent adverse events (TEAEs), all mild in severity, in the adolescent population thought to be possibly or probably drug-related, and included upper abdominal pain (2 occurrences), headache, vomiting and flatulence (one occurrence each). There were no TEAEs in the pediatric population. There were no serious adverse events (SAEs) in either population.

Example 31

Dissolution of the fast, medium and slow release methylphenidate formulations with varying coating thicknesses was tested under conditions that simulate oral administration. As described above the conditions include the USP Apparatus I (Baskets) with agitation and placing the composition in 700 ml aqueous solution of 0.1N HCl pH 1.1, for up to 2 hours followed by 2-6 hours in sodium phosphate buffer at pH 6.0; followed by 6-20 hours in sodium phosphate buffer, pH 7.2, adding NaOH to adjust pH to 7.2.

Figure 25:
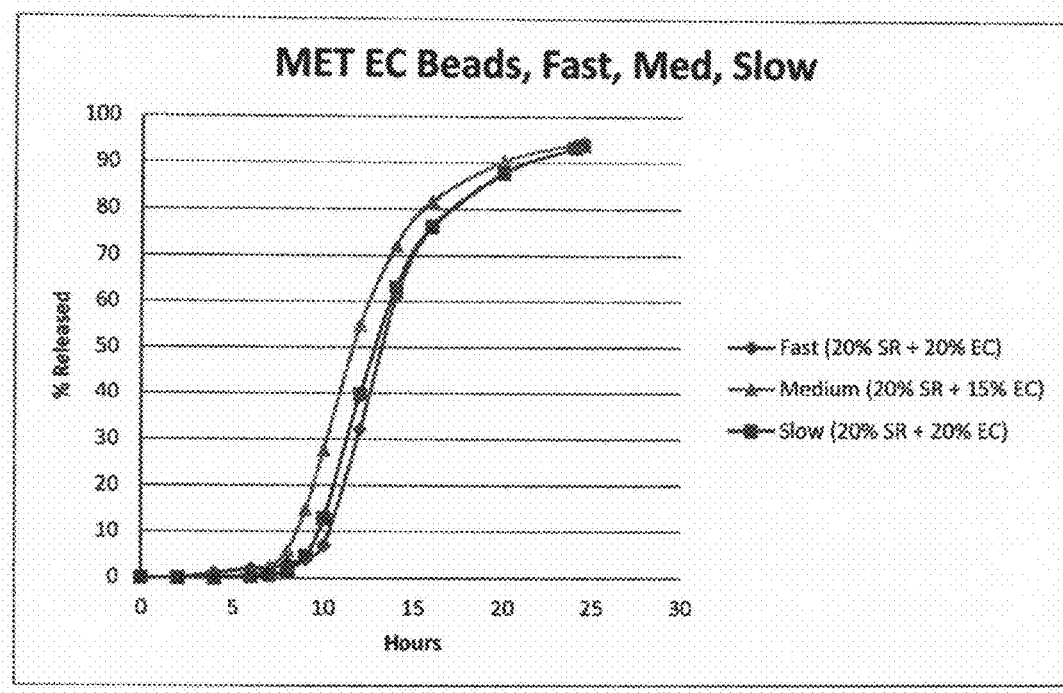
FIG. 25 is a graph of the dissolution results for 2 formulations, (i) a fast release formulation with a 20% weight gain SR coating and a 15% weight gain EC coating, and (ii) a slow release formulation with a 20% weight gain SR coating and a 30% weight gain EC coating.

FIG. 25 is a graph of the dissolution results for 2 formulations, (i) a fast release formulation with a 20% weight gain SR coating and a 15% weight gain EC coating, and (ii) a slow release formulation with a 20% weight gain SR coating and a 30% weight gain EC coating. As shown in the figure, the two formulations demonstrated at least an 8 hour lag in which there was no significant drug release and the lag is followed by a sustained release period of 10-12 hours.

Example 32

A Phase III Clinical Endpoint Evaluation Study was conducted examining the safety and efficacy of two formulations of evening-dosed, delayed and extended release methylphenidate in pediatric subjects with Attention-Deficit Hyperactivity Disorder. The intent was to assess the drug's safety, efficacy profile for control of ADHD symptoms during the morning routine and throughout the day in a target population. Forty eight patients between the ages of 6-12 years old with ADHD were enrolled and 43 (23 males, 20 females) were dosed, randomized and completed all study procedures The CEES consisted of a 6-week treatment-optimization period which allowed suitable time to titrate over the entire dosing range (20 mg, 40 mg, 60 mg, 80 mg and 100 mg), and adjust dose time (9:00 PM±2 hrs) if required, followed by a one week, double-blind, placebo-controlled, parallel-group assessment.

The drug administered during the trial was MPH Hydrochloride Capsules, 54 mg, (20% SR, 30% pH coat, slow release), which is the Ironshore MPH00400 slow release formulation. MPH00400 consists of a slow-release capsule (20% sustained-release coating, 30% pH coat, slow release) of methylphenidate as well as microcrystalline cellulose, ethyl cellulose, hydroxypropyl cellulose, dibutyl sebacate, magnesium stearate, methacrylic acid copolymer type-B (Eudragit S 100), mono- and diglycerides, dibutyl sebacate and polysorbate 80 (total capsule weight: 338.65 mg). The formulation is described in more detail in Table 39 in Example 26. This formulation (B-HLD200) of 54 mg capsules was modified to produce 20 and 40 mg capsules for the purpose of the study. Individual subject's daily doses (20, 40, 60, 80 and 100 mg) were achieved utilizing units of 20 and/or 40 mg MPH capsules, as required, to achieve their daily treatment dose level.

The primary endpoint for the study was to demonstrate whether evening treatment with HLD-200 improves control of ADHD symptoms, compared to placebo, from 8:00 am to 4:00 pm as measured by the Swanson, Kotkin, Agler, M-Flynn and Pelham (SKAMP) Rating Scale Combined Score (CS) administered during the Laboratory Classroom Test Day at the end of the Treatment/Test Phase. Secondary measures assessed during the Laboratory Classroom Test Day were the SKAMP CS during the evening at 6 pm and 8 pm, and the Permanent Product Measure of Performance (PERMP) Combined Score (Math problems Attempted+ Completed).

Secondary measures assessed prior to conducting the Laboratory Classroom for the period during the last half of the 7-day, double blind, placebo-controlled treatment period were Conners' Global Index-Parent (CGI-P) Total Score, Clinical Global Impression (CGI) of Severity and Improvement (CGI-S and CGI-I) Score, ADHD Rating Scale on DSM-IV criteria (ADHD-RS-IV) Total Score, and Parents Rating of Evening and Morning Behavior-Revised (PREMB-R). The Before School Function Questionnaire (BSFQ) Total Score was used to evaluate control of ADHD symptoms and improved function during the at-home morning routine.

The BSFQ scale was developed to assess commonly reported areas of morning dysfunction in children and adolescents with ADHD (Wilens, et al., 2010; 2013). There are two components of the BSFQ scale: a 20-item questionnaire completed by the clinician and/or the parent/guardian; and a 14-item self-report section completed by the subject in collaboration with the parent/guardian. Both components are focused primarily on early morning, before school functioning from approximately 6 AM to 9 AM. The 20-items BSFQ questionnaire, which is utilized in this study, has been validated and shown to be reliable. It is rated on a Likert Scale from 0 to 3; using the following rating methodology for symptom severity and functional impairment: 0=None; 1=Mild—somewhat different than peers/siblings, some days; 2=Moderate—different than peers/siblings, most days; and 3=Severe—different from peers all days, all settings. In addition, the rater is asked to record the following early morning time management information: 1) Time to wake up and get out of bed: x (min) and 2) Time to complete routines (from out of bed to exit home): x (min). The 14-item self-report component has not yet demonstrated validity or reliability, and was included as an endpoint in this study. As such, all references to the BSFQ in this protocol are specific to the 20-item scale only.

Parents are instructed to complete the BSFQ on the final two school day mornings (i.e., between Monday and Friday) prior to their child's weekly study visit and to review the results with the Investigator at that visit. Based on this review, the Investigator then completes the BSFQ scale for the combined two-day early morning period. These clinician-rated BSFQ assessments are completed at each of Visits 2, 3, 4, 5, 6, 7, 8 and 9 and the total score is recorded in the CRF.

PERMP (Swanson, 1998) is a 10-minute written math test performed as seatwork in the laboratory school analog classroom. Subjects are given five pages of 80 math problems, and are instructed to work at their desks and to complete as many problems as possible in 10 minutes. Performance is measured by the number of math problems attempted (PERMP-A) and the number of math problems correctly completed (PERMP-C). Different levels of the math tests are used among the subjects to adjust for ability as determined by the math pretest done at Visit 2 and practice class session at Visit 8. In addition, different versions of the math tests for a given level are used across class sessions (or cycles), so that a subject does not take the same test more than once during a day. A stopwatch is used to time the test. Like SKAMP, PERMP is collected during the final test Visit 9. In this study, both PERMP-A and PERMP-C are defined as secondary efficacy measures.

The SKAMP rating scale (Wigal and Wigal, 2006) is a 13-item independent observer rating of subject impairment (7-point scale) of analog classroom-observed behaviors during the laboratory school assessments. Items 1-4 represent an indication of subject attention (SKAMP-AS), items 5-8 are an indication of deportment (SKAMP-DS), items 9-11 assess quality of work, and items 12-13 assess subject compliance with teacher and classroom rules. In this study, the total score of all SKAMP items (or SKAMP combined score) is defined as the primary efficacy parameter.

The SKAMP rating scale is collected during each of 8 class sessions at Visit 9, occurring at 8, 9, 10 AM, and 12, 2, 4, 6, 8 PM of the laboratory school assessment day. The primary efficacy endpoint is defined as the SKAMP combined scores obtained from 8 AM through 4 PM sessions in this study, and secondary endpoints include results of testing at hours 6 and 8 PM to examine the extended time course of the treatment effectiveness. Practice class sessions for the laboratory school assessment day are conducted at Visit 8.

Figure 26:
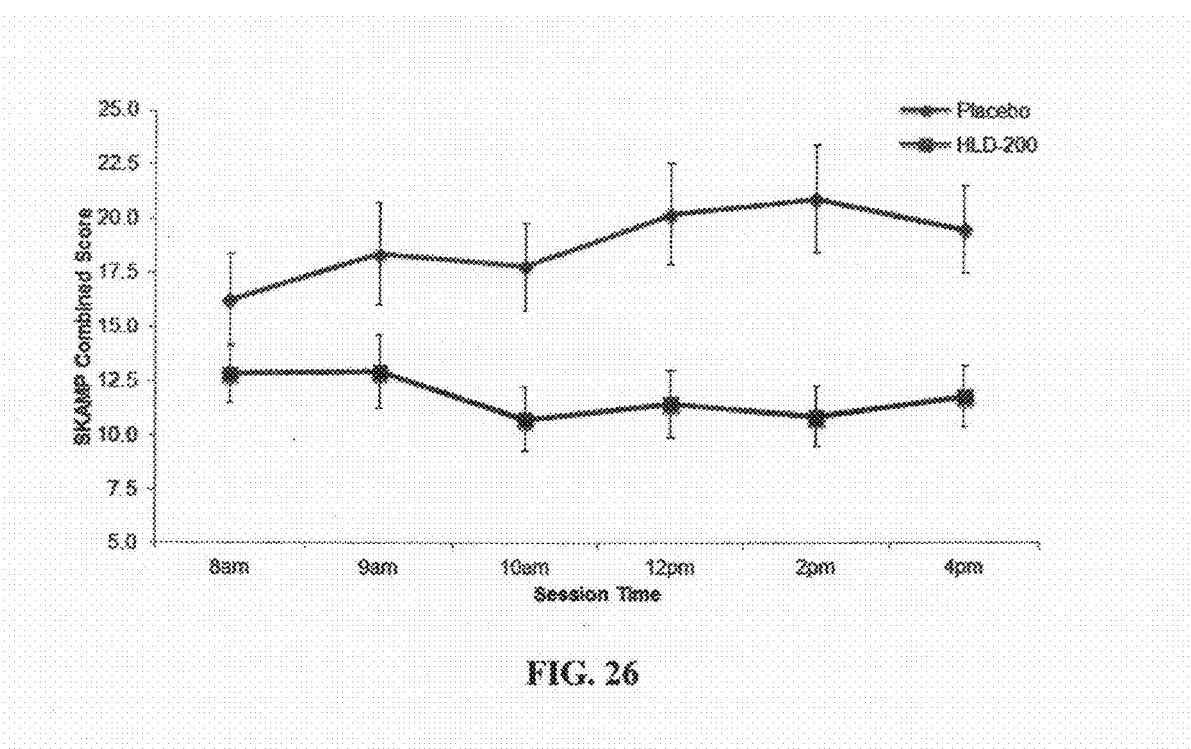
FIG. 26 is a graph of the primary endpoint SKAMP analysis from the clinical trial described in Example 32.

Results of the SKAMP Analysis is shown in FIG. 26. The upper curve marked with diamonds is the SKAMP combined score for the treated group and the lower curve, marked with squares is the placebo group. As seen from the figure, the drug HLD-200 improved control of ADHD symptoms as compared to placebo for at least an eight hour period, from 8:00 AM to 4:00 PM after a single dose administered the evening before.

Figure 27:
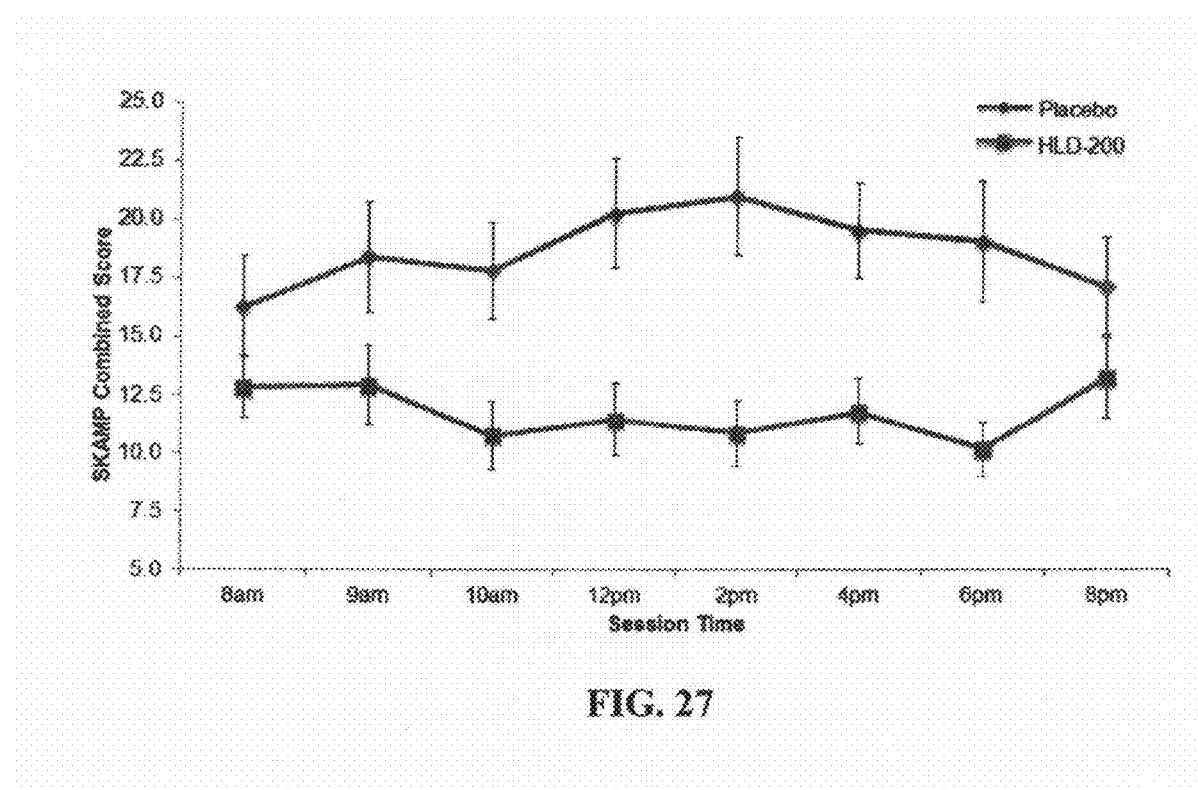
FIG. 27 is a graph of the SKAMP combined score analysis from the clinical trial described in Example 32.

As shown in the data in FIG. 27, the evening dosing of HLD-200 also controlled ADHD symptoms over a 12 hour period, from 8:00 AM to 8:00 PM when measured by the SKAMP combined score.

Figure 28:
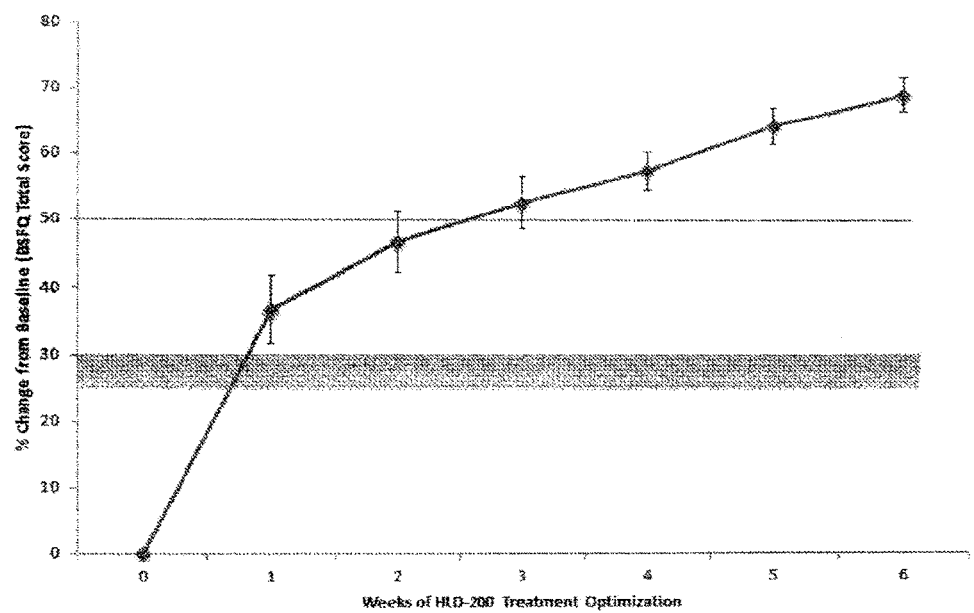
FIG. 28 is a graph of the BSFQ scores from the clinical trial described in Example 32.

The trial also demonstrated that the treatment significantly improved the morning functioning of subjects over the trial based on the BSFQ scores as compared to the base score, as shown in FIG. 28. Patients in the HLD-200 treatment arm showed a 58.5% improvement in their BSFQ scores at visit 9 (analog classroom test day) vs. their study initiation (visit 2) score.

Figure 29:
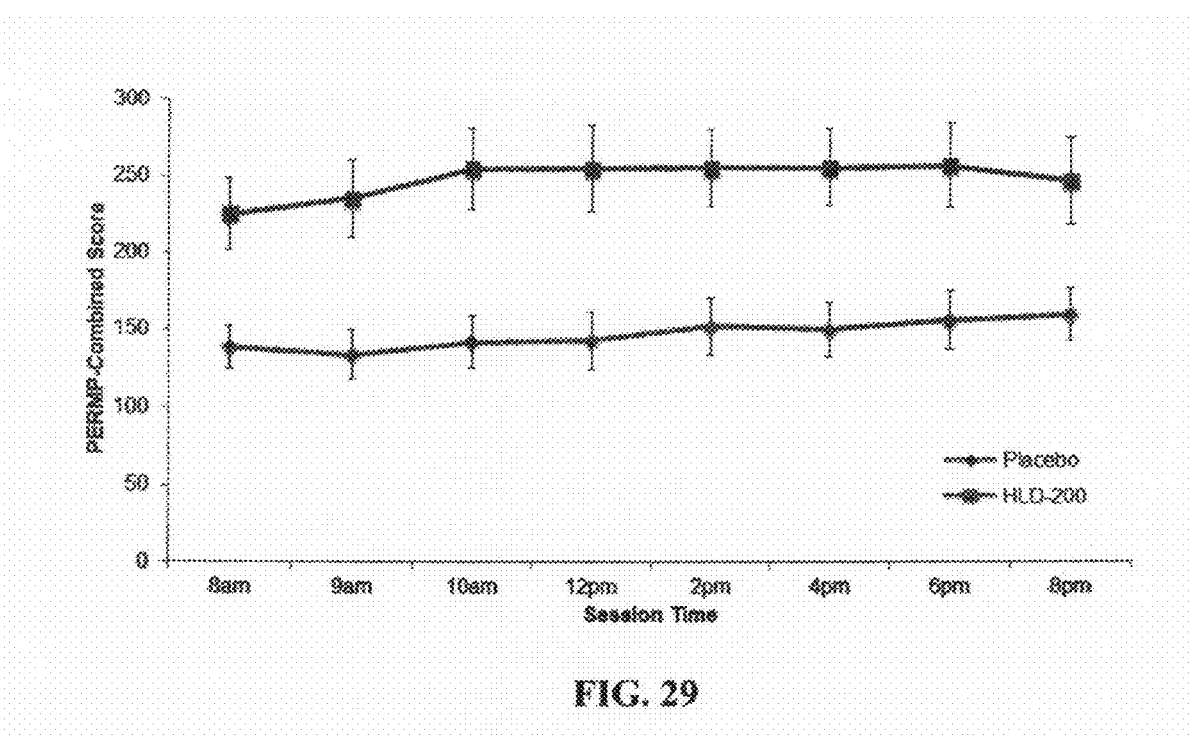
FIG. 29 is a graph of the PERMP combined scores from the clinical trial described in Example 32.

The sustained improvement of ADHD symptoms over a 12 hour classroom test day after an evening dose is also demonstrated by the PERMP combined scores as shown in FIG. 29. Again the upper curve marked by squares is the treated arm and the lower curve, marked by diamonds is the placebo arm. These scores demonstrate statistically significant improvement over the entire test day as compared to placebo, and further demonstrated a remarkable consistency of effect at every time point during the day.

Figure 30:
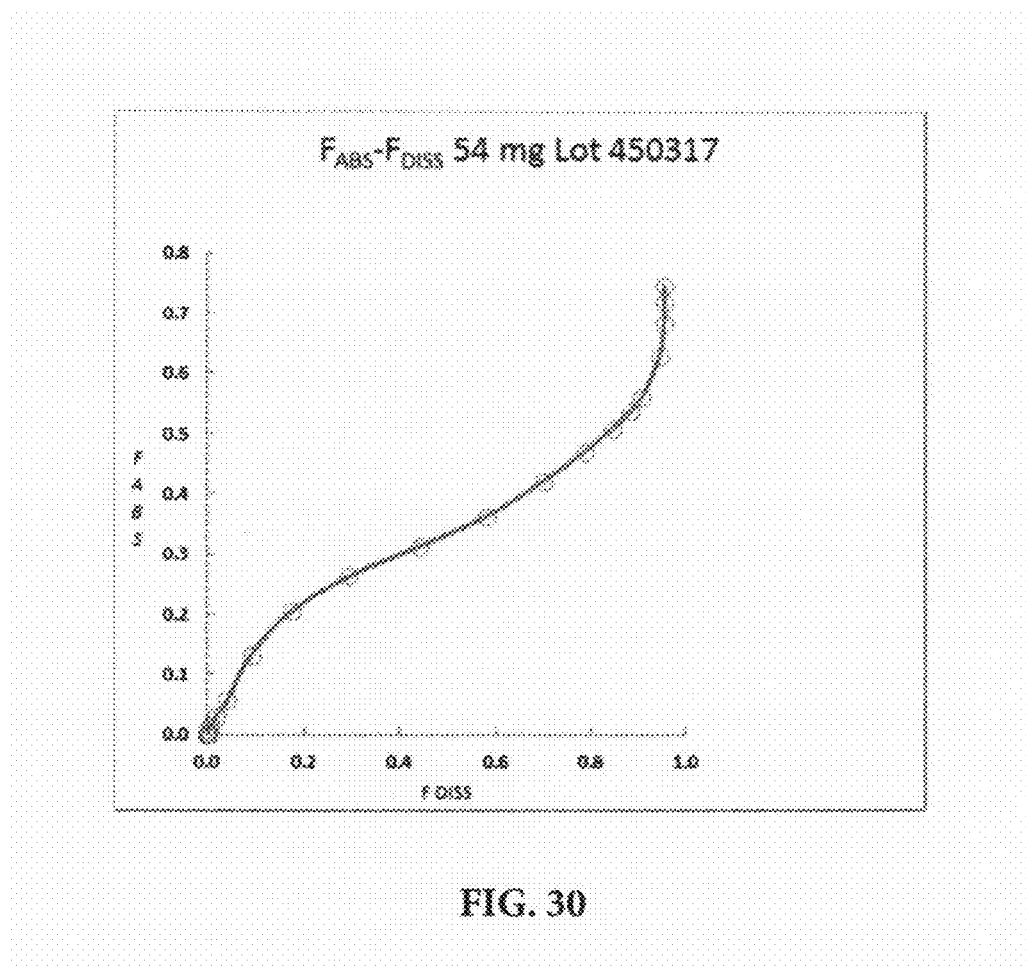
FIG. 30 is a graph of the fraction of drug absorbed vs. fraction dissolved of a formulation as described in Example 32.
Figure 31:
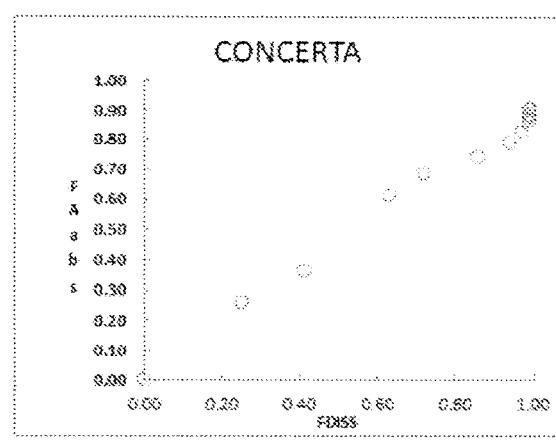
FIG. 31 is a comparative graph of the fraction of drug absorbed vs. fraction dissolved of a formulation of CONCERTA™.

The remarkably surprising consistency of effect of an evening dosed treatment for a period that extended for 12 hours led to further analysis. An analysis of the fraction of drug absorbed versus fraction of dissolution (IVIVC) is shown in FIG. 30. This curve is calculated by subtracting the effect of metabolism from the plasma concentration data. As shown in FIG. 30, the last half of the curve, starting at around 50-60% if the drug dissolution, the absorbance rate increases dramatically with respect to dissolution. For comparison, the same analysis was performed for CONCERTA™, an extended release formulation that is dosed in the morning as shown in FIG. 31. The curve shown in FIG. 31 demonstrates an approximately linear ratio of absorbed versus dissolution over this last half of the drug dissolution period. Without limiting the disclosure to any particular theory, it is contemplated that release of the drug in the colon and lower colon by the HLD-200 product results in a continued absorbance of active drug far later in the day. This effect is contemplated to be caused at least in part by the very different environment in the lower colon, which contains a higher concentration of solids and conversely less water. It is postulated that the absorbance of released drug is slower, providing newly absorbed drug to the patient for a much longer period toward the end of the day.

Figure 32:
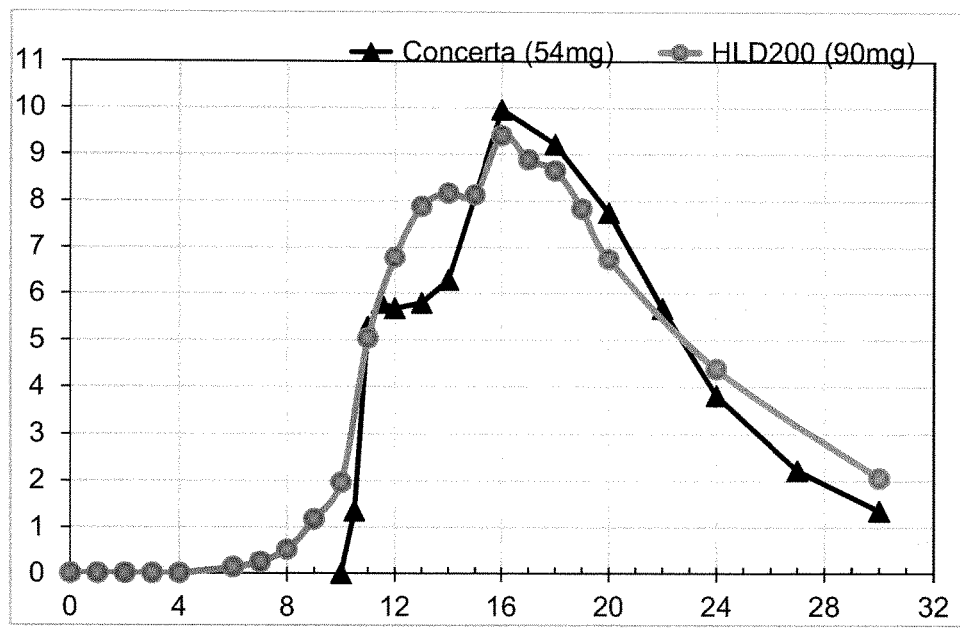
FIG. 32 is a comparative graph of the PK curves of HLD200 and CONCERTA™.

The described formulations thus provide benefits over the commercially available CONCERTA™ formulation both in the early morning hours as shown in FIG. 32 and late in the day as shown by the data in FIGS. 30 and 31.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of treating a subject with a disorder or condition responsive to the administration of a methylphenidate, comprising:
orally administering an effective amount of a methylphenidate or a pharmaceutical salt thereof in a formulation comprising one or more water soluble capsules containing a unit dose of methylphenidate or a pharmaceutical salt thereof in a solid dosage form that comprises a plurality of beads,
wherein said beads comprise a sustained release formulation comprising the methylphenidate or a pharmaceutical salt thereof enclosed in a delayed release coating that is insoluble in an aqueous medium at pH below 5.5,
wherein the sustained release formulation comprises a drug-containing core enclosed in a sustained release coating comprising ethyl cellulose and hydroxypropyl cellulose in a ratio of about 1:3 to 1:5, dibutyl sebacate and from 25% to 50% magnesium stearate, and
wherein the method comprises administering the unit dose form 5-8 hours prior to the desired treatment period.

2. The method of claim 1, wherein the delayed release coating comprises methacrylic acid copolymer type-B, mono- and di-glycerides and polysorbate 80.

3. The method of claim 1, wherein administration of the formulation is timed to administer the drug prior to a subject's bed time and to allow the subject to sleep during a period of absorption of less than 5% of the total therapeutic dose and to have absorbed a therapeutic level of drug at the anticipated time of awakening.

4. The method of claim 1, wherein the formulation is administered at night.

5. The method of claim 1, wherein the formulation is administered once a day.

6. The method of claim 1, wherein the formulation is administered more than once a day.

7. The method of claim 1, wherein the formulation is administered to a patient in a fasted state.

8. The method of claim 1, wherein the disorder or condition is attention deficit disorder, attention deficit hyperactivity disorder, excessive daytime sleepiness, major depressive disorder, bipolar depression, negative symptoms in schizophrenia, chronic fatigue, fatigue associated with chemotherapy or binge eating disorder.

9. The method of claim 1, wherein the disorder or condition is attention deficit disorder or attention deficit hyperactivity disorder.

10. The method of claim 1, wherein the disorder is binge eating disorder.

* * * * *